United States Patent [19]
Boel et al.

[11] Patent Number: 5,863,759
[45] Date of Patent: *Jan. 26, 1999

[54] PROCESS FOR THE PRODUCTION OF PROTEIN PRODUCTS IN ASPERGILLUS

[75] Inventors: Esper Boel, Holte; Tove Christensen; Helle Fabbicius Wöldike, both of Lyngby; Ida Birgitte Huge-Jensen, Jaegerspris, all of Denmark

[73] Assignee: Novo Nordisk A/S, Bagsvaerd, Denmark

[ * ] Notice: The term of this patent shall not extend beyond the expiration date of Pat. No. 5,536,661.

[21] Appl. No.: 463,957

[22] Filed: Jun. 5, 1995

Related U.S. Application Data

[63] Continuation of Ser. No. 208,092, Mar. 7, 1994, Pat. No. 5,536,661, which is a continuation of Ser. No. 236,605, Aug. 25, 1988, abandoned, which is a continuation-in-part of Ser. No. 24,342, Mar. 10, 1987, abandoned.

[30] Foreign Application Priority Data

| Mar. 17, 1986 | [DK] | Denmark | 1226/86 |
| Apr. 15, 1987 | [DK] | Denmark | 2054/88 |
| Aug. 28, 1987 | [DK] | Denmark | 4500/87 |
| Dec. 16, 1987 | [DK] | Denmark | 6560/87 |

[51] Int. Cl.$^6$ .............. C12P 21/02; C12N 1/15; C12N 9/20; C12N 15/11
[52] U.S. Cl. ............ 435/69.1; 435/71.1; 435/172.3; 435/198; 435/254.3; 536/24.1
[58] Field of Search ............. 435/69.1, 71.1, 435/172.3, 91.1, 254.3, 320.1, 198; 536/24.1; 935/6, 9, 22, 24, 33, 34, 59, 60, 61, 66, 68

[56] References Cited

U.S. PATENT DOCUMENTS

| 4,399,216 | 8/1983 | Axel et al. | 435/6 |
| 4,486,533 | 12/1984 | Lambowitz | 435/172.3 |
| 4,492,758 | 1/1985 | Esser et al. | 435/320.1 |
| 4,588,684 | 5/1986 | Brake et al. | 435/69.4 |
| 4,599,311 | 7/1986 | Kawasaki | 435/69.2 |
| 4,666,847 | 5/1987 | Alford et al. | 435/252.33 |
| 4,735,901 | 4/1988 | Kurtz et al. | 435/172.3 |
| 4,794,175 | 12/1988 | Nunberg et al. | 536/24.3 |
| 4,810,414 | 3/1989 | Huge-Jensen et al. | 510/320 |
| 4,816,405 | 3/1989 | Timberlake et al. | 435/243 |
| 4,863,864 | 9/1989 | Ashikari et al. | 435/205 |
| 4,885,249 | 12/1989 | Buxton et al. | 435/172.3 |
| 4,885,252 | 12/1989 | Ingolia et al. | 435/252.33 |
| 4,935,349 | 6/1990 | McKnight et al. | 435/69.5 |
| 5,198,345 | 3/1993 | Gwynne et al. | 435/69.1 |
| 5,364,770 | 11/1994 | Berka et al. | 435/69.1 |
| 5,536,661 | 7/1996 | Boel et al. | 435/254.3 |
| 5,578,463 | 11/1996 | Berka et al. | 435/69.1 |

FOREIGN PATENT DOCUMENTS

| 532180 | 3/1987 | Canada . |
| 1226/86 | 3/1986 | Denmark . |
| 1353/87 | 3/1987 | Denmark . |
| 682/87 | 3/1987 | Denmark . |
| 4500/87 | 8/1987 | Denmark . |
| 6560/87 | 12/1987 | Denmark . |
| 2054/88 | 8/1988 | Denmark . |
| 4760/88 | 8/1988 | Denmark . |
| 0126206 | 11/1984 | European Pat. Off. . |
| 071218 | 2/1986 | European Pat. Off. . |
| 0077109 | 4/1986 | European Pat. Off. . |
| 0184438 | 6/1986 | European Pat. Off. . |
| 0225078 | 6/1986 | European Pat. Off. . |
| 191221 | 8/1986 | European Pat. Off. . |
| 0215594 | 3/1987 | European Pat. Off. . |
| 0238023 | 9/1987 | European Pat. Off. . |
| 0249350 | 12/1987 | European Pat. Off. . |
| 0258068 | 3/1988 | European Pat. Off. . |
| 0305216 | 8/1988 | European Pat. Off. . |
| 871144 | 3/1987 | Finland . |
| 682/87 | 3/1987 | Ireland . |
| 62-60276 | 3/1987 | Japan . |
| 2116567 | 9/1983 | United Kingdom . |
| WO86/3774 | 7/1986 | WIPO . |
| WO860/6097 | 10/1986 | WIPO . |
| WO89/01969 | 9/1989 | WIPO . |
| WO91/17243 | 11/1991 | WIPO . |

OTHER PUBLICATIONS

Iimura et al., Nihon Nogei Kagakukai 1986 Lecture gists published 1986–Mar.–10.
Akins, R.A., et al. (1985) *Mol. and Cell. Biol.*, 5, 2272–2278.
Alber et al. (1982) *J. Mol. and Applied Genetics*, 1, 419–434.
Alton, N.K., et al. (1982) *Proc. Natl. Acad. Sci. USA*, 79, 1955–1959.
Arends, H. et al. (1984) *EMBO Journal*, 3, 377–382.
Arima et al. (1972) *Agric. Biol. Chem.* 36(5), 893–95.
Ballance, D.J., et al. (1983) *Biochem. and Biophys. Res. Comm.*, 112, 284–289.
Ballance, D.J., et al. (1985) *Gene.*, 36, 321–331.
Ballance et al. (1986) *Mol. Gen. Genet.*, 202,, 271–275.
Ballance et al. (1986) "Sequences Important for Gene (List continued on next page.)

*Primary Examiner*—David Guzo
*Assistant Examiner*—Nancy J. Degen
*Attorney, Agent, or Firm*—Steve T. Zelson; Elias J. Lambiris

[57] ABSTRACT

A process for expression of a protein product in *Aspergillus oryzae* is disclosed. The process comprises transforming *Aspergillus oryzae* with a vector system comprising DNA-sequences encoding functions facilitating gene expression, a suitable marker for selection of transformants, and a DNA-sequence encoding the desired protein product. The process enables industrial production of many different polypeptides and proteins in *A. oryzae*. Examples of such products are chymosin or prochymosin and other rennets, proteases, lipases and amylases. Also disclosed is an effective promoter for expression of a protein in Aspergillus. A preferred promoter is the TAKA-amylase promoter or functional parts thereof. There is also provided a process for the production of a recombinant Humicola lipase. The recombinant Humicola lipase from *A. oryzae* differs from the native lipase in having a greater glycosylation and in exhibiting an improved thermostability.

51 Claims, 28 Drawing Sheets

OTHER PUBLICATIONS

Expression in Filamentous fungi", —2,229.
Barnes, D.E., et al. (1986) *Cur. Genet.*, 10, 767–775.
Bech, et al. (1981) *Neth. Milk Dairy J.*, 35, 275–280.
Bennett (1985) *Gene Manipulations in Fungi*, Academic Press, 515–527.
Bennett (1985) *Molecular Genetics of Filamentous Fungi*, Alan R. Liss, Inc., 345–366.
Benoist et al. (1981) *Nature 290*, 304–310.
Beppu, T. (1983) *Trends in Biotech.*, 1, 85–89.
Berse, B., et al. (1983) *Gene*, 25, 109–117.
Berka et al. ( ) "Molecular Cloning, Analysis and Expression of the gla1 Gene Encoding a Thermostable, Raw Starch––Digesting Glucoamylase from the Fungus *Humicola grisea var. thermoidea*".
Berka et al. (1989) *Biotech, Adv.*, 7, 127–154.
Boel, E., et al. (1984) *EMBO Journal*, 3(7), 1581–1585.
Boel, E., et al. (1984) *EMBO, J. 3(5)*: 1097–1102.
Boel, E., et al. (1984) *Abstract P–26, EMBO Workshop*, The Netherlands.
Briggs, M.S., et al. (1986). *Adv. in Pro. Chem.*, 38, 109–180.
Bull, J.H., et al. (1984) *Nature*, 310, 701–704.
Burnett, "An Introduction to the Fungi", Chapter 1, Section 1—Structure and Growth, pp. 1–16.
Buxton, F.P., et al. (1983) *Mol. Gen. Genet*, 190, 403–405.
Buxton, F.P., et al. (1984) *Mol. Gen. Genet*, 196, 339–344.
Buxton, F.P., et al. (1985) *Gene.*, 37, 207–214.
Caddick, M.X., et al. (1986) *EMBO Journal*, 5, 1087–1090.
Case, M.E., et al. (1979) *Proc. Natl. Acad. Sci USA*, 76, 5259–5263.
Chen et al. (1984) *Acta Genet Sin*, 11 (3), 159–170 (Also, translation of p. 190 provided.)
Cheng et al. (1990) *Curr. Genet.*, 18, 453–456.
Christensen (1988) *Biotechnology* 6, 1419–1422.
Ciuffetti et al. *Molecular Biolog of Plant–Pathogen Interactions*, p. 278, Abstract Y 305.
Clements, J.M., et al. (1986) *Gene.*, 44, 97–105.
Cullen, D., et al. (1986) *Heredity*, 57, 131, Abstract No. 20.
Daboussi et al. (1989) *Current Genetics*, 15, 453–456.
Davies Leong (1990) "Molecular Biolgoy of a High–Level Recombinant Protein Production System in Aspergillus", Molecular Industry Mycology, Chptr. 3, pp. 45–81, Marcel Dekker, Inc.
Dhawale, S.S., et al. (1985) *Current Genetics*, 10, 205–212.
Doy, C.H., et al. (1985) *DNA*, 4, 105–114.
Durrens, P., et al. (1986) *Mol. Gen. Genet.*, 203, 544–549.
Emtage, J.S., et al. (1983) *Proc. Natl. Acad. Sci. USA*, 80, 3671–3675.
Freer, S.N. (1983) *Agr. Res. Ser., USDA*, 175–193.
Goff, C.G., et al. (1984) *Gene.*, 27, 35–46.
Gossen et al. (1984) ??. *Euro. Congr. Biotechn.*, 111–311—111–314.
Goosen et al. (1984) *Abstract P–22, EMBO Workshop*, The Netherlands.
Gossen et al. (1984) *Abstract P–8, EMBO Workshop*, The Netherlands.
Gotz et al. (1985) *Neuclic Acids Res.* 13, 5895–5906.
Grant, D.M., et al. (1984) *Mol. and Cell. Biol.*, 4, 2041–2051.
Grosveld et al. (1982) *Nature 295*, 120–126.
Gubler et al. (1983) *Gene 25*, 263–69.
Gwynne et al. (1987) *Biotechnology*, 5, 713–719.
Hahm et al. (1990) *Agric. Biol. Chem.*, 54, 25B–2520.
Hamer et al. (1987) *Molecular and Cellular Biology*, 7(7), 2352–2359.
Harris et al. (1982) *Nucleic Acids Res.* 10(7): 2177–2187.
Hawker et al. (1991) *Gene*, 100, 237–240.
Hayenga, K., et al. (1986) *J. Cell. Bio. Supp.*, vol. 0, No. 10, Part A, Abstract E109, 274.
Heyneker, H.L., et al. (1986) *Proc. of Bio Expo.*, 86, 145–149.
Hidaka, M., et al. (1986) *Gene.*, 43, 197–203.
Huiet, L., et al. (1986) *Proc. Natl. Acad. Sci. USA*, 83, 3381–3385.
Hynes, M.J., et al. (1983) *Mol. and Cell. Biol.*, 3, 1430–1439.
Hynes, M.J. (1986) *Experimental Mycology*, 10, 1–8.
Iimura et al. (1987) *Agricultural and Biological Chemistry 51*, 323–28.
Innis, M.A., et al. (1985) *Science*, 228, 21–26.
John et al. (1984) *Enzyme Microb. Technol.*, 6, 386.
Johnstone (1984) *Abstract P–30, EMBO Workshop*, The Netherlands.
Johnstone, I.L. (1985) *Microbiol. Sci. 2.*, 307–311.
Johnstone, I.L., et al. (1985) *EMBO Journal*, 4, 1307–1311.
Kawaguchi, Y., et al. (1984) *Journal of Biotechnology*, 1, 307–315.
Keesey, Jr., J.K., et al. (1982) *Journal of Bacteriology*, 152, 954–958.
Kelly, J.M., et al. (1985) *EMBO Journal*, 4, 475–479.
Kinnaird, J.H., et al. (1983) *Gene*, 26, 253–260.
Kinsey, J.A., et al. (1984) *Mol. and Cell. Biol.*, 4, 117–122.
Kolar et al., "Molecular and Functional Analysis of the Promoter Region of the *Penicilllium Chryosogenum* IPNS Gene", Abstract P18.
Kos et al. (1984) *Abstract P–33 and Poster, EMBO Workshop*, The Netherlands.
Kos, A., et al. (1985) *Gene*, 39, 231–238.
Krieg et al. (1984) *J. Mol. Biol.*, 180: 615–640.
Kück, U., et al. *Progress in Botany*, 46, 201–204 (1984).
Kugimiya et al. (1986) *Biochem. Biophys. Res. Comm.*, 141, 185–90.
Kuiper, M. T. R., et al. *Current Genetics*, 9, 471–477.
Legerton, T. L., et al. (1985) *Gene*, 39, 129–140.
Liang et al. (1982) *Acta. Microbiol. Sin.*, 22(3), 248–256.
Marston, F.A.O., et al. (1984) *Biotechnology*, 2, 800–804.
Mattern et al. (1987) *Mol. Gen. Genet.*, 210, pp. 460–461.
McCaman, M.T., et al. (1985) *Journal of Biotechnology*, 2, 177–190.
McGuire, J. (1986) *Proc. of Bio Expo.*, 86, 121–141.
McKnight et al. (1981) *Cell 25*, 385–398.
McKnight et al. (1982) *Science 217*, 316–324.
McKnight, G.L. (1985) *J. Cell. Biochem. Suppl.*, 9C, 137.
McKnight, G.L., et al. (1986) *Cell*, 46, 143–147.
Mellor, J., et al. (1983) *Gene.*, 24, 1–14.
Miller, B.L., et al. (1985) *Mol. and Cell Biol.*, 5, 1714–1721.
Minoda et al. (1969) *Agric. Biol. Chem.*, 33(4). 572–578.
Moir, D.T., et al., (1982) *Gene*, 19, 127–138.
Moir et al. (1983) *Chemical Abstracts*, vol. 98, No. 15, 173, Abstract 120575m.
Moir, D.T., et al. (1985) *Developments in Microbiology*, 26, 75–85.
Mullaney, E.J., et al. (1985) *Mol. Gen. Genet.*, 199, 37–45.
Münger, K., et al. (1985) *EMBO Journal*, 4, 2665–2668.
Newbury, S.F., et al. (1986) *Gene*, 43, 51–58.
Nishimori, K., et al. (1981) *J. Biochem.*, 90, 901–904.
Nishimori, K., et al. (1982) *J. Biochem.*, 91, 1085–1088.
Nishimori, K., et al. (1982) *Gene*, 19, 337–344.

Nishimori, K., et al. (1984) *Gene*, 29, 41–49.
Nunberg, J.A., et al. (1984) *Mol. and Cell. Biol.*, 4, 2306–2315.
Ohnuki et al. (1982) *Agric. Biol. Chem.*, 46(2), 451–458.
Orbach, M.J., et al. (1986) *Moll. & Cell. Biol.*, 6, 2452–2461.
Paietta, J., et al. (1985) *Current Genetics*, 9, 383–388.
Penttilä, M.E., et al. (1984) *Mol. Gen. Genet*, 194, 494–499.
Punt et al. (1987) *Gene*, 56, 117.
Rutledge, B.J. (1984) *Gene*, 32, 275–287.
Samson, Robert A. "Current Taxanomic Schemes of the Genus Asperigillus and its Teleomorphs", Chptr. 16, pp. 355–390.
Saunders, G., et al. (1986) *Trends in Biotechnology*, 4, 93–98.
Sebald, W., et al. (1984) *Abteilung für Botechnologische Forschung mbH., W. Germany*, 67–75.
Shoemaker, S., et al. (1983) *Biotechnology*, 1, 691–697.
Smith et al. (1990) *Gene 88*, 259–262.
Smith, R.A., et al. (1985) *Science*, 229, 1219–1224.
Smith, David, et al. "Cloning and Heterologous Expression of the Penicillin Biosynthetic Gene Cluster from *Penicillin Chryosogenum*", Department of Microbiology. University of Bristol, Abstract P49, p. 43.
Stahl, U., et al. (1982) *Proc. Natl. Acad. Sci. USA*, 79, 3641–3645.
Stohl, L.L., et al. (1983) *Proc. Natl. Acad. Sci. USA*, 80, 1058–1062.
Stohl, L.L., et al. (1984) *Nucleic Acids Research*, 12, 6169–6178.
Tilburn, J., et al. (1983) *Gene*, 26, 205–221.
Iimura Y., et al. (1987) *Agr. Biol. Chem.*, 51, 323–328.
Tudzynski, P., et al. (1980) *Cur. Genet.*, 2, 181–184.
Turgeon et al. (1985), *Mol. Gen. Genet.*, 201, 450–453.
Turner, G., et al. (1985) *Academic Press*, 259–277.
Ullrich et al. (1985), *Alan R. Liss*, Inc., 39–57.
Upshall, A. (1986) *Curr. Genet*, 10, 593–599.
Upshall, A. (1986), *Bio Techniques*, 4, 158–166.
Upshall, et al. (1987) *Biotechnology*, 5, 1301–1304.
Valenzuela et al. (1982) *Nature*, 298, 347–350.
Vallin et al. (1985) *Ciencias Biologias*, 14, 3–11.
van Brunt (1986) *Biotechnology*, 4(12), 1057–1062.
van den Hondel et al. (1985) *Mol. Gen. Genet.*, Alan R. Liss, Inc., 29–38.
van Gorcom (1984) Photos presented in Rhenen, "Construction of a System for the Cloning and Analysis of Promoters in Aspergillus: Expression of the *E. Coli* β–Galactosidase gene in *A. nidulans*".
van Gorcom et al. (1985) *Gene*, 40, 99–106.
van Gorcom et al. (1986) *Gene*, 48, 211–217.
von Gorcom et al. (1984) Third European Congress on Biotechnology, vol. III, Munchen Federal Republic of Germany, Sep. 10–14, 1984, pp. III–305—III–310.
van Hartingsveldt et al. (1987) *Mol. Gen. Genet.*, 206, 71.
Viebrock, A., et al. (1982) *EMBO Journal*, 1, 565–571.
Vollmer, S.J. et al. (1986) *Proc. Natl. Acad. Sci. USA*, 83 4869–4873.
Walker et al. (1983) *Nature 306*, 557–561.
Ward et al. (1973) *Bio. Abs.*, 56, No. 68797.
Ward et al. (1975) *Chem. Abs.*, 83, 401, No. 112391y.
Ward et al. (1988) *Curr. Genet.*, 14, 37–42.
Ward et al. (1990) *Biotechnology*, 8, 435–440.
Warren et al. (1984) *Cell*, 39(2):547–555.
Weiss, R.L., et al. (1985) *Expression of Aspergillus Genes in Neurospora in Gene Manipulation in Fungi*.
Wernars, K., et al. (1985) *Curr. Genet.*, 9, 361–368.
Whitehead et al. (1989) *Mol. Gen. Genet.*, 216, 408–411.
Woudt, L.P., et al. (1983) *Nucleic Acids Research*, 11, 5353–6346.
Woloshuk et al., *Molecular Biology of Plant–Pathogen Interactions*, Abstract Y 354, p. 294.
Yelton et al. (1983) *Proc. Natl. Acad. Sci. USA*, 80, 7576–7580.
Yelton, et al. (1984) *Proc. Natl. Acad. Sci. USA*, 81, 1470–1474.
Yelton, M.M., et al. (1985) *Proc. Natl. Acad. Sci. USA*, 82, 834–838.
Potrykus, et al. Protoplasts 1983, Lecture Proceedings, 6th International Protoplast Symposium, Basel, Aug. 12–16, 1983.
Ballance et al. "Sequences Impotant For Gene Expresion in Flamentas Fungi" Yeast 2: 229–236 1986.
Suggs et al. "Use of Synthetic Oligonucleotide as Hybridization Probes. . ." PNAS 78(11): 6613–6617 1981.
Liu et al. Agri. Biol. Chem. 37(1) 157–163 1973.
Toda et al. Proc Japan Acad. 58B 208 1982.

FIG. 1

```
              -1167      -1157      -1147      -1137      -1127
 -1176 AGATCTGCCC TTATAAATCT CCTAGTCTGA TCGTCGACGC ATTCCGAATA
                                          Sal I
 -1126 CGAGGCCTGA TTAATGATTA CATACGCCTC CGGGTAGTAG ACCGAGCAGC
 -1076 CGAGCCAGTT CAGCGCCTAA AACGCCTTAT ACAATTAAGC AGTTAAAGAA
 -1026 GTTAGAATCT ACGCTTAAAA AGCTACTTAA AAATCGATCT CGCAGTCCCG
  -976 ATTCGCCTAT CAAAACCAGT TTAAATCAAC TGATTAAAGG TGCCGAACGA
  -926 GCTATAAATG ATATAACAAT ATTAAAGCAT TAATTAGAGC AATATCAGGC
  -876 CGCGCACGAA AGGCAACTTA AAAAGCGAAA GCGCTCTACT AAACAGATTA
  -826 CTTTTGAAAA AGGCACATCA GTATTTAAAG CCCGAATCCT TATTAAGCGC
  -776 CGAAATCAGG CAGATAAAGC CATACAGGCA GATAGACCTC TACCTATTAA
  -726 ATCGGCTTCT AGGCGCGCTC CATCTAAATG TTCTGGCTGT GGTGTACAGG
  -676 GGCATAAAAT TACGCACTAC CCGAATCGAT AGAACTACTC ATTTTTATAT
  -626 AGAAGTCAGA ATTCATAGTG TTTTGATCAT TTTAAATTTT TATATGGCGG
                  EcoRI
  -576 GTGGTGGGCA ACTCGCTTGC GCGGGCAACT CGCTTACCGA TTACGTTAGG
  -526 GCTGATATTT ACGTGAAAAT CGTCAAGGGA TGCAAGACCA AAGTAGTAAA
  -476 ACCCCGGAAG TCAACAGCAT CCAAGCCCAA GTCCTTCACG GAGAAACCCC
  -426 AGCGTCCACA TCACGAGCGA AGGACCACCT CTAGGCATCG GACGCACCAT
  -376 CCAATTAGAA GCAGCAAAGC GAAACAGCCC AAGAAAAAGG TCGGCCCGTC
  -326 GGCCTTTTCT GCAACGCTGA TCACGGGCAG CGATCCAACC AACACCCTCC
  -276 AGAGTGACTA GGGGCGGAAA TTTAAAGGGA TTAATTTCCA CTCAACCACA
  -226 AATCACAGTC GTCCCCGGTA TTGTCCTGCA GAATGCAATT TAAACTCTTC
  -176 TGCGAATCGC TTGGATTCCC CGCCCCTAGT CGTAGAGCTT AAAGTATGTC
  -126 CCTTGTCGAT GCGATGTATC ACAACATATA AATACTAGCA AGGGATGCCA
   -76 TGCTTGGAGG ATAGCAACCG ACAACATCAC ATCAAGCTCT CCCTTCTCTG
                                          -1
   -26 AACAATAAAC CCCACAGAAG GCATTT
```

```
           4          14         24         34         44         54
           |          |          |          |          |          |
      ATGATGGTCGCGTGGTGGTCTCTATTTCTGTACGGCCTTCAGGTCGCGGCACCTGCTTTG
      MetMetValAlaTrpTrpSerLeuPheLeuTyrGlyLeuGlnValAlaAlaProAlaLeu 64         74         84         94        104        114
           |          |          |          |          |          |
      GCTGCAACGCCTGCGGACTGGCGATCGCAATCCATTTATTTCCTTCTCACGGATCGATTT
      AlaAlaThrProAlaAspTrpArgSerGlnSerIleTyrPheLeuLeuThrAspArgPhe
                       mature TAKA-amylase
         124        134
           |          |
      GCAAGGACGGATGGGTCGAC
      AlaArgThrAspGlySer
```

FIG. 4a

```
                  -1  1
ATCAGATTCCGACC   ATG CTC TTC TCT CAG ATT ACT TCT GCG ATC CTT TTA    36
                 MET LEU PHE SER GLN ILE THR SER ALA ILE LEU LEU   -58

ACA GCG GCT TCT TTG TCG CTT ACC ACT GCT CGC CCG GTA TCC AAG CAA    84
THR ALA ALA SER LEU SER LEU THR THR ALA ARG PRO VAL SER LYS GLN   -42

TCC GAG TCC AAG GAC AAG CTT CTG GCG CTT CCT CTC ACC TCG GTG TCC   132
SER GLU SER LYS ASP LYS LEU LEU ALA LEU PRO LEU THR SER VAL SER   -26

CGC AAG TTC TCT CAA ACC AAG TTC GGT CAG CAA CAA CTT GCT GAG AAG   180
ARG LYS PHE SER GLN THR LYS PHE GLY GLN GLN GLN LEU ALA GLU LYS   -10

CTA GCA GGT CTC AAG CCC TTC TCT GAA GCT GCC GCA GAC GGC TCC GTC   228
LEU ALA GLY LEU LYS PRO PHE SER GLU ALA ALA ALA ASP GLY SER VAL     7

GAT ACG CCC GGC TAT TAC GAC TTT GAT CTG GAG GAG TAT GCT ATT CCG   276
ASP THR PRO GLY TYR TYR ASP PHE ASP LEU GLU GLU TYR ALA ILE PRO    23

GTC TCC ATT GGT ACT CCT GGT CAA GAC TTT TTG CTC TTG TTC GAC ACT   324
VAL SER ILE GLY THR PRO GLY GLN ASP PHE LEU LEU LEU PHE ASP THR    39

GGC AGC TCC GAT ACT TGG GTT CCA CAC AAG GGT TGC ACC AAG TCT GAA   372
GLY SER SER ASP THR TRP VAL PRO HIS LYS GLY CYS THR LYS SER GLU    55

GGT TGT GTT GGC AGC CGA TTC TTT GAT CCA TCG GCT TCC TCC ACT TTT   420
GLY CYS VAL GLY SER ARG PHE PHE ASP PRO SER ALA SER SER THR PHE    71

AAA GCA ACT AAC TAC AAC CTA AAC ATC ACC TAC GGT ACT GGC GGC GCA   468
LYS ALA THR ASN TYR ASN LEU ASN ILE THR TYR GLY THR GLY GLY ALA    87

AAC GGT CTT TAC TTT GAA GAC AGC ATC GCT ATC GGC GAC ATC ACC GTG   516
ASN GLY LEU TYR PHE GLU ASP SER ILE ALA ILE GLY ASP ILE THR VAL   103

ACC AAG CAA ATT CTG GCT TAC GTC GAT AAT GTT CGC GGC CCA ACT GCT   564
THR LYS GLN ILE LEU ALA TYR VAL ASP ASN VAL ARG GLY PRO THR ALA   119

GAG CAG TCT CCT AAC GCT GAC ATT TTC CTT GAT GGT CTC TTT GGT GCA   612
GLU GLN SER PRO ASN ALA ASP ILE PHE LEU ASP GLY LEU PHE GLY ALA   135

GCC TAC CCA GAC AAC ACG GCC ATG GAA GCA GAG TAT GGA TCG ACT TAT   660
ALA TYR PRO ASP ASN THR ALA MET GLU ALA GLU TYR GLY SER THR TYR   151
```

FIG. 4b

```
AAC ACT GTT CAC GTC AAC CTC TAC AAG CAA GGC TTG ATC TCT TCT CCT    708
ASN THR VAL HIS VAL ASN LEU TYR LYS GLN GLY LEU ILE SER SER PRO    167

CTT TTC TCG GTC TAC ATG AAC ACT AAC AGC GGC ACT GGA GAG GTC GTC    756
LEU PHE SER VAL TYR MET ASN THR ASN SER GLY THR GLY GLU VAL VAL    183

TTT GGT GGA GTC AAC AAC ACG CTT CTC GGC GGC GAC ATT GCC TAC ACG    804
PHE GLY GLY VAL ASN ASN THR LEU LEU GLY GLY ASP ILE ALA TYR THR    199

GAC GTT ATG AGT CGT TAT GGT GGT TAT TAC TTC TGG GAC GCA CCC GTC    852
ASP VAL MET SER ARG TYR GLY GLY TYR TYR PHE TRP ASP ALA PRO VAL    215

ACA GGT ATC ACC GTC GAT GGA TCT GCT GCT GTC AGG TTC TCG AGA CCC    900
THR GLY ILE THR VAL ASP GLY SER ALA ALA VAL ARG PHE SER ARG PRO    231

CAA GCA TTC ACC ATC GAT ACT GGC ACC AAC TTT TTC ATT ATG CCC TCA    948
GLN ALA PHE THR ILE ASP THR GLY THR ASN PHE PHE ILE MET PRO SER    247

AGC GCC GCT TCT AAG ATT GTC AAA GCA GCT CTC CCT GAT GCC ACT GAA    996
SER ALA ALA SER LYS ILE VAL LYS ALA ALA LEU PRO ASP ALA THR GLU    263

ACC CAG CAG GGC TGG GTT GTT CCT TGC GCT AGC TAC CAG AAC TCC AAG   1044
THR GLN GLN GLY TRP VAL VAL PRO CYS ALA SER TYR GLN ASN SER LYS    279

TCG ACT ATC AGC ATC GTC ATG CAA AAG TCC GGC TCA AGC AGT GAC ACT   1092
SER THR ILE SER ILE VAL MET GLN LYS SER GLY SER SER SER ASP THR    295

ATT GAG ATC TCG GTT CCT GTC AGC AAA ATG CTT CTT CCA GTC GAC CAA   1140
ILE GLU ILE SER VAL PRO VAL SER LYS MET LEU LEU PRO VAL ASP GLN    311

TCG AAC GAG ACT TGC ATG TTT ATC ATT CTT CCC GAC GGT GGT AAC CAG   1188
SER ASN GLU THR CYS MET PHE ILE ILE LEU PRO ASP GLY GLY ASN GLN    327

TAC ATT GTT GGC AAC TTG TTC CTG CGC TTC TTT GTC AAT GTT TAC GAC   1236
TYR ILE VAL GLY ASN LEU PHE LEU ARG PHE PHE VAL ASN VAL TYR ASP    343

TTT GGC AAC AAC CGT ATC GGC TTT GCA CCT TTG GCC TCG GCT TAT GAA   1284
PHE GLY ASN ASN ARG ILE GLY PHE ALA PRO LEU ALA SER ALA TYR GLU    359

AAC GAG TAA  AGGGGCACCAATTCTTCTTTAGCTGCTCAGATAACTTTGTAACTCTCTGA   1343
ASN GLU TERM

TATACTCTTTATAACCTTTATTTCTCACTTTTTAACTGTATTCCAATACATTATTTCCT      1402
```

FIG. 12

```
    -1  1
    ATCAGAATC ATG GTT CTC AAG CAG CGT GCA AAC TAT CTG GGC TTT CTG ATT GTA TTC TTC   51
              MET VAL LEU LYS GLN ARG ALA ASN TYR LEU GLY PHE LEU ILE VAL PHE PHE  -78

ACG GCG TTC CTG GTC GAA GCC GTG CCA ATC AAG AGA CAA TCA AAC AGC ACG GTG GAT AGT  111
THR ALA PHE LEU VAL GLU ALA VAL PRO ILE LYS ARG GLN SER ASN SER THR VAL ASP SER  -58

CTG CCA CCC CTC ATC CCC TCT CGA ACC TCG GCA CCT TCA TCA TCA CCA AGC ACA ACC GAC  171
LEU PRO PRO LEU ILE PRO SER ARG THR SER ALA PRO SER SER SER PRO SER THR THR ASP  -38

CCT GAA GCT CCA GCC ATG AGT CGC AAT GGA CCG CTG CCC TCG GAT GTA GAG ACT AAA TAT  231
PRO GLU ALA PRO ALA MET SER ARG ASN GLY PRO LEU PRO SER ASP VAL GLU THR LYS TYR  -18

GGC ATG GCT TTG AAT GCT ACT TCC TAT CCG GAT TCT GTG GTC CAA GCA ATG AGC ATT GAT  291
GLY MET ALA LEU ASN ALA THR SER TYR PRO ASP SER VAL VAL GLN ALA MET SER ILE ASP    3

GGT GGT ATC CGC GCT GCG ACC TCG CAA GAA ATC AAT GAA TTG ACT TAT TAC ACT ACA CTA  351
GLY GLY ILE ARG ALA ALA THR SER GLN GLU ILE ASN GLU LEU THR TYR TYR THR THR LEU   23

TCT GCC AAC TCG TAC TGC CGC ACT GTC ATT CCT GGA GCT ACC TGG GAC TGT ATC CAC TGT  411
SER ALA ASN SER TYR CYS ARG THR VAL ILE PRO GLY ALA THR TRP ASP CYS ILE HIS CYS   43

GAT GCA ACG GAG GAT CTC AAG ATT ATC AAG ACT TGG AGC ACG CTC ATC TAT GAT ACA AAT  471
ASP ALA THR GLU ASP LEU LYS ILE ILE LYS THR TRP SER THR LEU ILE TYR ASP THR ASN   63

GCA ATG GTT GCA CGT GGT GAC AGC GAA AAA ACT ATC TAT ATC GTT TTC CGA GGT TCG AGC  531
ALA MET VAL ALA ARG GLY ASP SER GLU LYS THR ILE TYR ILE VAL PHE ARG GLY SER SER   83

TCT ATC CGC AAC TGG ATT GCT GAT CTC ACC TTT GTG CCA GTT TCA TAT CCT CCG GTC AGT  591
SER ILE ARG ASN TRP ILE ALA ASP LEU THR PHE VAL PRO VAL SER TYR PRO PRO VAL SER  103

GGT ACA AAA GTA CAC AAG GGA TTC CTG GAC AGT TAC GGG GAA GTT CAA AAC GAG CTT GTT  651
GLY THR LYS VAL HIS LYS GLY PHE LEU ASP SER TYR GLY GLU VAL GLN ASN GLU LEU VAL  123

GCT ACT GTT CTT GAT CAA TTC AAG CAA TAT CCA AGC TAC AAG GTT GCT GTT ACA GGT CAC  711
ALA THR VAL LEU ASP GLN PHE LYS GLN TYR PRO SER TYR LYS VAL ALA VAL THR GLY HIS  143

TCA CTC GGT GGT GCT ACT GCG TTG CTT TGC GCC CTG GGT CTC TAT CAA CGA GAA GAA GGA  771
SER LEU GLY GLY ALA THR ALA LEU LEU CYS ALA LEU GLY LEU TYR GLN ARG GLU GLU GLY  163

CTC TCA TCC AGC AAC TTG TTC CTT TAC ACT CAA GGT CAA CCA CGG GTA GGC GAC CCT GCC  831
LEU SER SER SER ASN LEU PHE LEU TYR THR GLN GLY GLN PRO ARG VAL GLY ASP PRO ALA  183

TTT GCC AAC TAC GTT GTT AGC ACC GGC ATT CCT TAC AGG CGC ACG GTC AAT GAA CGA GAT  891
PHE ALA ASN TYR VAL VAL SER THR GLY ILE PRO TYR ARG ARG THR VAL ASN GLU ARG ASP  203

ATC GTT CCT CAT CTT CCA CCT GCT GCT TTT GGT TTT CTC CAC GCT GGC GAG GAG TAT TGG  951
ILE VAL PRO HIS LEU PRO PRO ALA ALA PHE GLY PHE LEU HIS ALA GLY GLU GLU TYR TRP  223

ATT ACT GAC AAT AGC CCA GAG ACT GTT CAG GTC TGC ACA AGC GAT CTG GAA ACC TCT GAT 1011
ILE THR ASP ASN SER PRO GLU THR VAL GLN VAL CYS THR SER ASP LEU GLU THR SER ASP  243

TGC TCT AAC AGC ATT GTT CCC TTC ACA AGT GTT CTT GAC CAT CTC TCG TAC TTT GGT ATC 1071
CYS SER ASN SER ILE VAL PRO PHE THR SER VAL LEU ASP HIS LEU SER TYR PHE GLY ILE  263

AAC ACA GGC CTC TGT ACT TAA GAAATACCAGTTATACGATATGTAGGAAGTAGTATTTTTTAGGAAGAGATT 1131
ASN THR GLY LEU CYS THR TERM

TATATGTATTAAACAAATATATATATATATATACCGCTGCGCGAGAACCTGTATT POLYA
```

FIG. 14

RML 5' SYNTHETIC FRAGMENT

```
BamHI
                Met  Val  Leu  Lys  Gln  Arg  Ala  Asn
G A T C C A C C A T G G T A C T T A A G C A G C G C G C A A A C
        G T G G T A C C A T G A A T T C G T C G C G C G T T T G
                 NcoI                          BssHII

Tyr   Leu  Gly  Phe  Leu  Ile  Val  Phe  Phe  Thr  Ala
T A C C T A G G A T T T C T G A T T G T A T T C T T C A C G G C C
A T G G A T C C T A A A G A C T A A C A T A A G A A G T G C C G G
        AvrII

Phe  Leu  Val  Glu  Ala  Val  Pro  Ile  Lys  Arg  Gln
T T C C T G G T G G A A G C G G T A C C C A T C A A G A G A C A A
A A G G A C C A C C T T C G C C A T G G G T A G T T C T C T G T T
                           KpnI

Ser  Asn  Ser  Thr  Val  Asp  Ser  Leu  Pro  Pro  Leu
T C G A A T T C C A C G G T C G A C A G T C T G C C G C C T C T C
A G C T T A A G G T G C C A G C T G T C A G A C G G C G G A G A G
        EcoRI              SalI

Ile  Pro  Ser  Arg  Thr  Ser  Ala
A T C C C C T C G A G A A C C T C G
T A G G G G A G C T C T T G G A G C C G T G
        XhoI                   BanI
```

FIG. 18a

```
         60        70        80        90       100       110
          |         |         |         |         |         |
        ATGAGGAGCTCCCTTGTGCTGTTCTTTGTCTCTGCGTGGACGGCCTTGGCCAGTCCTATT
          M  R  S  S  L  V  L  F  F  V  S  A  W  T  A  L  A  S  P  I 120       130       140       150       160       170
          |         |         |         |         |         |
        CGTCGAGAGGTCTCGCAGGATCTGTTTAACCAGTTCAATCTCTTTGCACAGTATTCTGCA
          R  R  E  V  S  Q  D  L  F  N  Q  F  N  L  F  A  Q  Y  S  A 180       190       200       210       220       230
          |         |         |         |         |         |
        GCCGCATACTGCGGAAAAAACAATGATGCCCCAGCTGGTACAAACATTACGTGCACGGGA
          A  A  Y  C  G  K  N  N  D  A  P  A  G  T  N  I  T  C  T  G 240       250       260       270       280       290
          |         |         |         |         |         |
        AATGCCTGCCCCGAGGTAGAGAAGGCGGATGCAACGTTTCTCTACTCGTTTGAAGACTCT
          N  A  C  P  E  V  E  K  A  D  A  T  F  L  Y  S  F  E  D  S 300       310       320       330       340       350
          |         |         |         |         |         |
        GGAGTGGGCGATGTCACCGGCTTCCTTGCTCTCGACAACACGAACAAATTGATCGTCCTC
          G  V  G  D  V  T  G  F  L  A  L  D  N  T  N  K  L  I  V  L 360       370       380       390       400       410
          |         |         |         |         |         |
        TCTTTCCGTGGCTCTCGTTCCATAGAGAACTGGATCGGGAATCTTAACTTCGACTTGAAA
          S  F  R  G  S  R  S  I  E  N  W  I  G  N  L  N  F  D  L  K 420       430       440       450       460       470
          |         |         |         |         |         |
        GAAATAAATGACATTTGCTCCGGCTGCAGGGGACATGACGGCTTCACTTCGTCCTGGAGG
          E  I  N  D  I  C  S  G  C  R  G  H  D  G  F  T  S  S  W  R
```

FIG. 18b

```
       480       490       500       510       520       530
        |         |         |         |         |         |
     TCTGTAGCCGATACGTTAAGGCAGAAGGTGGAGGATGCTGTGAGGGAGCATCCGACTAT
       S  V  A  D  T  L  R  Q  K  V  E  D  A  V  R  E  H  P  D  Y 540       550       560       570       580       590
        |         |         |         |         |         |
     CGCGTGGTGTTTACCGGACATAGCTTGGGTGGTGCATTGGCAACTGTTGCCGGAGCAGAC
       R  V  V  F  T  G  H  S  L  G  G  A  L  A  T  V  A  G  A  D 600       610       620       630       640       650
        |         |         |         |         |         |
     CTGCGTGGAAATGGGTATGATATCGACGTGTTTTCATATGGCGCCCCCCGAGTCGGAAAC
       L  R  G  N  G  Y  D  I  D  V  F  S  Y  G  A  P  R  V  G  N 660       670       680       690       700       710
        |         |         |         |         |         |
     AGGGCTTTTGCAGAATTCCTGACCGTACAGACCGGCGGAACACTCTACCGCATTACCCAC
       R  A  F  A  E  F  L  T  V  Q  T  G  G  T  L  Y  R  I  T  H 720       730       740       750       760       770
        |         |         |         |         |         |
     ACCAATGATATTGTCCCTAGACTCCCGCCGCGCGAATTCGGTTACAGCCATTCTAGCCCA
       T  N  D  I  V  P  R  L  P  P  R  E  F  G  Y  S  H  S  S  P 780       790       800       810       820       830
        |         |         |         |         |         |
     GAGTACTGGATCAAATCTGGAACCCTTGTCCCCGTCACCCGAAACGATATCGTGAAGATA
       E  Y  W  I  K  S  G  T  L  V  P  V  T  R  N  D  I  V  K  I 840       850       860       870       880       890
        |         |         |         |         |         |
     GAAGGCATCGATGCCACCGGCGGCAATAACCAGCCTAACATTCCGGATATCCCTGCGCAC
       E  G  I  D  A  T  G  G  N  N  Q  P  N  I  P  D  I  P  A  H 900       910       920       930
        |         |         |         |
     CTATGGTACTTCGGGTTAATTGGGACATGTCTTTAG
       L  W  Y  F  G  L  I  G  T  C  L  -
```

PROCESS FOR THE PRODUCTION OF PROTEIN PRODUCTS IN ASPERGILLUS

This application is a continuation of U.S. Ser. No. 08/208,092, filed Mar. 7, 1994, now U.S. Pat. No. 5,536,661; which in turn is a continuation of U.S. Ser. No. 07/236,605, filed Aug. 25, 1988, now abandoned; which in turn is a continuation-in-part of U.S. Ser. No. 07/024,342, filed Mar. 10, 1987, now abandoned.

BACKGROUND OF THE INVENTION

The present invention relates to a process for expression of protein products in *Aspergillus oryzae*, recombinant DNA vectors, a promoter for Aspergillus and transformed fungi.

In the past, numerous processes have been developed for the production of polypeptides or proteins by means of the recombinant DNA technology. The main interest has been concentrated on bacteria and yeast, e.g. *E. coli, Bacillus subtilis* and *Saccharomyces cerevisiae* being well characterized species as regards for instance expression and selection systems.

Besides the above mentioned microorganisms, filamentous fungi, such as *Aspergillus niger*, are attractive candidates as host microorganisms for recombinant DNA vectors being well-characterized and widely used microorganisms for the commercial production of enzymes. Efforts have especially been concentrated on the development of transformation systems by which a selection marker permitting selection of transformants from the untransformed host microorganisms is used.

In the last few years different selection markers for the transformation of *Aspergillus nidulans* have been described and procedures have recently been developed for integrative transformation of the filamentous fungus *Aspergillus nidulans* for the purpose of investigation of the genetic and molecular processes controlling fungal cell differentiation.

Transformation of *A. nidulans* has been demonstrated by using plasmids containing the *Neurospora crassa* pyr-4 gene (Ballance, D. J. et al., Biochem.Biophys.Res.Commun., 112 (1983) 284–289), the *A. nidulans* amdS gene (Tilburn, J. G. et al., Gene 26 (1983) 205–221), the *A. nidulans* trpC gene (Yelton, M. M. et al., Proc.Natl.Acad.Sci. U.S.A., 81 (1984) 1470–1474) and the *A. nidulans* argB gene (John, M. A. and Peberdy J., Microb.Technol. 6 (1984) 386–389). The transforming DNA was found to be integrated into the host genome at rather low frequencies (typically <1000 transformants/µg of DNA).

Very recently transformation of *Aspergillus niger* with the amdS gene of *A. nidulans* was described (Kelly, J. M. and Hynes, M. J., EMBO Journal 4 (1985), 475–479) and amdS was shown to be a potential selection marker for use in transformation of *Aspergillus niger* that cannot grow strongly on acetamide as a sole nitrogen source. Transformation of *Aspergillus niger* using the argB gene of *Aspergillus nidulans* has also been described recently (Buxton, F. P. et al., Gene 37 (1985), 207–214).

So far no methods have been developed for expression of foreign proteins in the filamentous fungi *Aspergillus oryzae* mainly due to insufficient knowledge of how to control gene expression in this fungus and due to the lack of suitable selectable genetic markers on cloning vectors and it is one aim of the present invention to develop such methods.

The present invention is furthermore related to a process for recombinant DNA production of Humicola lipases and a recombinant Humicola lipase.

Humicola lipases are obtainable from strains of thermophilic *Humicola sp.*, including thermophilic *Thermomyces sp.*, such as *H. lanuginosa* (Griffon and Maublanc) Bunce, *H. stellata* Bunce, *H. grisea var. thermoidea*, Cooney & Emerson, *H. insolens*, Cooney & Emerson, *Thermomyces ibadanensis*, Apinis & Eggins, *H. hyalothermophila* Moubasher, Mazen and Abdel-Hafez, *H. grisea var. indica* Subrahmanyam, *H. brevis var. thermoidea*, Subrahmanyam and Thirumalachar and *H. brevispora* Subrahmanyam and Thirumalachar.

*H. lanuginosa* has also been described under the synonyms *Thermomyces lanuginosus* Tsiklinsky, *Sepedonium lanuginosum* Griffon and Maublanc, *Sepedonium thermaphilum cyclosporum* and *S. thermaphilum ovosporum* Velich, *Acremoniella sp.* Rege, *Acremoniella thermophila* Curzi and *Monotospora lanuginosa* (Griffon and Maublanc) Mason.

Moreover, the species *Scytalidium thermophilum* (Cooney & Emerson) Austwich was by Hedger (1975, The ecology of thermophilic fungi in Indonesia. In Biodegradation et Humification. Rapport du $1^{er}$ Colloque Internationel—Nancy 1974 (ed. G. Kilbertius, O. Reisinger, A. Mourey & J. A. Cancela Da Fonseca), Sarreguemines Pierron Editeur—57206) considered to belong to *Humicola insolens*.

Production of a *Humicola lanuginosa* lipase is described in Japanese unexamined patent publication No. 48-62990, and in EP patent application No. 87307684.8. The latter also teaches use of this lipase in lipolytic detergent additives.

Due to the world wide use of enzyme additives in detergents and due to the fact that Humicola lipases have turned out to be superior to known detergent lipases both as regards detergency and stability, commercial interest in such lipases is high.

In the production of industrial enzymes yields have always been important for the profitability of the production process. The traditional way of improvement is to mutate the wild strain so as to obtain higher yielding mutants. By means of recombinant DNA technology a further possibility is to transform the gene for the desired product into a host microorganism capable of producing higher yields than the wild strain or with other favourable characteristics.

Accordingly, another aim of the present invention to develop a method for the production of Humicola lipases by recombinant DNA-technology.

BRIEF DESCRIPTION OF THE INVENTION

According to the present invention it has now beer shown that the above transformation techniques can be used to obtain a high level of expression of heterologous proteins or to enhance the production of homologous proteins in *Aspergillus oryzae*.

As used herein the expression "heterologous proteins" means proteins not produced by *A. oryzae* whereas "homologous proteins" means proteins produced by *A. oryzae* itself.

More specifically it has been shown that selection for *A. oryzae* strains transformed with DNA encoding a desired protein product is possible by use of the marker genes used for transformation of *A. niger* and *A. nidulans*. Due to the phylogenetic distance between these latter fungi and *A. oryzae* (Raper, K. B. and Fennell, D. I. (1965) The Genus Aspergillus) this was by no means to be foreseen.

According to a first aspect of the present invention there Ls provided a process for expression of a protein product in *Aspergillus oryzae* comprising the steps of:

(a) providing a recombinant DNA cloning vector system capable of integration into the genome of an *Aspergillus oryzae* host in one or more copies and comprising: DNA-sequences encoding functions facilitating gene expression; a suitable marker for selection of transformants; and a DNA-sequence encoding the desired protein product;

(b) transforming the *Aspergilus oryzae* host which does not harbour a functional gene for the chosen selection marker with the recombinant DNA cloning vector system from step a; and (c) culturing the transformed *Aspergillus oryzae* host in a suitable culture medium.

According to a second aspect of the present invention there is provided a highly effective promoter for expression of a protein product in Aspergillus, especially in *Aspergillus oryzae* and *Aspergillus niger*, which promoter is characterized as being the TAKA-amylase promoter or functional parts thereof optionally preceded by upstream activating sequences.

According to a third aspect of the present invention there is provided a method for production of a protein product in *Aspergillus oryzae* by which method an *Aspergillus oryzae* strain being transformed with a recombinant DNA cloning vector system as described above is cultured in a suitable culture medium and the product is recovered from the culture medium.

According to the present invention it has furthermore been shown that it is possible to obtain a high level of expression of the *Humicola sp.* lipase in *Aspergillus sp.* strains or to enhance the production of the lipase in Humicola strains.

The present invention accordingly also provides a method for the production of Humicola lipases comprising the steps of (a) providing a suitable recombinant DNA cloning vector comprising DNA sequences encoding functions facilitating gene expression and a DNA sequence encoding the Humicola lipase;

(b) transforming a suitable host organism with the cloning vector from step (a);

(c) culturing the transformed host in a suitable culture medium and optionally recovering the lipase from the culture medium.

More narrowly there is provided a process for the production of Humicola lipases in Aspergillus comprising the steps of:

(a) providing a recombinant DNA cloning vector system capable of integration into the genome of an Aspergillus host in one or more copies and comprising: DNA sequences encoding functions facilitating gene expression; a suitable marker for selection of transformants; and a DNA sequence encoding the Humicola lipase;

(b) transforming the Aspergillus host which does not harbour a functional gene for the chosen selection marker with the recombinant DNA cloning vector system from step a; and (c) culturing the transformed Aspergillus host in a suitable culture medium and optionally recovering of the lipase from the culture medium.

According to a further aspect of the present invention there is provided a method for production of Humicola lipases in Aspergillus by which method an Aspergillus strain being transformed with a recombinant DNA cloning vector system as described above is cultured in a suitable culture medium and the lipase is recovered from the culture medium.

The present invention also provides a novel recombinant Humicola lipase product characterized by a difference in glycosylation from the native Humicola lipases previously known. That is, the nature and optionally the extent of glycosylation of the recombinant Humicola lapase of the present invention is different from the lipase obtained from the naturally occuring Humicola strains. The Humicola lipase product of this invention is furthermore characterized by an improved thermostability compared to the corresponding native Humicola lipase.

More specifically the novel recombinant Humicola lipase is characterized in that the carbohydrate content is of about the same level or is greater than the carbohydrate content in the native lipase whereas the nature of the glycosylation is different from the native Humicola lipase, i.e. the novel Humicola lipase contains other carbohydrates than the native lipase. The carbohydrate content may typically be from about 5 to about 30% (w/w), whereas the carbohydrate content in the native lipase is about 49% (w/w). More specifically the carbohydrate content may be in the range from about 5 to about 15% (w/w) and even more specifically it may be in the range from about 7.5% to about 8.5% (w/w).

The recombinant Humicola lipase product of this invention may be used as an enzymatic detergent additive for use in detergents in a similar way as the native lipase, i.e. as described in U.S. patent application Ser. No. 091,413 filed Aug. 28, 1987 for the lipase of *H. lanuginosa*.

As used in the present specification the term "recombinant Humicola lipase" is applied to Humicola lipase produced by culturing a microorganism transformed with the cDNA encoding the native Humicola lipase. The term "native Humicola lipase" is applied to the Humicola lipase obtained from natural sources of thermophilic *Humicola sp.*, including thermophilic *Thermomyces sp.* described in the introductory part of the present specification.

It has been found that recombinant Humicola lipase from *A. oryzae* is not identical with native Humicola lipase, notwithstanding that the peptide sequence is the same. Apparently the host microorganism glycosylates the expressed polypeptide to a different extent than the donor microorganism and with different sugar moieties. In *A. niger* the extent of glycosylation seems to be on the same level whereas the sugar moities seem to be of the same kind as in *A. oryzae*. Differentiation and identification of the native lipase and of the recombinant lipase is possible through measurement of their glycosylation. Thus, taking as exemplary the native *Humicola lanuginosa* lipase and the recombinant form of this lipase from an *A. oryzae* transformant, both lipases are N-glycosylated, but with different sugar residues. The native lipase does not have any galactose and has less mannose than the recombinant lipase and also is glycosylated to a different degree, the native lipase having carbohydrate moieties that add approximately 1500 Daltons to its molecular weight (about 5%) and the recombinant lipase having moieties that add about 2600 Daltons (about 8%).

The novel recombinant Humicola lipase according to the present invention may comprise from about 1 to about 12 mol galactose per mol lipase protein and more specifically from about 1 to about 6 mole galactose per mol lipase protein. The content of mannose may be from about 3 to about 20 and more specifically from about 3 to about 12 mol mannose per mol lipase protein. The recombinant Humicola lipase will typically comprise about 2 mol N-acetylglucosamine, from about 3 to about 20 mol mannose and from about 1 to about 12 mol galactose per mol lipase protein. More specifically the recombinant Humicola lipase will contain about 2 mol N-acetylglucoseamine, about 3 to about 12 mol mannose and about 1 to about 6 mol galactose per mol lipase product. Even more specifically the recombinant Humicola lipase will contain about 2 mol N-acetylglycoseamine, about 6 to about 9 mol mannose and about 2 to about 4 mol galactose per mol lipase protein.

The differences in glycosylation have some effect on the enzyme properties. In particular, the thermal stability of highly purified *H. lanuginosa* recombinant lipase is superior vis a vis the thermal stability of comparably purified native lipase. In addition, the stability of the pure recombinant lipase in the presence of an alkaline Bacillus protease (Esperase™) tested at 40° C. and at 55° C. is superior vis a vis comparably pure native lipase.

Characteristically, enzyme products, here lipase products, particularly extracellular lipase products contain other enzyme activities notably proteolytic activity and non-enzymatically active peptides and amino acids derived from culture broth constituents.

In the instance of the *Humicola sp.* lipase, the recombinant lipase product has been found to be thermally more stable than the comparable native lipase product. According to the data of the inventors hereof part of the improvement in thermal stability may be attributed to the different glycosylation, and another part may be attributed to the absence of the Humicola proteolytic activity in the recombinant lipase product. In the instance of the lipase native to *H. lanuginosa* a brief description thereof in U.S. Pat. No. 4,707,291 reports that a commercially available *H. lanuginosa* lipase product (Amano CE) contained a substantial level of proteolytic activity. The inventors' native *H. lanuginosa* lipase product contained a comparable level of proteolytic activity. At elevated temperatures in particular the protease can be expected to degrade other enzymes. The improvement in thermal stability attributable to absence of the protease is cumulative of the improvement attributable to different glycosylation.

BRIEF DESCRIPTION OF THE DRAWINGS

The present invention is further illustrated by reference to the accompanying drawings in which:

FIG. 1 shows the DNA-sequence of the TAKA-amylase promoter and upstream promoter regions, the preregion and the 5' part of the structural gene for the TAKA-amylase.

FIG. 4a and b shows the DNA sequence of prepro *Rhizomucor miehei* aspartic proteinase cDNA together with the deduced amino acid sequence given by three-letter abbreviations.

FIG. 12 shows the sequence of prepro *Rhizomucor miehei* lipase cDNA together with the deduced amino acid sequence given by three-letter abbreviations.

FIG. 14 shows the DNA sequence of a synthetic fragment RML5',

FIG. 18a and b shows the DNA sequence of prepro *Humicola lanuginosa* lipase CDNA together with the deduced amino acid sequence given by three-letter abbreviations.

DETAILED DESCRIPTION OF THE INVENTION

Figure 2:
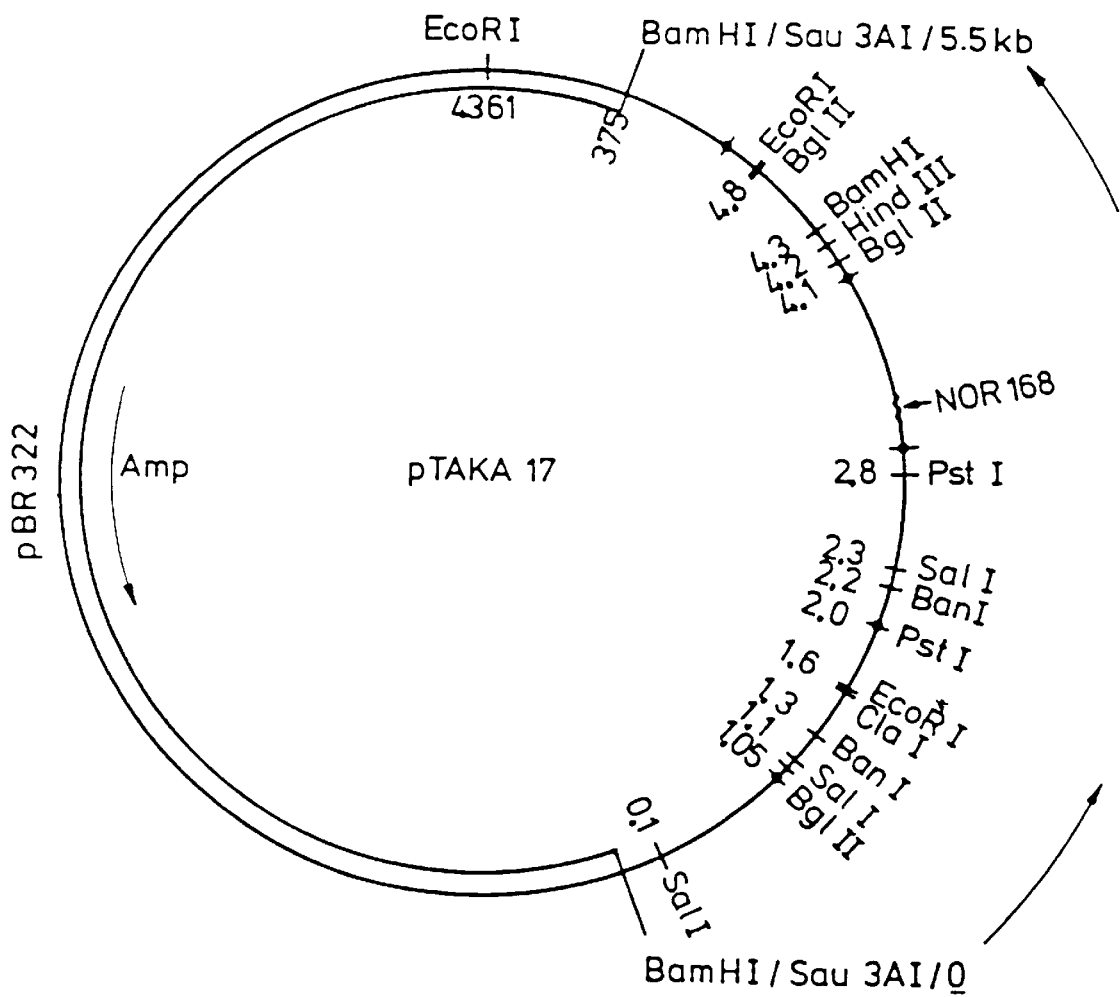
FIG. 2 shows an endonuclease restriction map of plasmid pTAKA17.

The transformation technique used was a method adapted from the methods for transformation of *A. nidulans* (Ballance et al., Biochem.Biophys.Res.Commun., 112 (1983), 284–289; Tilburn et al., Gene 26 (1983), 205–221, Yelton et al. Proc.Natl.Acad.Sci. USA, 81 (1984), 1470–1474) and similar to the method of Buxton et al. (Gene 37 (1985), 207–214) for transformation of *A. niger*. In the process of the present invention *Aspergillus oryzae* is transformed with a vector system containing a selection marker which is capable of being incorporated into the genome of the host strain, but which is not harboured in the host strain before the transformation. Transformants can then be selected and isolated from nontransformants on the basis of the incorporated selection marker.

Preferred selection markers are the argB (*A. nidulans* or *A. niger*), trpC (*A. nidulans*), amdS (*A. nidulans*) or pyr4 (*Neurospora crassa*) genes, or the DHFR (dihydrofolate reductase or mutants hereof) gene. More preferred selection markers are the argB or the amdS gene. Wild type *A. oryzae* strains are normally argB$^+$ (i.e. the argB gene is functional in *A. oryzae*). If argB is chosen as the selection marker an argB mutant strain of *A. oryzae* which has a defect in the gene for this marker must be used as host strain. *A. oryzae* argB mutants can be prepared as described by F. P. Buxton et al. (Gene 37 (1985), 207–214). An argB mutant is defined as a mutant having a defect in the ornithin transcarbamylase gene. On the other hand the amdS gene may be used as selection marker for the transformation of wild type *A. oryzae* as the wild type strains do not contain this gene.

DNA-sequences encoding functions facilitating gene expression are typically promoters, transcription terminators and polyadenylation signals.

The promoter, which might be preceded by upstream activating sequences and enhancer sequences as well known in the art, may be any DNA-sequence that might show strong transcriptional activity in Aspergillus and may be derived from genes encoding both extracellular and intracellular proteins, such as amylases, glucoamylases, proteases, lipases, cellulases and alycolytic enzymes. Suitable promoters may be derived from genes for *A. oryzae* TAKA amylase, *Rhizomucor miehei* aspartic proteinase, *A. niger* gluccamylase, *A. niger* neutral α-amylase, *A. niger* acid stable α-amylase, and *Rhizomucor miehei* lipase. Examples of promoters from genes for glycolytic enzymes are TPI, ADH and PGK.

A preferred promoter according to the present invention is the *A. oryzae* TAKA-amylase promoter. The TAKA amylase is a well known α-amylase (Toda et al., Proc.Japan Acad. 58 Ser. B (1982) 208–212). DNA encoding the promoter region was derived from the TAKA-amylase genomic clone. The sequence of the promoter and regions upstream to the promoter together with the preregion and the 5' end of the structural gene for the TAKA-amylase is illustrated in FIG. 1.

As described in further detail in example 2 a DNA-sequence encoding the TAKA-amylase including the preregion and promoter and upstream activating sequences was derived from a *A. oryzae* mycelium and inserted in BamHI digested pBR322 to give plasmid pTAKA 17 (see FIG. 2) In pTAKA 17 the *A. oryzae* derived DNA is shown as a 5.5 kb BamHI/Sau 3AI-BamHI/Sau 3AI fragment, the promoter and upstream activating sequences representing a 2.1 kb fragment starting at position O. The established DNA-sequence of the promoter and upstream activating sequences up to the BglII site is shown in FIG. 1. The promoter ends at nucleotide-1 preceding the Met(1) codon of the TAKA-amylase presequence. The nucleotide sequence encoding the presequence is constituted of 63 nucleotides and the mature TAKA-amylase starts at a position corresponding to nucleotide 64.

From pTAKA 17 the whole promoter sequence including sequences upstream to the promoter or functional parts thereof may be derived by means evident to the person skilled in the art. The promoter sequence may be provided with linkers with the purpose of introducing specific restriction sites facilitating the ligation of the promoter sequence with further DNA, for instance the gene encoding the desired protein product or different preregions (signal peptides).

In the method according to the present invention the sequence from nucleotide −1144 (see FIG. 1) (representing; the start of a SalI site) to nucleotide −10 has been used as one example of a well functioning part of the promoter region. In another embodiment of the present invention the nucleotide sequence from nucleotide −1176 to −1 was preceded by the still not sequenced 1.05 kb fragment from pTAKA 17. It is evident for the person skilled in the art that different fragments can be used.

According to one embodiment of the present invention the promoter and upstream activating sequences have the following sequence or a functionally equivalent nucleotide sequence:

```
GTCGACGC ATTCCGAATA CGAGGCCTGA TTAATGATTA CATACGCCTC
CGGGTAGTAG ACCGAGCAGC CGAGCCAGTT CAGCGCCTAA AACGCCTTAT
ACAATTAAGC AGTTAAAGAA GTTAGAATCT ACGCTTAAAA AGCTACTTAA
AAATCGATCT CGCAGTCCCG ATTCGCCTAT CAAAACCAGT TTAAATCAAC
TGATTAAAGG TGCCGAACGA GCTATAAATG ATATAACAAT ATTAAAGCAT
TAATTAGAGC AATATCAGGC CGCGCACGAA AGGCAACTTA AAAAGCGAAA
GCGCTCTACT AAACAGATTA CTTTTGAAAA AGGCACATCA GTATTTAAAG
CCCGAATCCT TATTAAGCGC CGAAATCAGG CAGATAAAGC CATACAGGCA
GATAGACCTC TACCTATTAA ATCGGCTTCT AGGCGCGCTC CATCTAAATG
TTCTGGCTGT GGTGTACAGG GGCATAAAAT TACGCACTAC CCGAATCGAT
AGAACTACTC ATTTTTATAT AGAAGTCAGA ATTCATAGTG TTTTGATCAT
TTTAAATTTT TATATGGCGG GTGGTGGGCA ACTCGCTTGC GCGGGCAACT
CGCTTACCGA TTACGTTAGG GCTGATATTT ACGTGAAAAT CGTCAAGGGA
TGCAAGACCA AAGTAGTAAA ACCCCGGAAG TCAACAGCAT CCAAGCCCAA
GTCCTTCACG GAGAAACCCC AGCGTCCACA TCACGAGCGA AGGACCACCT
CTAGGCATCG GACGCACCAT CCAATTAGAA GCAGCAAAGC GAAACAGCCC
AAGAAAAAGG TCGGCCCGTC GGCCTTTTCT GCAACGCTGA TCACGGGCAG
CGATCCAACC AACACCCTCC AGAGTGACTA GGGGCGGAAA TTTAAAGGGA
TTAATTTCCA CTCAACCACA AATCACAGTC GTCCCCGGTA TTGTCCTGCA
GAATGCAATT TAAACTCTTC TGCGAATCGC TTGGATTCCC CGCCCCTAGT
CGTAGAGCTT AAAGTATGTC CCTTGTCGAT GCGATGTATC ACAACATATA
AATACTAGCA AGGGATGCCA TGCTTGGAGG ATAGCAACCG ACAACATCAC
ATCAAGCTCT CCCTTCTCTG AACAATAAAC CCCACAG      representing the
```
sequence from nucleotide −1144 to −10 in FIG. 1.

According to a further embodiment the promoter and upstream activating sequences have the following sequence or a functionally equivalent nucleotide sequence:

```
AGATCTGCCC TTATAAATCT CCTAGTCTGA TCGTCGACGC ATTCCGAATA
CGAGGCCTGA TTAATGATTA CATACGCCTC CGGGTAGTAG ACCGAGCAGC
CGAGCCAGTT CAGCGCCTAA AACGCCTTAT ACAATTAAGC AGTTAAAGAA
GTTAGAATCT ACGCTTAAAA AGCTACTTAA AAATCGATCT CGCAGTCCCG
ATTCGCCTAT CAAAACCAGT TTAAATCAAC TGATTAAAGG TGCCGAACGA
GCTATAAATG ATATAACAAT ATTAAAGCAT TAATTAGAGC AATATCAGGC
CGCGCACGAA AGGCAACTTA AAAAGCGAAA GCGCTCTACT AAACAGATTA
CTTTTGAAAA AGGCACATCA GTATTTAAAG CCCGAATCCT TATTAAGCGC
CGAAATCAGG CAGATAAAGC CATACAGGCA CGATCCAACCTC TACCTATTAA
ATCGGCTTCT AGGCGCGCTC CATCTAAATG TTCTGGCTGT GGTGTACAGG
GGCATAAAAT TACGCACTAC CCGAATCGAT AGAACTACTC ATTTTTATAT
AGAAGTCAGA ATTCATAGTG TTTTGATCAT TTTAAATTTT TATATGGCGG
GTGGTGGGCA ACTCGCTTGC GCGGGCAACT CGCTTACCGA TTACGTTAGG
GCTGATATTT ACGTGAAAAT CGTCAAGGGA TGCAAGACCA AAGTAGTAAA
ACCCCGGAAG TCAACAGCAT CCAAGCCCAA GTCCTTCACG GAGAAACCCC
AGCGTCCACA TCACGAGCGA AGGACCACCT CTAGGCATCG GACGCACCAT
CCAATTAGAA GCAGCAAAGC GAAACAGCCC AAGAAAAAGG TCGGCCCGTC
GGCCTTTTCT GCAACGCTGA TCACGGGCAG CGATCCAACC AACACCCTCC
AGAGTGACTA GGGGCGGAAA TTTAAAGGGA TTAATTTCCA CTCAACCACA
AATCACAGTC GTCCCCGGTA TTGTCCTGCA GAATGCAATT TAAACTCTTC
TGCGAATCGC TTGGATTCCC CGCCCCTAGT CGTAGAGCTT AAAGTATGTC
CCTTGTCGAT GCGATGTATC ACAACATATA AATACTAGCA AGGGATGCCA
TGCTTGGAGG ATAGCAACCG ACAACATCAC ATCAAGCTCT CCCTTCTCTG
AACAATAAAC CCCACAGAAG GCATTT   representing the sequence from nucleotide
-1176 to -1 in FIG. 1.
```

According to a further aspect of the present invention the latter sequence may be preceded by the 1.05 kb unsequenced upstream region from pTAKA 17 (position 0 to 1.05 in FIG. 2).

The terminators and polyadenylation sequences may be derived from the same sources as the promoters. Enhancer sequences may also be inserted into the construction.

The expressed product may be accumulated within the cells requiring disruption of the cells to isolate the product. To avoid this further process step and also to minimize the amount of possible degradation of the expressed product within the cells it is preferred that the product is secreted from the cells. For this purpose the gene for the desired product is provided with a preregion ensuring effective direction of the expressed product into the secretory pathway of the cell. This preregion which might be a naturally occuring signal or leader peptide or functional parts thereof or a synthetic sequence providing secretion is generally cleaved from the desired product during secretion leaving the mature product ready for isolation from the culture broth.

The preregion may be derived from genes for secreted proteins from any source of organism.

According to the present invention the preregion may be derived from a glucoamylase or an amylase gene from an Aspergillus species, an amylase gene from a Bacillus species, a lipase or proteinase gene from *Rhizomucor miehei*, the gene for the α-factor from *S. cerevisiae* or the calf prochymosin gene. More preferably the preregion is is derived from the gene for the *Humicola lanuginosa* lipase, *A. oryzae* TAKA amylase, *A. niger* neutral α-amylase, *A. niger* acid-stable α-amylase, *B. licheniformis* α-amylase, the maltogenic amylase from Bacillus NCIB 11837, *B. stearothermophilus* α-amylase or *B. licheniformis* subtilisin. An effective signal sequence is the *A. oryzae* TAKA-amylase signal, the *Rhizomucor miehei* aspartic proteinase signal and the *Rhizomucor miehei* lipase signal.

The TAKA-amylase signal has the following sequence
ATGATGGTCGCGTGGTGGTCTC-
TATTTCTGTACGGCCTTCAGGTCGCGGCACCT
MetMetValAlaTrpTrpSerLeuPh-
eLeuTyrGlyLeuGlnValAlaAlaPro
GCTTTGGCT
AlaLeuAla and the *Humicola lanuginosa* signal peptide has the following sequence
ATGAGGAGGTCCCTTGTGCTGT-
TCTTTGTCTCTGCGTGGACGGCCTTGGCC
MetArgSerSerLeuValLeuPheP-
heValSerAlaTrpThrAlaLeuAla The gene for the desired product functionally linked to promoter and terminator sequences may be incorporated in a vector containing the selection marker or may be placed on a separate vector or plasmid capable of being integrated into the genome of the host strain. As used herein the expression "vector system" includes a single vector or plasmid or two or more vectors or plasmids which together contain the total DNA-information to be integrated into the host genome. Vectors or plasmids may be linear or closed circular molecules. According to a preferred embodiment of the present invention *A. oryzae* is cotransformed with two vectors, one including the selection marker and the other comprising the remaining foreign DNA to be introduced in the host strain, including promoter, the gene for the desired product and transcription terminator and polyadenylation sequences.

Normally the *A. oryzae* transformants are stable and can be cultured in the absence of a selection pressure. If the transformants turn out to be unstable the selection marker may be used for selection during cultivation. The transformed cells are then cultured under a selection pressure corresponding to the marker in question.

The present invention provides for a method for production of high yields of many different polypeptide or protein products in *A. oryzae*. *A oryzae* has for years been used in commercial scale for the production of for instance the TAKA-amylase enzyme and proteolytic enzymes and accordingly fermentation technology for this microorganism is well developed and the microorganism is approved for use in the food industry. The present invention offers the possibility of using *A. oryzae* in the industrial production of high amounts of in principle any polypeptide or protein product. Examples of such products are chymosin or prochymosin and other rennets, proteases, amyloglucosidases, acid stable amylases from Aspergillus, fungal lipases or prokaryotic lipases, and thermostable bacterial and fungal amylases.

The present invention furthermore provides a method for producing high yields of the Humicola lipase by cultivation of transformed Aspergillus strains, and in a preferred embodiment a method for production of the *Humicola lanuginosa* lipase by cultivation of a transformant *A. oryzae* or *A. niger* cell. *A. oryzae* is the most preferred host microorganism.

The present invention is illustrated by means of the production of prochymosin, *Rhizomucor miehei* aspartic proteinase, TAKA-amylase, a lipase from *Rhizomucor miehei* and the Humicola lipase.

The genes for these enzymes were obtained from cDNA libraries or genomic libraries as described in further detail in the following.

The present invention furthermore provides a recombinant Humicola lipase product superior to the native Humicola lipase for having increased thermostability, and increased stability in the presence of alkaline Bacillus proteases.

EXAMPLES

Plasmids used as starting materials in the following examples are as follows:

p285: (ATCC No. 20681)

pCAMG91: Boel et al. EMBO Journal 3 (1984), 1581–1585.

pIC19R: Marsh et al. Gene 32 (1984), 481–485 pSal43: Berse et al. Gene 25 (1983), 109–117 John & Peberdy, Enzyme Microb. Technol. 6 (1984), 386–389.

p3SR2: J. M. Kelly and M. J. Hynes, EMBO Journal 4 (1985), 475–479.

pBR322: Bolivar F. et al., Gene 2 (1977), 95–113.

pBR327: Covarrubias L. et al., Gene 13 (1981), 25–35.

pUC9, pUC13, and pUC19: Vieira et al., Gene 19 (1982), 259–268 and Messing, Meth. in Enzymology 101 (1983), 20–27.

pSP62-K2 and pCDVI-PL: Noma et al. Nature, 319, (1986), 640–646)

The strains used are as follows:

*A. niger**: ATCC 1015, ATCC 10582

*A. oryzae**: ATCC 20423, IFO 4177, ATCC 1011, ATCC 9576, ATCC 14488–11491, ATCC 11601 and ATCC 12892.

*E. coli*: MC1000(Casabadan, M. J. and Cohen, S. N., J.Mol.Biol. 138, 179–207) (NCIB 11956)

Rhizomucor miehei: CBS 370.65

*H. lanugirosa*: DSM 4109

*ArgB mutants of these strains can be prepared as described by F. P. Buxton et al. (Gene 37 (1987) 207–214). An ArgB mutant is defined as a mutant having a defect in the ornithine transcarbamylase gene.

Preparation of Plasmid 285' proC Containing the Prochymosin Gene

Figure 3:
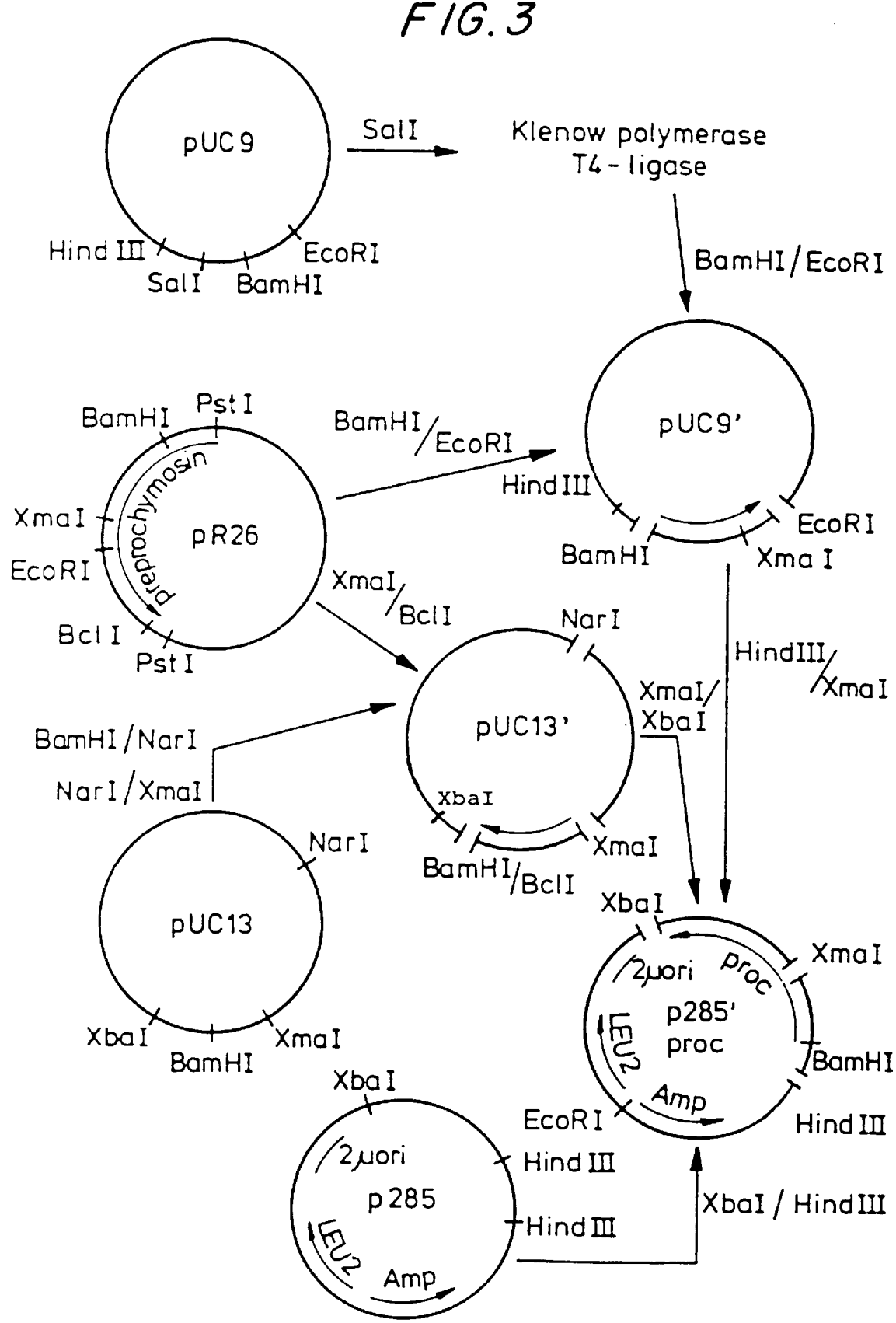
FIG. 3 illustrates the construction of plasmid p285'proC.

The preprochymosin gene was isolated from a calf stomach cDNA library and inserted into the PstI site of pBR322 by G-C tailing (Chirgwin et al., Biochemistry 18 (1979), 5294 and Truelsen et al., Nucleic Acids Res. 6 (1979), 3061) to obtain pR26. pUC9 was cut with SalI and filled out with Klenow polymerase and ligated with T4 ligase. The resulting plasmid was cut with BamHI-EcoRI and the 2.7 kb large fragment was ligated with a 0.47 kb BamHI-EcoRI fragment from pR26 containing the N-terminal end of the prochymosin gene to create pUC9'. pUC9' contains a HindIII site N-terminally of the prochymosin gene. pUC13 was cut with BamHI-NarI and NarI-XmaI and the large respective small fragments were ligated with a 0.64 kb XmaI-BclI fragment of pR26 containing the C-terminal end of the prochymosin gene to obtain plasmid pUC13'. pUC13' contains an XbaI-site C-terminally of the prochymosin gene. A 0.65 kb XmaI-XbaI fragment of pUC13' was ligated with a 0.46 kb HindIII-XmaI fragment of pUC9' and a 11 kb XbaI-HindIII fragment of p285 to create plasmid p285' proC containing the prochymosin gene as illustrated in FIG. 3.

Identification of *Humicola lanuginosa* Lipase (HLL) Amino Acid Sequence

In order to obtain information which allows the construction of a specific oligonucleotide probe, a partial sequence determination was carried out on the purified *Humicola lanuginosa* lipase. The supernatant from a culture broth of *Humicola lanuginosa*, from which mycelia and low molecular weight substances had been removed was subjected to a column chromatography performed by use of DEAE-sepharose (anion exchange chromatography), phenyl sepharose (hydrophobic interaction chromatography) followed by gel filtration on TSK G3000 SW. The sequence determination was performed with a Gas Phase Sequencer (Applied Biosystems Model 470A) as described by Thim, L. et al. (FEBS Lett. 212, 307–312 (1987).

The following N-terminal sequence was found:

```
                        5                  10
Glu—Val—Ser—Gln—Asp—Leu—Phe—Asn—Gln—Phe—
                       15                  20
Asn—Leu—Phe—Ala—Gln—Tyr—Ser—Ala—Ala—Ala—
                       25
Tyr—X—Gly—Lys—Asn—
```

This sequence allows the construction of two specific mixed oligonucleotide probes comprising the sequences from amino acid residue No. 7-No. 11 (Phe-Asn-Gln-Phe-Asn) and amino acid residue No. 13-No. 16 (Phe-Ala-Gln-Tyr), respectively. The screening of a *Humicola lanuginosa* cDNA library by use of HLL-specific oligonucleotide mixtures corresponding to the above sequences is described in example 8.

Example 1

Cloning of the *A. oryzae* TAKA-amylase A Gene

Isolation of a Partial cDNA Clone

From *A. oryzae* Hw 325 grown on potato starch, mRNA was prepared according to Kaplan et al., Biochem. J. 183, (1979) 181–84. A partial cDNA clone containing 1050 bp of the TAKA-amylase gene was obtained by specific priming of mRNA with a 14-mer oligonucleotide mixture:

```
        A   A   A   A
5'GG   TT  TC  TG  TT 3' (NOR-168),
        G   G   G   G
``` complementary to the coding sequence for amino acids 295–299 in TAKA-amylase (Toda et al., Proc. Japan Acad. 58, Ser. B, (1982) 208–12). Cloning procedure was according to Gubler & Hoffmann, Gene 25, (1983) 263–69. Sequencing at the ends and in the middle of the cDNA clone demonstrated presence of sequences corresponding to the amino acid sequence of TAKA-amylase.

Isolation of Genomic Clones

Mycelium from *A oryzae* Hw 325 was harvested and processed for preparation of DNA according to the method used for *A. niger* described by Boel et al. supra. Restriction fragments of 3–10 kb, generated by partial digestion with Sau3A, were ligated with BamHI digested, dephosphorylated pBR322 (New England Biolabs). 50,000 recombinants were screened with oligonucleotide probe NOR-168 (see above), and 7 were found to contain DNA coding for TAKA-amylase. One clone was chosen for further use of the promoter region, having 2.1 kb upstream of the mRNA-start.

Restriction map for plasmid pTAKA 17 is outlined in FIG. 2. pTAKA was deposited with Deutsche Sammlung von Mikroorganismen (DSM), Griesebachstrasse 8, D-3400, Göttingen, on Feb. 23, 1987 and accorded the reference number DSM 4012 DSM being an international depository authorized under the Budapest Treaty of 1977, affords permanence of the deposit and accessibility thereto by the public in accordance with rules 9 and 11, respectively, of the above treaty.

Example 2

Construction of a Rhizomucor miehei cDNA Library

The phycomycete fungus *Rhizomucor miehei* (for a morphological and taxonomical description of this species see: Schipper, M. A. A. On the genera Rhizomucor and Parasitella. In: Studies in mycology, Institute of the Royal Netherlands Academy of Sciences and Letters. No. 17 (1978), 53–71) secretes an acid proteinase (*Rhizomucor miehei* proteinase, in the following abreviated to RMP) which is widely used for clotting of milk in cheese production. In order to obtain cDNA recombinant clones of this protein in *E. coli*, total RNA was extracted from homogenized *R. miehei* mycelium as described by Boel et al. (EMBO J., 3: 1097–1102, 1984) and Chirgwin et al., (Biochemistry (Wash.), 18, 5294–5299, 1979). Poly(A)-containing RNA was obtained by two cycles of affinity chromatography on oligo(dT)-cellulose as described by Aviv and Leder (PNAS, USA, 69, 1408–1412, 1972). Oligo (dT) primed complementary DNA was synthesized and made doublestranded according to Gubler and Hoffman (Gene, 25, 263–269, 1983). Doublestranded cDNA was tailed with dCTP and terminal deoxynucleotidyl transferase as described by Roychoudhury et al. (Nucleic Acids Res, 3, 101–106, 1976). The plasmid pBR327 was linearized with PstI and tailed with dGTP. The oligo(dC) tailed dscDNA was annealed to this oligo(dG) tailed vector as described by Peacock et al. (Biochim.Biophys.Acta, 655, 243–250, 1981) and used to transform a hsdR⁻, M⁺ derivative of *E coli* MC1000 (Casadaban and Cohen, J. Mol.Biol., 138, 179–207, 1980) to generate recombinant clones.

Identification of RMP Specific cDNA Recombinants

A mixture of 16 heptadecamer ligodeoxyribonucleotides

one of which is complementary to RMP mRNA in the region coding for Tyr-Tyr-Phe-Trp-Asp-Ala (Bech and Foltmann, Neth-milk Dairy J. 35: 275–280, 1981) was synthesized on an Applied Biosystems, Inc. DNA synthesizer and purified by polyacrylamide gel electrophoresis. Approximately 10,000 *E. coli* recombinants from the *Rhizomucor miehei* cDNA library ere transferred to Whatman 540 paper filters. The colonies were lysed and immobilized as described by Gergen et al. (Nucleic Acids Res. 7, 2115–2135, 1979). The filters were hybridized with the $^{32}$P-labelled RMP-specific heptadecamer-mixture as described by Boel et al. (EMBO J. 3, 1097–1102, 1984). Hybridization and washing of the filters were done at 40° C., followed by autoradiography for 24 hours with an intensifier screen. Miniprep plasmid DNA was isolated from a hybridizing colony, pRMP1016, by standard procedures (Birnboim and Doly, Nucleic Acids Res., 7, 1513–1523, 1979), and the DNA sequence of the cDNA insert was established by the procedure of Maxam and Gilbert (Methods Enzymol. 65, 499–560, 1980). pRMP1016 was shown to contain part of the 5' untranslated end of the mRNA and then extending through regions encoding a 69 amino acid-long preproregion and 300 amino acids into the mature part of the RMP protein. Since pRMP1016 did not contain any insert corresponding to the complete 3' end of the RMP mRNA, the cDNA library was rescreened with a $^{32}$P nick-translated 3' specific restriction fragment from clone pRMP1016, whereby clone pRMP2931 was isolated. This clone contains part of the 3' untranslated region and an open reading frame with the 270 triplets encoding the carboxyterminal part of the RMP protein. pRMP1016 and pRMP2931, therefore, have extensive overlap, and the combined sequence of the two clones gives the sequence of the *R. miehei* preproRMP cDNA. A total of 1416 nucleotides was sequenced between the G:C tails resulting from the cDNA cloning procedure. The established DNA sequence is shown in FIG. 4*a* and *b* together with the deduced amino acid sequence of a precursor to RMP. In FIG. 4*a* and 4*b* the horizontal line indicates the position of a synthetic oligo mixture used for cDNA library screening. An arrow shows the position where processing occurs in maturation of native RMP. Nucleotides are numbered from the first base in the initiating Met-codon and amino acids are numbered from the first residue in the mature RMP. From this cDNA sequence it can be concluded that RMP is synthesized as a 430 amino acids long precursor with a propeptid of 69 amino acids. A putative signal peptidase processing site (von Heijne, Eur.J.Biochem. 133, 17–21, 1983) in this precursor could be between Ala(−48) and Arg(−47), and the mature RMP will be generated by autoproteolytic cleavage between Glu-1 and Ala(+1). The cDNA deduced amino acid sequence of RMP is in good agreement with the previously published partial amino acid sequence (Bech and Foltmann, Neth-Milk Dairy J. 35: 275–280, 1981).

To facilitate further construction work with the RMP cDNA's, a HindIII linker was inserted at a BanI site just. 3' to the TAA-termination codon identified in clone pRMP2931 as follows: 25 μg pRMP2931 was digested with PstI to obtain the RMPcDNA insert. This insert was purified by 1% agarose gel electrophoresis, electroeluted from the gel, purified by phenol and cloroform extractions and precipitated with NaCl and ethanol. This fragment that encodes the 3' half of the RMP was digested with BanI and the BanI cohesive restriction site ends were filled in with a mixture of the four dNTP's and the Klenow fragment of *E. coli* DNA polymerase. To these filled-in ends were added HindIII linkers in a T4-DNA ligase reaction. The ligation reaction mixture was extracted with phenol and chloroform and the DNA was precipitated with 4M NH$_4^+$ acetate/ethanol. The purified DNA was digested with an excess of HindIII enzyme, and a 380 bp fragment was purified on a 6% polyacrylamide gel. This fragment that contains the 3' end of the RMP open reading frame plus the TAA termination codon was ligated to a HindIII digested and alkaline phosphatase treated pIC19R. The ligation mixture was used to transform competent *E. coli* cells, and transformants were selected on ampicillin containing agar plates. Plasmid DNA was purified from transformants and correct recombinants were identified by restriction endonuclease digestions and agarose gel electrophoresis. From one such correct recombinant, pRMP3', a 210 bp BglII/HindIII fragment was isolated by 6% polyacrylamide gel electrophoresis. This fragment contains the 3' end of RMP cDNA from the BglII site at amino acids 297–299 and extending through the TAA-termination codon to the inserted HindIII linker.

Figure 5:
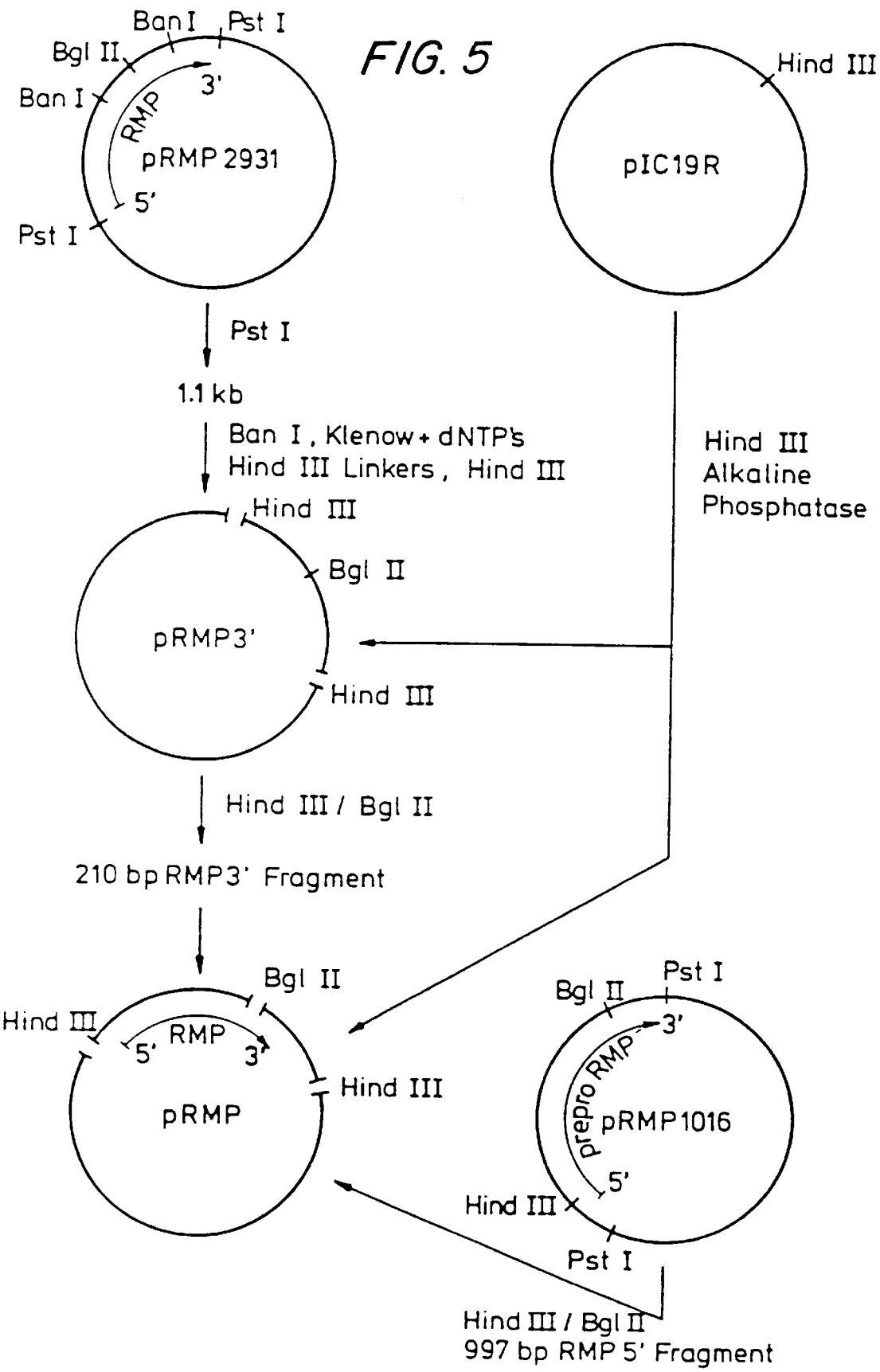
FIG. 5 illustrates the construction of plasmid pRMP

The 5' part of the RMP cDNA was isolated from PRMP 1016 as a 997 bp HindIII/BglII fragment by 1% agarose gel electrophoresis. The HindIII site is located in the RMP-DNA at a position corresponding to the residues −36, −35 in the prosegment. This 997 bp 5' fragment was ligated to the 210 bp 3' fragment in a HindIII digested and phosphatase treated pIC19R. With this ligation mixture, recombinants were obtained from E coli and a correct plasmid, pRMP, with the 5' part of RMP joined to the 3' part was identified by restriction enzyme analysis. The construction of PRMP is illustrated in FIG. 5. pRMP does not encode the RMP preregion and the 5' half of the prosegment.

Figure 6:
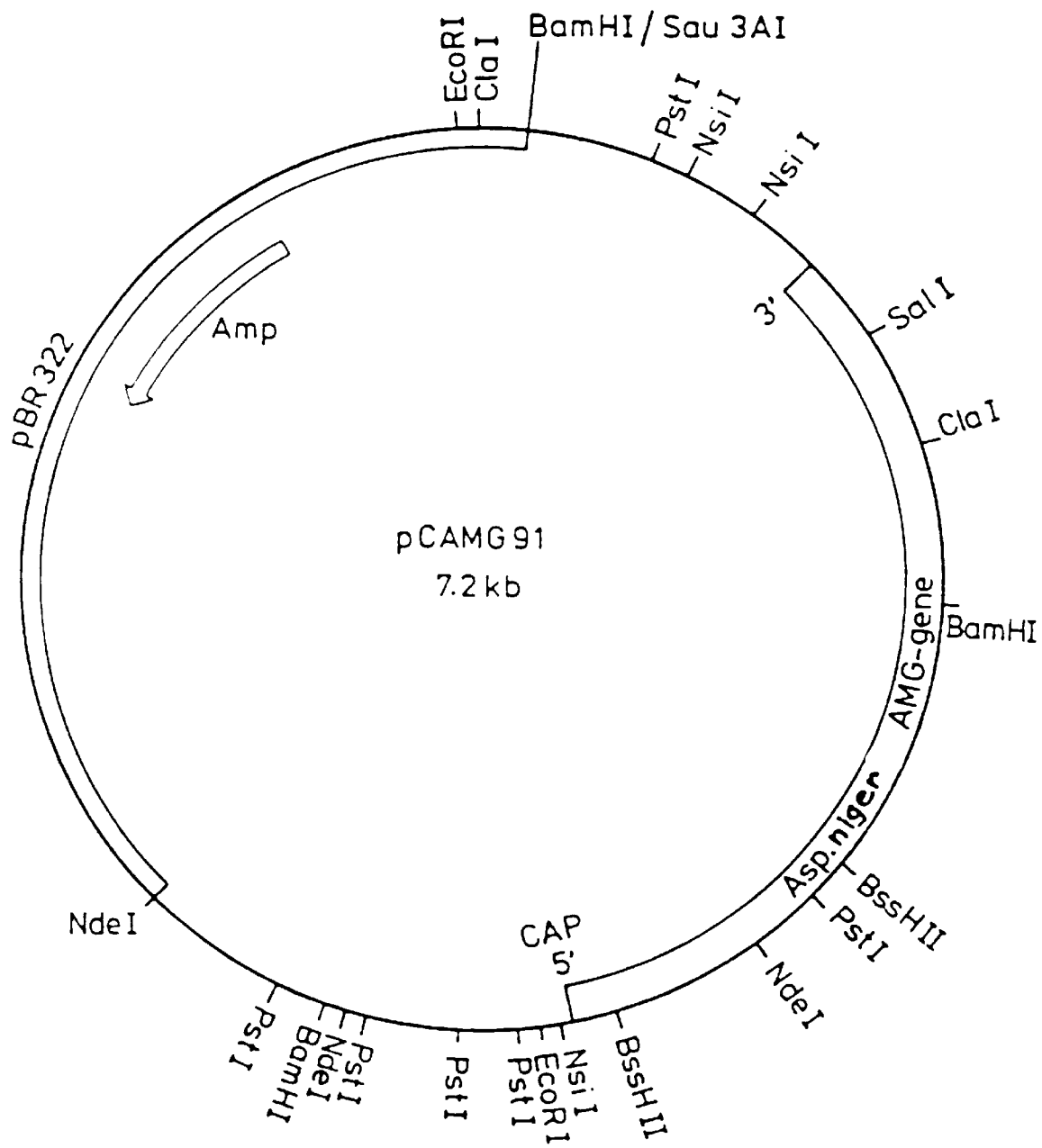
FIG. 6 shows the endonuclease restriction map of plasmid pCAMG91
Figure 7A:
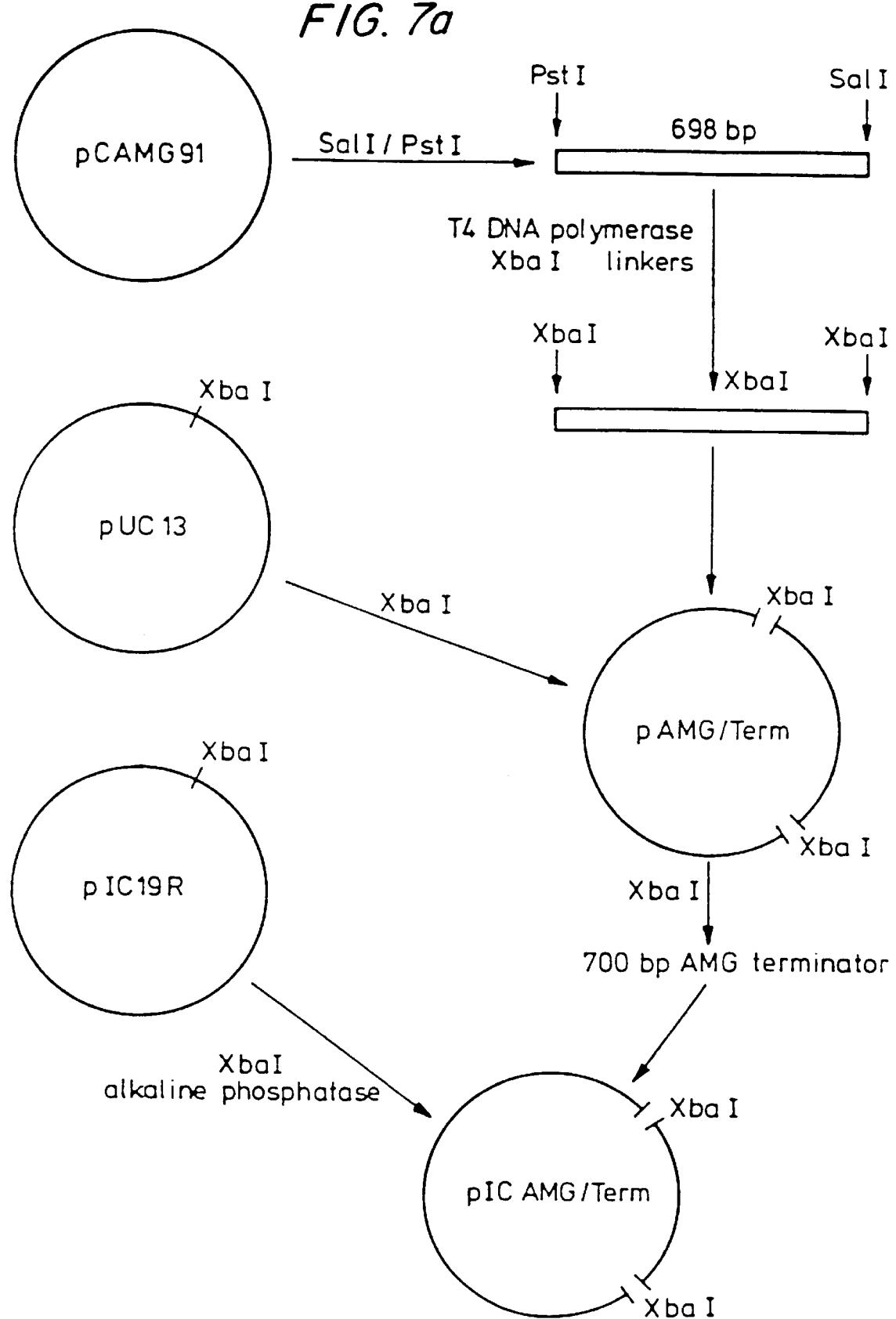
FIG. 7a illustrates the construction of plasmid pICAMG/Term.

Example 3
Construction of an Aspergillus Expression Vector Designed to Obtain Secretion of Active RMP In this example a plasmid was constructed designed to express RMP under control of the glucoamylase promoter, signal and terminator sequences. The glucoamylase promoter and terminator sequences were derived from the glucoamylase genomic gene cloned in vector pCAMG91. The construction of pCAMG91 is described by Boel et al. (EMBO Journal 3 (1984), 1581–1585) and an endonuclease restriction map of plasmid pCAMG91 is shown in FIG. 6.

pCAMG91 was digested with SalI and PstI restriction endonucleases. From such a digest a 698 bp fragment was isolated on an agarose gel. This SalI-PstI fragment contains the region encoding the 140 bp 3' untranslated part of the glucoamylase mRNA plus 540 bp 3' to the poly(A)-addition site. This 3' fragment was treated with T4-DNA polymerase to "blunt end" the restriction sites before the addition of XbaI linkers and digestion with XbaI restriction enzyme. This 3' end of the glucoamylase gene was ligated to pUC13 linearized with XbaI to create plasmid pAMG/Term containing the glucoamylase gene poly(A) addition region. The construction of pAMG/Term is illustrated in FIG. 7a.

The 3' end of the A. niger glucoamylase gene was obtained as a 700 bp XbaI fragment from pAMG/Term. This terminator fragment was ligated to XbaI digested and phosphatase treated pIC19R. With this ligation mixture recombinants were obtained from E. coli and a correct plasmid, pICAMG/Term, with the 5' end of the teminator fragment facing the HindIII site of the multiple cloning site of the pIC19R vector was identified by restriction enzyme analysis. The construction of pICAMG/Term is illustrated in FIG. 7a. From pICAMG/Term the glucoamylase terminator (AMG terminator) region was isolated as a 750 bp HindIII/ClaI restriction fragment by 1% agarose gel electrophoresis. From pCAMG91 the glucoamylase promoter (AMG promoter) was isolated together with regions encoding the glucoamylase signal peptide, hexapeptide-prosegment and the pBR322 ampicillin resistence gene (Amp) as a 3.5 kb ClaI/BssHII fragment by 1% agarose gel electrophoresis. A synthetic BssHII/HindIII linker was prepared from two synthetic 31' mer oligonucleotides synthesized on an Applied Biosystems Inc. DNA-synthesizer. The synthetic linker has the following structure:

```
     R   V   S   K   Q   S   E   S   K   D
    CGCGTAAGTAAGCAGAGCGAGAGCAAGGATA
        ATTCATTCGTCTCGCTCTCGTTCCTATTCGA
```

This linker was used in a ligation reaction with the 3.5 kb glucoamylase promoter containing fragment and the 750 bp glucoamylase terminator containing fragment. The ligation mixture was used to transform E. coli and a correct recombinant, p673, was identified by restriction endonuclease digestion. The isolated p673 is a HindIII cloning vector, into which an appropriate HindIII cDNA fragment can be inserted between the glucoamylase hexapeptide prosegment and the glucoamylase transcription terminator region. The inserted cDNA will be under transcriptional control by the glucoamylase promoter, and secretion of the translated fusion product will be directed by the glucoamylase signal peptide plus the glucoamylase hexapeptide prosegment. p 673 was digested with HindIII, treated with alkaline phosphatase and ligated with a 1.2 kb HindIII fragment purified from a digest of pRMP.

Figure 7B:
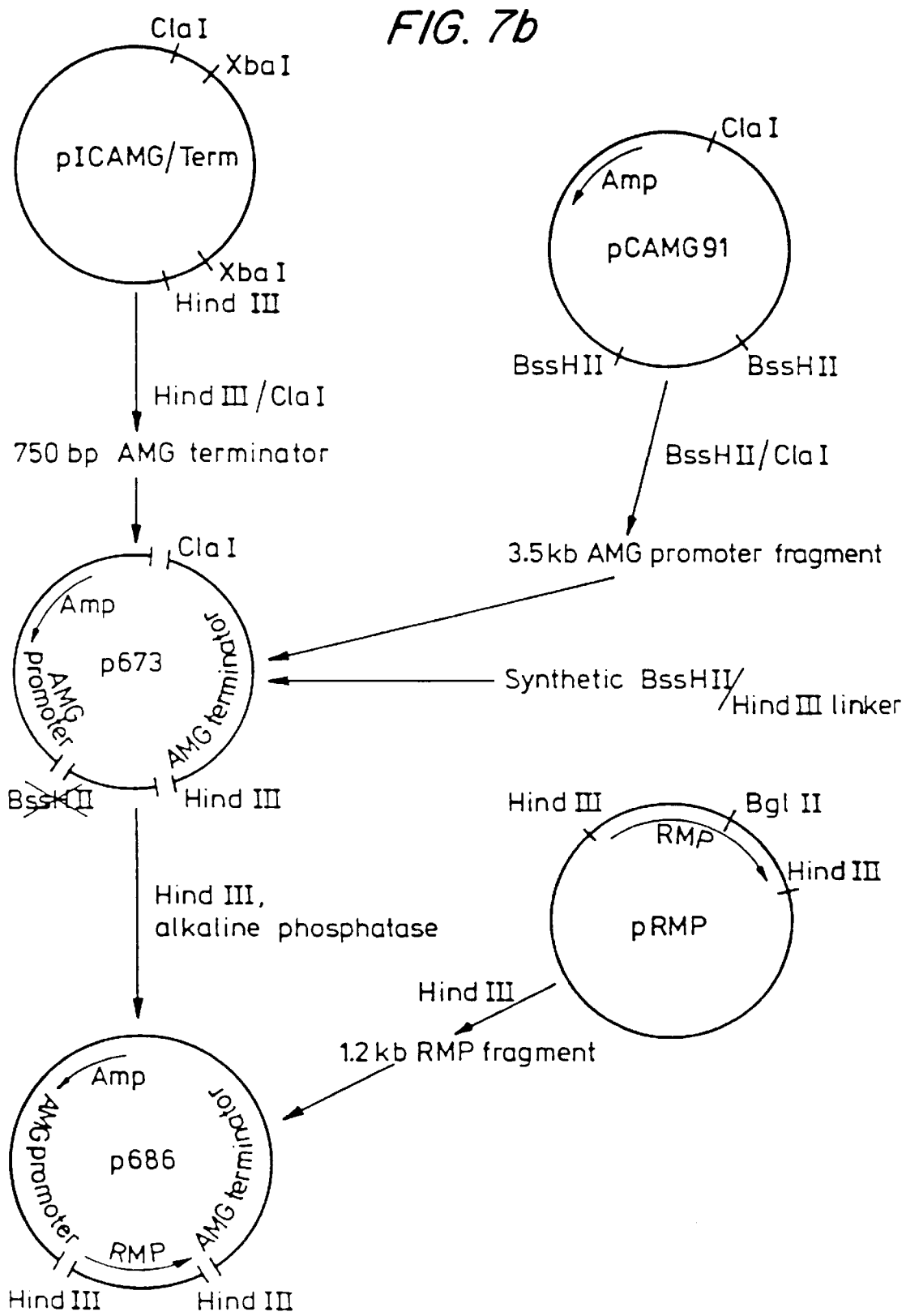
FIG. 7b illustrates the construction of plasmid p686

The ligation mixture was used to transform E. coli and a recombinant, p686, with the RMP cDNA inserted in the correct orientation to achieve RMP expression was isolated and characterized by restriction endonuclease digestions. p686 encodes a RMP precursor with the following structure: glucoamylase signal peptide, glucoamylase hexapropeptide, amino acids −45 to −1 of the propeptide from RMP, 361 amino acids of mature RMP. The construction of p686 is illustrated in FIG. 7b.

Example 4

In a preferable embodiment of the present invention the open reading frame of preproRMP should be inserted in an expression plasmid under control of the promoter from the glucoamylase gene from A. niger or the TAKA-amylase gene from A. oryzae. To do this, a BamHI restriction endonuclease site was inserted just 5' to the initiating methionine codon of the signal peptide of preproRMP by the following steps. pRMP1016 was digested with DdeI which cuts in the cDNA at a position corresponding to amino acid residues Ser(−66) and Gln(−65), and with HindIII which cuts in the cDNA at a position corresponding to amino acid residues Lys(−36) and Leu(−35). The resulting 89 bp DdeI/HindIII fragment was purified on a 8% polyacrylamide gel, electroeluted and ethanolprecipitated after phenol and CHCl₃ extractions. A synthetic DNA fragment with the following sequence was synthesized as two oligonucleotides on an Applied Biosystems Inc. DNA synthesizer:

```
           M  L  F  S
    GATCCACCATGCTGTTCTC      oligo 697/698
        GTGGTACGACAAGGAAGT
```

Figure 8:
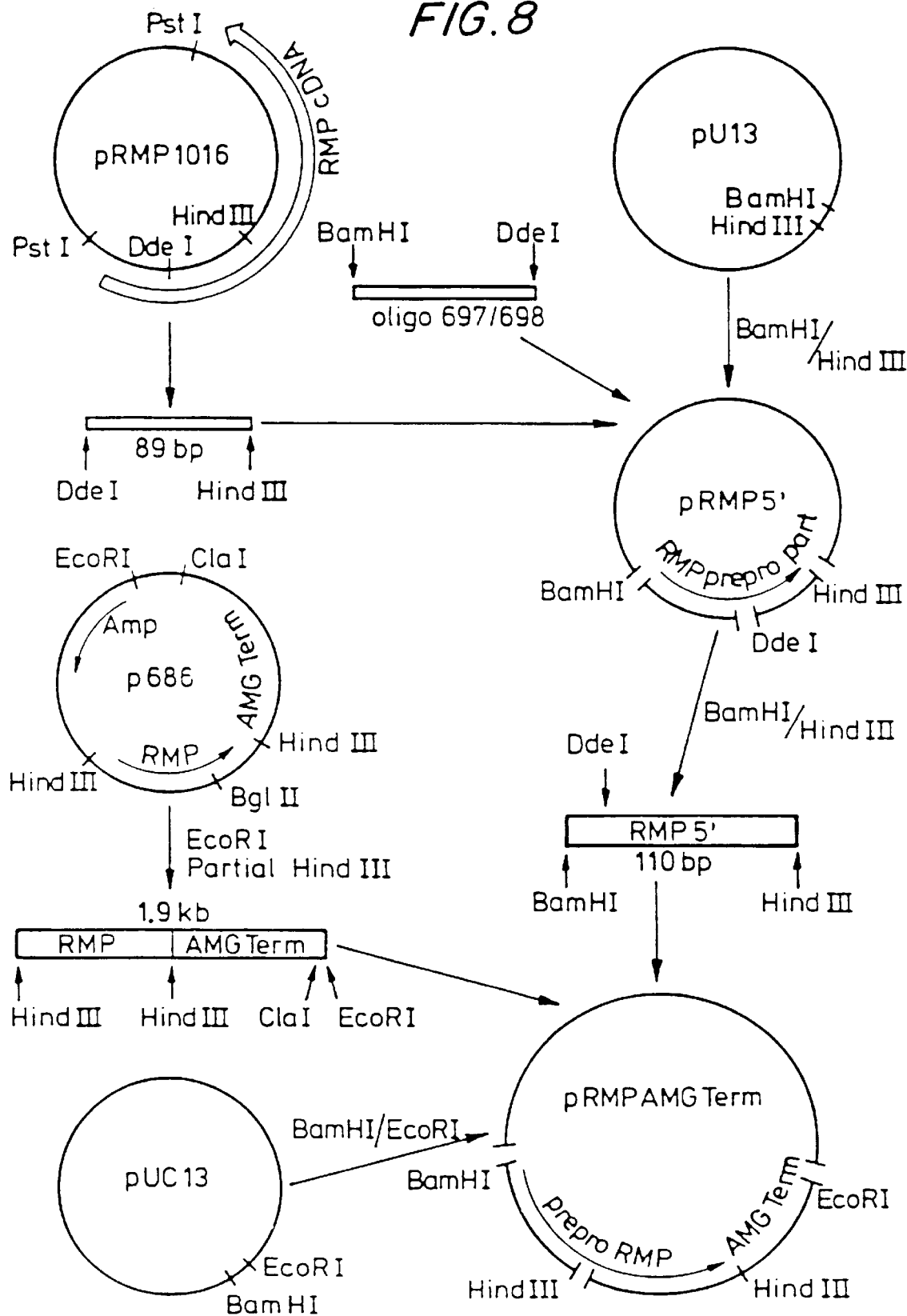
FIG. 8 illustrates the construction of plasmid pRMPAMGTerm.

This fragment has a BamHI cohesive end 5' to the initiating Met-codon and a DdeI cohesive end in the 3' end. The two oligonucleotides were kinased with ATP and T4 polynucleotide kinase, annealed to each other and then ligated to the 89 bp DdeI/HindIII RMP fragment purified from pRMP1016 in a BamHI/HindIII digested pUC13 vector. The ligation mixture was used to transform E. coli cells, and correct recombinants were identified by restriction enzyme digestions on miniprep purified plasmids. Correct recombinant plasmids were sequenced to verify the sequence of the oligonucleotides used. One such correct plasmid pRMP5' was digested with BamHI and HindIII, and a 110 bp BamHI/HindIII fragment with the initiating Met codon, RMP signal peptide and part of the RMP prosegment was purified by 10% polyacrylamide gel electrophoresis. The fragment was electroeluted, phenol and CHCl₃ extracted and ethanol precipitated. The rest of the RMP open reading frame and the AMG terminator sequences were obtained from plasmid p686 after digestion with EcoRI and partial HindIII digestion. Hereby a 1.9 kb fragment was released and this fragment was purified by agarose gel electrophoresis, electroelution, phenol and CHCl₃ extraction before ethanol precipitation. This 1.9 kb fragment was ligated to the 110 bp BamHI/HindIII fragment from pRMP5' in a pUC13 vector that had been digested with BamHI and EcoRI. The ligation mixture was used to transform E. coli cells and correct recombinants were identified by restriction enzyme digestions on miniprep purified plasmids. One such correct recombinant was pRMPAMGTerm. The construction of pRMPAMGTerm is illustrated in FIG. 8.

Figure 9A:
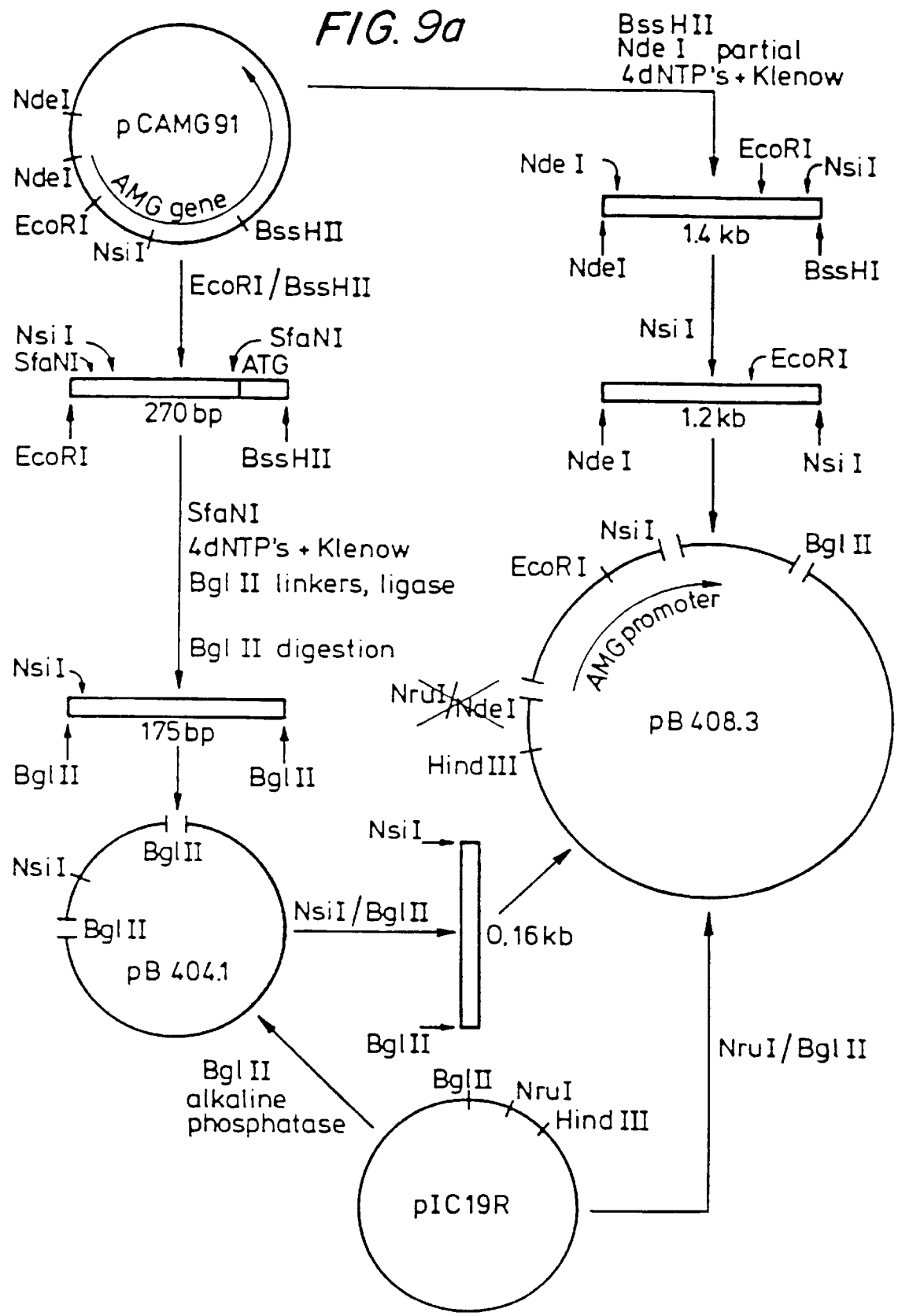
FIG. 9a illustrates the construction of plasmid pB408.3.
Figure 9B:
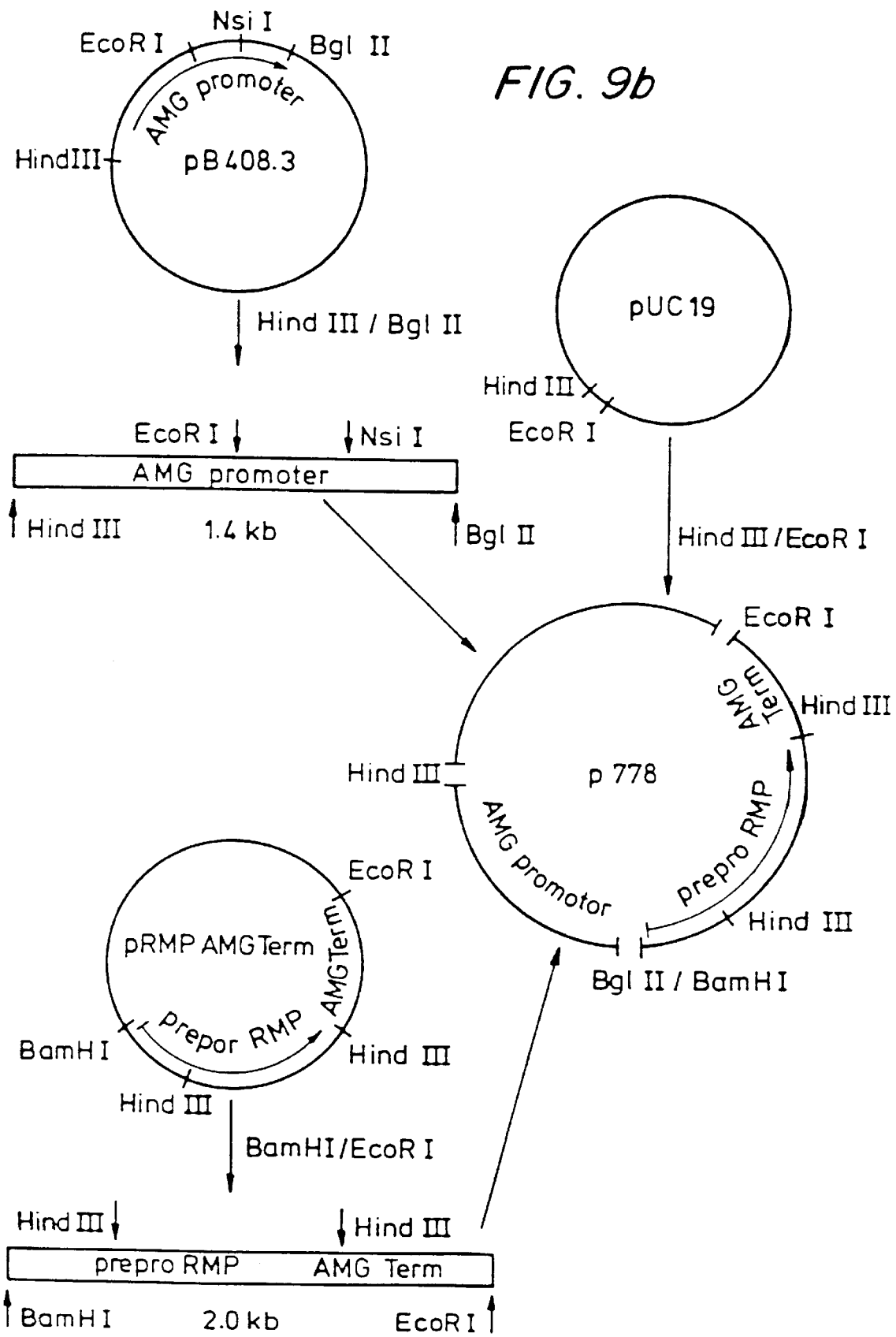
FIG. 9b illustrates the construction of plasmid p778.

Example 5
Construction of an Aspergillus Expression Vector Designed to Obtain Secretion of Active RMP in *A. oryzae* by Means of the *Aspergillus niger* Glucoamylase Promoter The glucoamylase promoter was isolated as follows. 25 μg of pCAMG91 was digested with EcoRI and BssHII restriction endonucleases. After this double digestion a 270 bp DNA fragment could be isolated by agarose gel electrophoresis. This fragment covers part of the promoter region, the 5' untranslated region and the signal peptide of the glucoamylase gene (AMG gene). After electroelution of the DNA from the agarose gel, the fragment was purified by phenol and CHCl₃ extractions before ethanol precipitation. The 270 bp long fragment was then digested with SfaNI. This enzyme has a cleavage site just 5' to the initiating ATG methionine codon of the glucoamylase gene. After complete digestion, the DNA was treated with the large fragment (Klenow) of DNA polymerase I and all four dNTP's to generate blunt ends on the DNA. To this DNA was added BglII linkers with DNA ligase, and the DNA was digested with an excess of BglII restriction enzyme. After separation of the DNA fragments on a 10% polyacrylamide gel, a 175 bp BglII fragment could be isolated by electroelution. This fragment has a BglII linker inserted in a position corresponding to the SfaNI restriction site just 5' to the initiating methionine codon. This piece of DNA was ligated to a BglII digested alkaline phosphatase treated pIC19R vector, and the ligation mixture was used to transform *E. coli* cells. Among the resulting transformants correct plasmids were identified by restriction enzyme digestions on miniprep plasmids. One such correct plasmid pB404.1 was digested with NsiI and BglII to liberate a 0.16 kb fragment which contained the 5' untranslated region of the glucoamylase gene together with approximately 100 bp of the 3' part of the promoter region. This fragment was purified by polyacrylamid gel electrophoresis, electroeluted, phenol and CHCl₃ extracted and ethanol precipitated. To join this fragment to the remaining part of the glucoamylase promoter region from pCAMG91, the following steps were carried out. 25 μg pCAMG91 was digested with BssHII, and then further partially digested with NdeI. After filling in the fragment ends with all four dNTP's and the Klenow fragment of DNA polymerase, a 1.4 kb DNA fragment was isolated on a 1% agarose gel. This fragment contained all of the promoter region together with the 5' untranslated region and the signal peptide encoding region. The fragment was electroeluted, phenol and CHCl₃ extracted and ethanol precipitated to concentrate the DNA. After digestion with NsiI, the DNA was run on a 1% agarose gel, and a 1.2 kb NdeI-NsiI fragment was isolated by electroelution. This DNA had been given a blunt end at the NdeI site in a previous reaction and it was now ligated to the 0.16 kb NsiI-BglII fragment from pB401.1 in a NruI-BglII digested pIC19R vector. The ligation mixture was used to transform *E. coli* cells, and among the resulting transforments correct recombinants were identified by restriction enzyme digestions of miniprep plasmids. One such correct recombinant, pB408.3 was digested with HindIII and BglII, and the glucoamylase (AMG) promoter was isolated as a 1.4 kb fragment on a 1% agarose gel. The fragment was electroeluted, phenol and CHCl₃ extracted and ethanol precipitated. This glucoamylase promoter fragment was then ligated to a 2.0 BamHI-EcoRI fragment from pRMPAMGTerm (see example 4) in a HindIII-EcoRI digested pUC19 vector. The ligation mixture was used to transform *E. coli* cells, and among the resulting transformants correct recombinants were identified by restriction enzyme digestions of miniprep plasmids. One such correct recombinant p778 was grown in large scale for isolation of recombinant plasmid and the plasmid preparation was purified by CsCl/Ethidium bromide centrifugation. This plasmid directs the synthesis of RMP under control of the glucoamylase promoter and terminator sequences. The construction of p408.3 is illustrated in FIG. 9a and the construction of p778 is illustrated in FIG. 9b.

Figure 10:
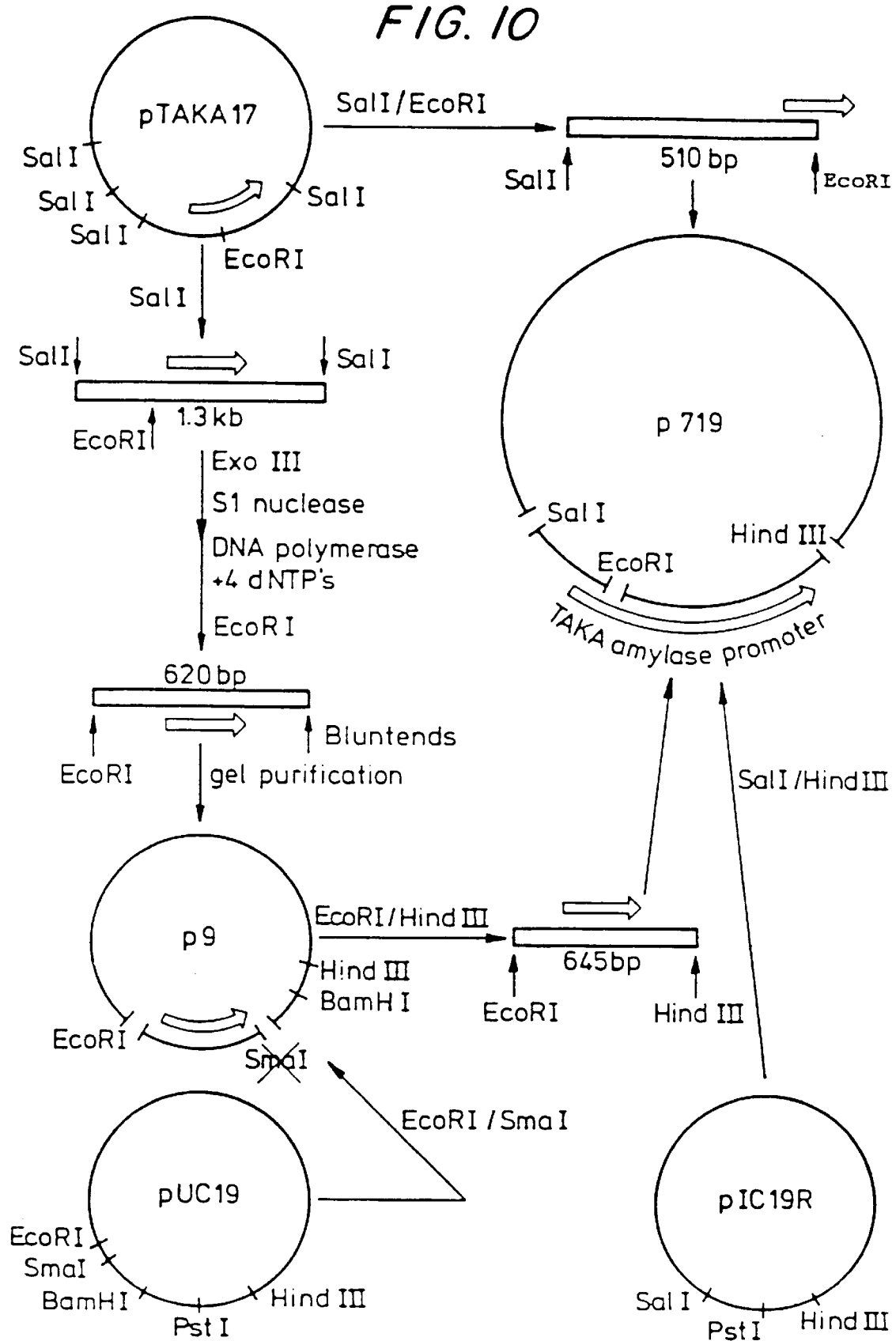
FIG. 10 illustrates the construction of plasmid p719.

Example 6
Construction of an Aspergillus Expression Vector Designed to Obtain Secretion of Active RMP by means of the *Aspergillus oryzae* TAKA-amylase Promoter 50 μg of plasmid pTAKA17 (see example 1) which contains the *Aspergillus oryzae* TAKA-amylase genomic gene was digested with SalI. This enzyme has a restriction site in the genomic DNA at a position corresponding to amino acid residue 26 of the mature TAKA-amylase. Another SalI restriction site is located app. 1300 nucleotides upstream to this position that is in the 5' end of the upstream promoter region. After SalI digestion this 1300 bp promoter containing fragment was purified by agarose gel electrophoresis and the DNA was purified by phenol and CHCl₃ extractions and ethanol recipitated. The DNA was then dissolved in exonuclease III buffer and digested with exonuclease III according to Henikoff, S. (Gene, 28: 351–359, 1984). The reaction was stopped to obtain approximately 130 bp deletions in each end of the DNA. The deletion of app. 130 bp from the SalI site of the coding region of the TAKA-amylase gene in this way gives the opportunity to introduce multiple cloning site linkers just upstream of the initiating methionine codon. The exonuclease III treated DNA was digested with S1 nuclease according to Henikoff, S. (Gene, 28: 351–359, 1984) and precipitated with ethanol after phenol and CHCl₃ extractions. Repair of the S1 nuclease treated DNA to obtain ligatable blunt ends were done with all four dNTP's and the Klenow fragment of DNA polymerase I according to Henikoff, S., (Gene, 28: 351–359, 1984). The DNA was digested with EcoRI which cuts once in the 1300 bp SalI fragment to generate two groups of fragments. One group was about 380 bp long and represented upstream regions while the other group was about 620 bp long and contained the promoter region. These groups of EcoRI digestion products were separated on an agarose gel, and the app. 620 bp long DNA fragments were electroeluted and ligated to an EcoRI/SmaI digested pUC19 vector. The ligation mixture was used to transform competent *E. coli* cells, and miniprep plasmid DNA was isolated from the recombinants. These deletion mutants were characterized by restriction enzyme digestions to identify plasmids with deletion end points just 5' to the initiating methionine codon. A few candidates with the desired characteristics were sequenced and a mutant (p9) that had 9 bp deleted 5' to the A in the ATG-methionine codon was chosen for further constructions. p9 was digested with EcoRI and HindIII, and a 645 bp TAKA-amylase promoter containing fragment was isolated by agarose gel electrophoresis, phenol and CHCl₃ extracted and precipitated with ethanol. pTAKA17 was digested with SalI and EcoRI and a 510 bp fragment containing the TAKA-amylase-promoter upstream regions was isolated by agarose gel electrophoresis, phenol and CHCl₃ extracted and precipitated with ethanol. These two promoter regions were ligated to each other and to a pIC19R vector, that had been digested with SalI and HindIII. The ligation mixture was used to transform *E. coli* cells, and correct recombinants were identified by restriction enzyme digestion of plasmids extracted as minipreps. In one such recombinant p719 the TAKA-amylase promoter region from *Aspergillus oryzae* is found as a 1.1 kb portable fragment that can be excised by a number of various restriction enzyme digests. The construction of p719 is illustrated in FIG. 10.

Figure 11:
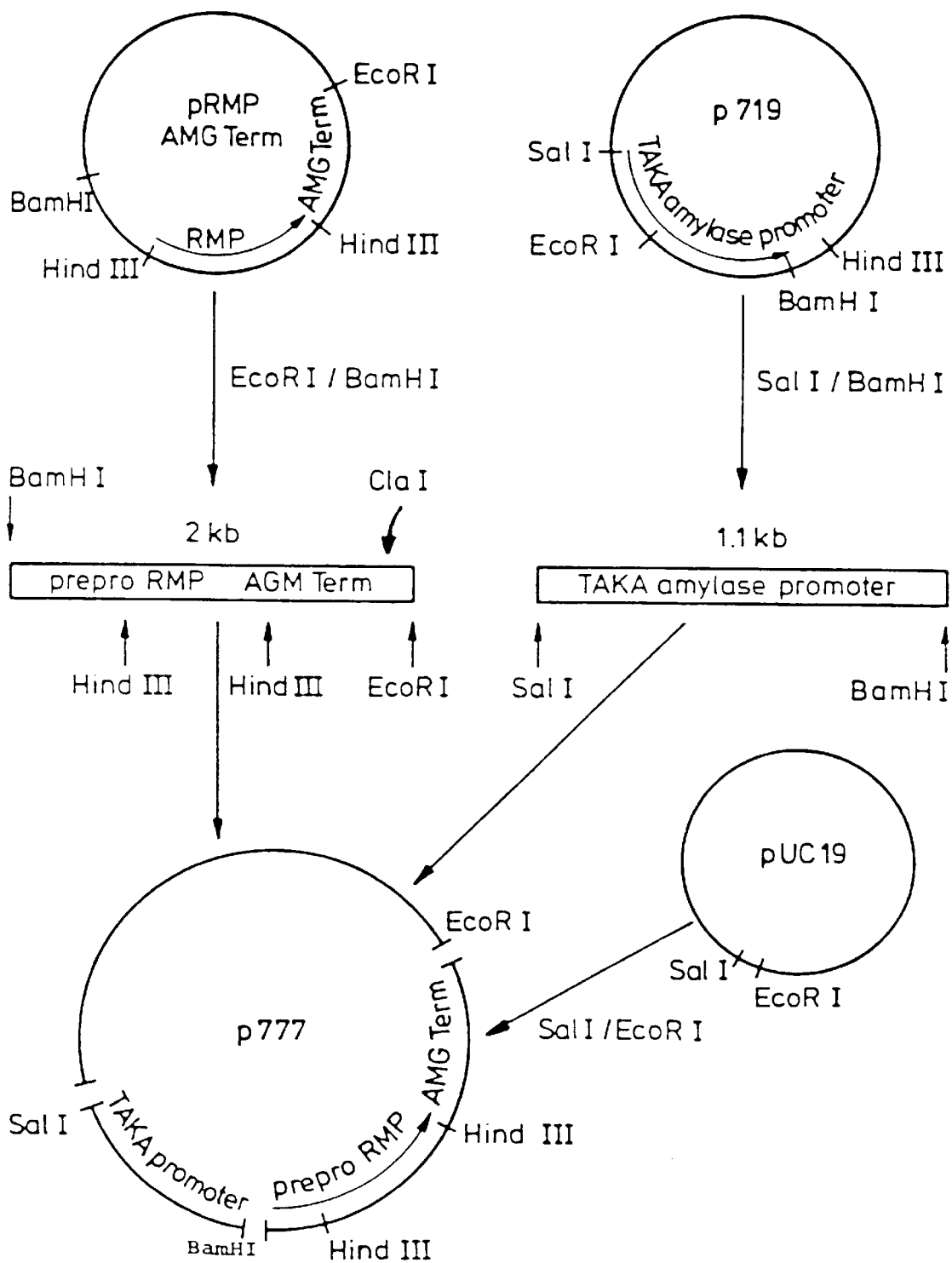
FIG. 11 illustrates the construction of plasmid p777.

From pRMPAMGTerm the preproRMP open reading frame and glucoamylase terminator region (AMGTerm) was isolated as a 2 kb fragment after digestion with BamHI and EcoRI. This fragment was purified by agarose gel electrophoresis, phenol and CHCl₃ extractions and then concentrated by ethanol precipitation. The promoter from the TAKA-amylase from *A. oryzae* was now isolated as a 1.1 kb fragment obtained after digestion of p719 with SalI and BamHI. This fragment was purified by agarose gel electrophoresis, phenol and CHCl₃ extractions and then ethanol precipitated. The 1.1 kb promoter fragment was ligated to the 2 kb BamHI/EcoRI fragment from pRMPAM-GTerm in a pUC19 vector, that had been digested with SalI and EcoRI. The ligation mixture was used to transform *E. coli* cells and among the resulting transformants correct recombinants were identified with restriction enzyme digestion of miniprep plasmids. One such correct recombinant p777 was grown in large scale for the isolation of recombinant plasmid, and the plasmid preparation was purified by CsCl/Ethidium bromide centrifugation. The construction of p777 is illustrated in FIG. 11.

Example 7
Construction of an Aspergillus Expression Vector Designed to Obtain Secretion of the *Rhizomucor miehei* Lipase under Control of the *Aspergillus oryzae* TAKA-amylase Promoter Construction and Identification of a Lipase cDNA Clone in *E. coli*

In order to obtain information which allows the construction of a specific oligonucleotide probe, a partial sequence determination was carried out on the purified *Rhizomucor miehei* lipase (Moskowitz, G. J. et al., J.Agric. Food Chem., 25 (1977), 1146–1150). In the following text the abbreviation RML is used for the *Rhizomucor miehei* lipase. The supernatant from a culture broth of *Rhizomucor miehei*, from which mycelia and low molecular weight substances had been removed was subjected to anion exchange chromatography. The main lipolytic fraction from the column was desalted and ultrafiltrated prior to lyophilization. The lyophilized powder was then subjected to an affinity chromatography. The pooled lipase fractions from the column were desalted and concentrated by ultrafiltration. This concentrate was then subjected to a hydrophobic interaction chromatography (HIC) and the lipase from the HIC-purification was used for amino acid sequence determination. The sequence determination was carried out both on the native enzyme (N-terminal sequence) and on selected fragments obtained after proteolytic digestion of the lipase with *Armillaria mellea* protease. The sequence determination was performed with a Gas Phase Sequencer (Applied Biosystems Model 470A) as described by Thim, L. et al. (FEBS Lett. 1987, in press).

RML was digested with *Armillaria mellea* protease as described by Moody et al. (FEBS Lett. 172 (1984), 142–148) with the only exception that the enzyme to substrate ration was 1:40 (mol:mol). Fragments obtained were separated by HPLC and the UV-absorption was monitored at 280 nm and 214 nm. In order to identify suitable fragments for the construction of oligonucleotide probes, only peptides which showed a high ratio between 280 nm and 214 nm were sequenced as these fragments contain Trp and/or Tyr.

The following N-terminal sequence was found by use of the native RML;

```
                  5                        10
Ser—Ile—Asp—Gly—Gly—Ile—Arg—Ala—Ala—Thr—
                 15                        20
Ser—Gln—Glu—Ile—Asn—Glu—Leu—Thr—Tyr—Tyr—
                 25
Thr—X—Leu—(Ser)—(Ala)—.
```

One of the fragments isolated from the proteolytic digest had the sequence of: Arg-Thr-Val-Ile-Pro-Gly-Ala-Thr-Trp-Asp-X-Ile-His, and this fragment was used for the synthesis of a specific oligonucleotide probe.

The *Rhizomucor miehei* cDNA library from example 2 constructed for isolation of the aspartic proteinase (RMP) recombinants from this organism was also used for identification of lipase specific recombinants. A mixture of oligonucleotides was synthesized on an Applied Biosystems Inc. DNA-synthesizer. The mixture which has the structure:

```
    A
5'  TCCCANGTNGCNCC 3' 430/431
    G
``` was complementary to RML mRNA in a region encoding the amino acids Gly-Ala-Thr-Trp-Asp. This pentapeptide was identified as a segment of an amino acid sequence obtained from proteolytic fragments of the purified RML protein (see above).

The *Rhizomucor miehei* cDNA library was screened with the ³²P-kinased lipase oligonucleotide mixture as described for screening with the RMP specific mixture. Hybridization and initial washing of the filters were done at 43° C. After autoradiography, the filters were washed at 47° C. Colonies that showed strong hybridization were isolated and the inserted cDNAs in the corresponding plasmids were sequenced to identify RML specific recombinants. Two such recombinants p353.7 and p353.16 had inserts of about 1.2 kb. The DNA sequence obtained from these two recombinants starts in the middle of the signal peptide (see FIG. 12) and extends through to the poly A tail. In this region one long open reading frame could be identified. Since the two recombinants did not include sequence for the 5' part of a signal peptide with its initiating methionine codon a synthetic oligonucleotide (584)

5' CGAGAGGGGATGAGGGGTGG 3' 584 was synthesized. This oligonucleotide 584 is complementary to the RML in mRNA in a region encoding the amino acid sequence Pro-Pro-Leu-Ile-Pro-Ser-Arg found in the propeptide region (see FIG. 12). After the oligo 584 had been kinased to high specific activity with T4 polynucleotide kinase and ³²P-ATP, it was used in a primer extension reaction on *Rhizomucor miehei* mRNA with AMV reverse transcriptase according to published procedures (Boel, E. et al., PNAS, USA, 80, 2866–2869, 1983). The primer extension reaction products were electrophoresed on a 10% polyacrylamide/urea gel and two cDNA products were resolved. These two cDNAs, one 150 nucleotides long and the other 160 nucleotides long were both electroeluted and sequenced by the chemical degradation procedure for DNA sequencing. Both cDNAs gave readable sequence extending from the primer region and up to a position 9 nucleotides 5' to an initiating methionine codon. The sequence confirmed the sequence obtained from the lipase recombinant cDNA plasmids. The lengths of the two primer extension cDNA products indicate that the 5' end (CAP-site) of the lipase mRNA will be located app. 5 or 15 nucleotides 5' to the first A nucleotide shown in FIG. 12. A microheterogeniety in the location of the 5' end of mRNA's from fungi is very common. By combining the sequence obtained from the two cloned cDNAs p353.7 and p353.16 with the sequence from the primer extension analysis, the amino acid sequence of a RML precursor can be established. The DNA-sequence and the corresponding amino acid sequence of the RML precursor is shown in FIG. 12. In FIG. 12 the horizontal lines indicate the positions of synthetic oligos used for cDNA synthesis and for cDNA library screening. An arrow shows the position where processing occurs in maturation of native RML. Nucleotides are numbered from the first base in the initiating Met-codon and amino acids are numbered from the first residue in the mature native RML. The RML is encoded by an open reading frame extending from an initiating Met codon and then through 363 codons before a stop codon is reached. In this precursor the first 24 amino acid residues would constitute a typical hydrophobic signal peptide. According to the productive rules of von Heijne (Eur.J.Biochem. 133, 17–21, 1983), the signal peptide would be cleaved from the following propeptide by a signal peptidase cleavage between the Ala- and Val residues at position −71 and −70, respectively.

Since the N-terminal amino acid sequence analysis of purified RML obtained from the culture supernatant from *Rhizomucor miehei* identified Ser-Ile-Asp-Gly-Gly-Ile-Arg as the N-terminus of the active RML enzyme, the propeptide of the RML precursor consisted of the next 70 amino acid residues in the precursor. Beginning with this N-terminal Ser residue, the mature RML extends through 269 residues before reaching a termination codon. In this mature 29500 dalton enzyme a lipase substrate binding site is located around residue Ser(144) which is conserved in a number of lipases. In the 3' end of the RML mRNA 104 nucleotides were localized as an untranslated region between the TAA stop codon and the poly(A) tail. 23 nucleotides 5' to this poly(A) tail a repetitive structure consisting of 7 AT basepairs was found while no typical eukaryotic polyadenylation signal could be identified.

In a preferred embodiment of the present invention a number of changes was carried out on the RML cDNA. These changes involved removal of the G:C tails added to the cDNA during cloning and addition of restriction endonuclease sites 5' and 3' to the open reading frame. A number of convenient restriction sites were also introduced in the signal peptide and propeptide regions of the cDNA.

p353.16 was digested with FnuDII and a 880 bp DNA fragment (the 3' end of RML cDNA) was isolated by agarose gel electrophoresis. The fragment was electroeluted, phenol and CHCl₃ extracted and precipitated with ethanol.

This 3' end of RML cDNA was then ligated to a pUC19 vector that had been digested with SmaI and treated with alkaline phosphatase. The ligation reaction was used to transform competent *E. coli* cells and among the generated transformants correct recombinants were identified by restriction enzyme digestion of miniprep plasmids. One such appropriate recombinant p4352 was digested with BanII and HindIII and a 0.69 kb fragment was isolated by agarose gel electrophoresis. The fragment was electroeluted, phenol and CHCl₃ extracted and precipitated with ethanol. This fragment of RML cDNA now had a major part of the pUC19 multiple cloning site joined to its 3' untranslated region.

Figure 13A:
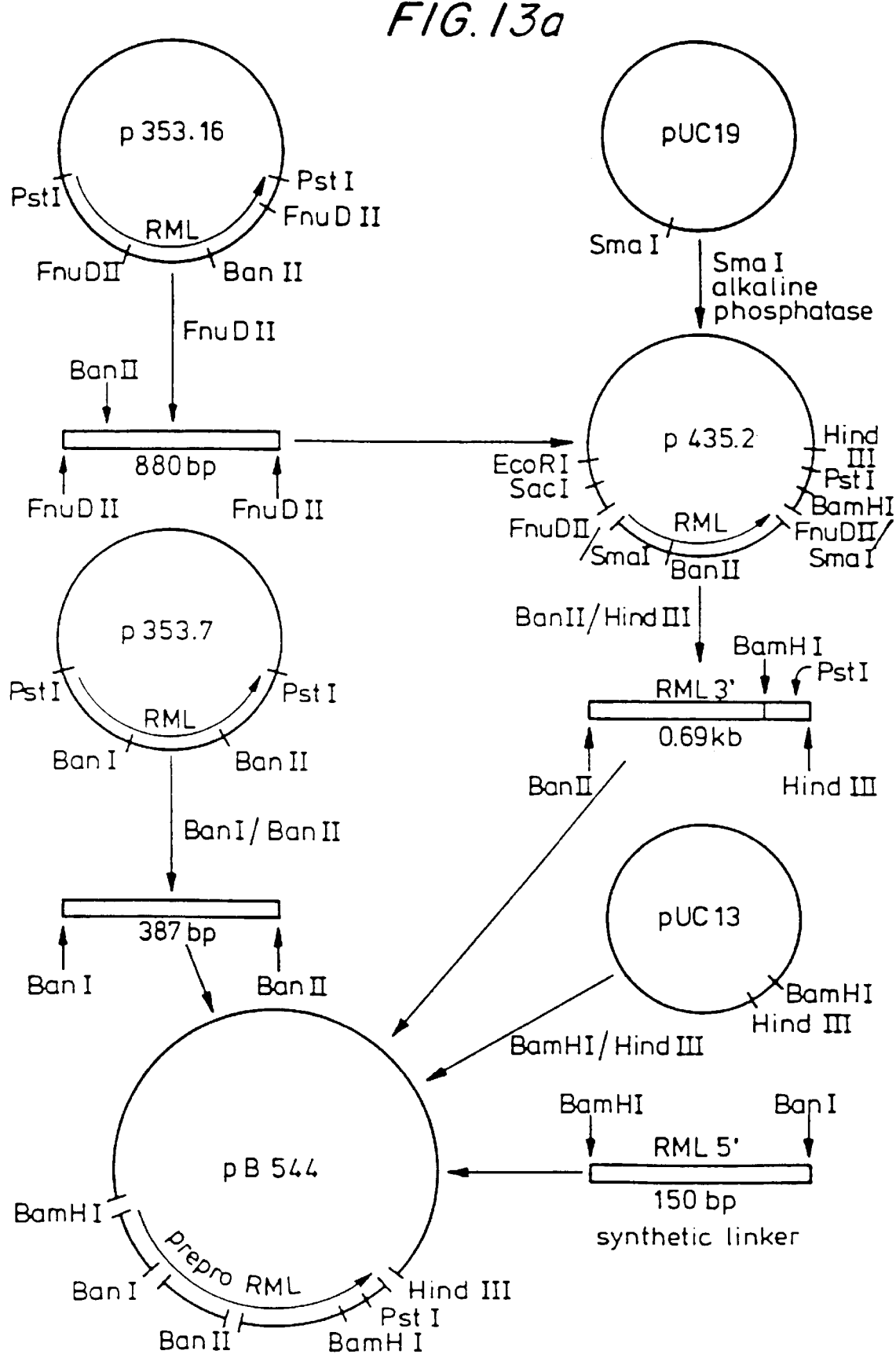
FIG. 13a illustrates the construction of plasmid plasmid pB544.
Figure 13B:
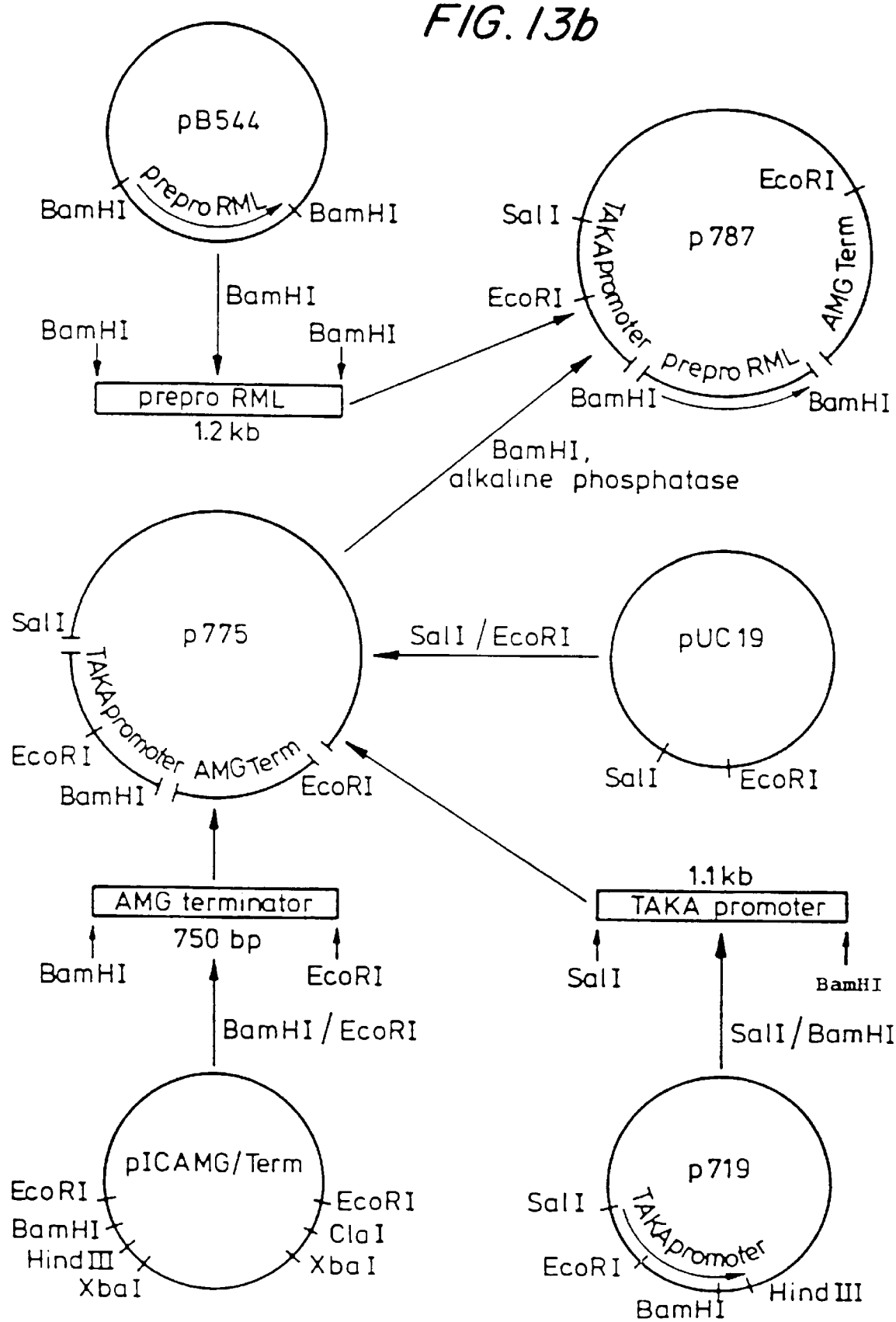
FIG. 13b illustrates the construction of plasmid p787.

The 5' end of the RML cDNA was redesigned using synthetic oligonucleotides in order to introduce convenient restriction sites. The DNA-sequence of the synthetic fragment (RML 5') is shown in FIG. 14. The position of introduced restriction sites and the joining sites of the individually synthesized oligonucleotides are indicated by horizontal viz. vertical/horizontal lines. The resulting fragment (RML 5') was purified as a 150 bp fragment on a 2% agarose gel, electroeluted, phenol and CHCl₃ extracted and precipitated with ethanol before further ligation reactions.

p353.7 was digested with BanI and BanII and a 387 bp RML fragment was purified by 10% polyacrylamide gel electrohporesis. The fragment was electroeluted, phenol and CHCl₃ extracted before ethanol precipitation and then ligated to the synthetic RML 5' fragment and the 0.69 kb BanII/HindIII fragment from p435.2 in a BamHI/HindIII digested pUC13 vector. The ligation reaction was used to transform competent *E. coli* cells and among the resulting transformants correct recombinants were identified by restriction enzyme digestions on miniprep plasmids. In one such correct recombinant, pB544, the synthetic part was sequenced to confirm the expected structure. The construction of pB544 is illustrated in FIG. 13a. From pB544 the prepro RML cDNA was isolated as a 1.2 kb BamHI fragment by agarose gel electrophoresis. An expression vector based on the promoter from the *Aspergillus oryzae* TAKA-amylase gene and the terminator from the *Aspergillus niger* glucoamylase gene was prepared as follows. p719 (see example 6) was digested with SalI and BamHI. The resulting 1.1 kb TAKA-amylase promoter fragment was purified by agarose gel electrophoresis. pICAMG/Term (see example 3) was digested with BamHI and EcoRI. The resulting 0.75 kb glucoamylase terminator fragment was purified by agarose gel electrophoresis. After phenol and CHCl₃ extractions these two fragments were ethanol precipitated and ligated to a SalI/EcoRI digested pUC19 vector. The ligation reaction was used to transform *E. coli* cells and among the resulting transformants correct recombinants were identified by restriction enzyme digestion of miniprep plasmids. One such correct recombinant p775 was digested with BamHI and treated with alkaline phosphatase. The 1.2 kb BamHI RML prepro cDNA fragment from pB544 was ligated to this p775 vector and transformed into *E. coli*. A recombinant p787 with the RML prepro cDNA inserted in the correct orientation between promoter and terminator was identified by restriction enzyme. digestions on miniprep plasmids extracted from *E. coli* transformants. p787 plasmid DNA was grown in large scale and the plasmid preparation was purified by CsCl/Ethidium bromide centrifugation. The construction of p787 is illustrated in FIG. 13b.

Example 8

Construction of a *Humicola lanuginosa* cDNA Library in *E. coli*

Total RNA was extracted from homogenized *H. lanuginosa* mycelium using methods as described by Boel et al. (EMBO J., 3: 1097–1102, 1984) and Chirgwin et al., (Biochemistry (Wash.), 18, 5294–5299, 1979). Poly(A)-containing RNA was obtained by two cycles of affinity chromatography on oligo(dT)-cellulose as described by Aviv and Leder (PNAS, USA, 69, 1408–1412, 1972). cDNA was synthesized with the use of methods described by Okayama and Berg (Molec.Cell.Biol., 2: 161–170, 1982), and with the vectors pSP62-K2 and pCDVI-PL described by Noma et al. (Nature, 319: 640–646, 1986). The synthesized cDNA was transformed into a hsdR⁻, M⁺ derivative of *E. coli* MC1000 (Casadaban and Cohen J. Mol.Biol., 138, 179–207, 1980) to generate recombinant clones.

Identification of *Humicola lanuginosa* Lipase (HLL) Specific cDNA Recombinants

A mixture of 32 pentadecamer oligodeoxyribonucleotides

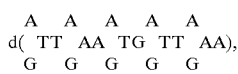

one of which is complementary to HLL mRNA in the region coding for Phe-Asn-Gln-Phe-Asn was synthesized on an Applied Biosystems, Inc. DNA synthesizer and purified by polyacrylamide gel electrophoresis. Approximately 10,000 *E. coli* recombinants from the *Humicola lanuginosa* cDNA library were transferred to Whatman 540 paper filters. The colonies were lysed and immobilized as described by Gergen et al. (Nucleic Acids Res. 7, 2115–2135, 1979). The filters were hybridized with the $^{32}$P-labelled HLL-specific pentadecamer-mixture as described by Boel et al. (EMBO J. 3, 1097–1102, 1984). Hybridization and washing of the filters were done at 37° C. and 43° C. respectively, followed by autoradiography for 24 hours with an intensifier screen. Miniprep plasmid DNA was isolated from two hybridizing colonies, pHLL 702,3 and pHLL 702,4 by standard procedures (Birnboim and Doly, Nucleic Acids Res., 7, 1513–1523, 1979), and the DNA sequence of the cDNA insert was established by the procedure of Maxam and Gilbert (Methods Enzymol. 65, 499–560, 1980).

Figure 16:
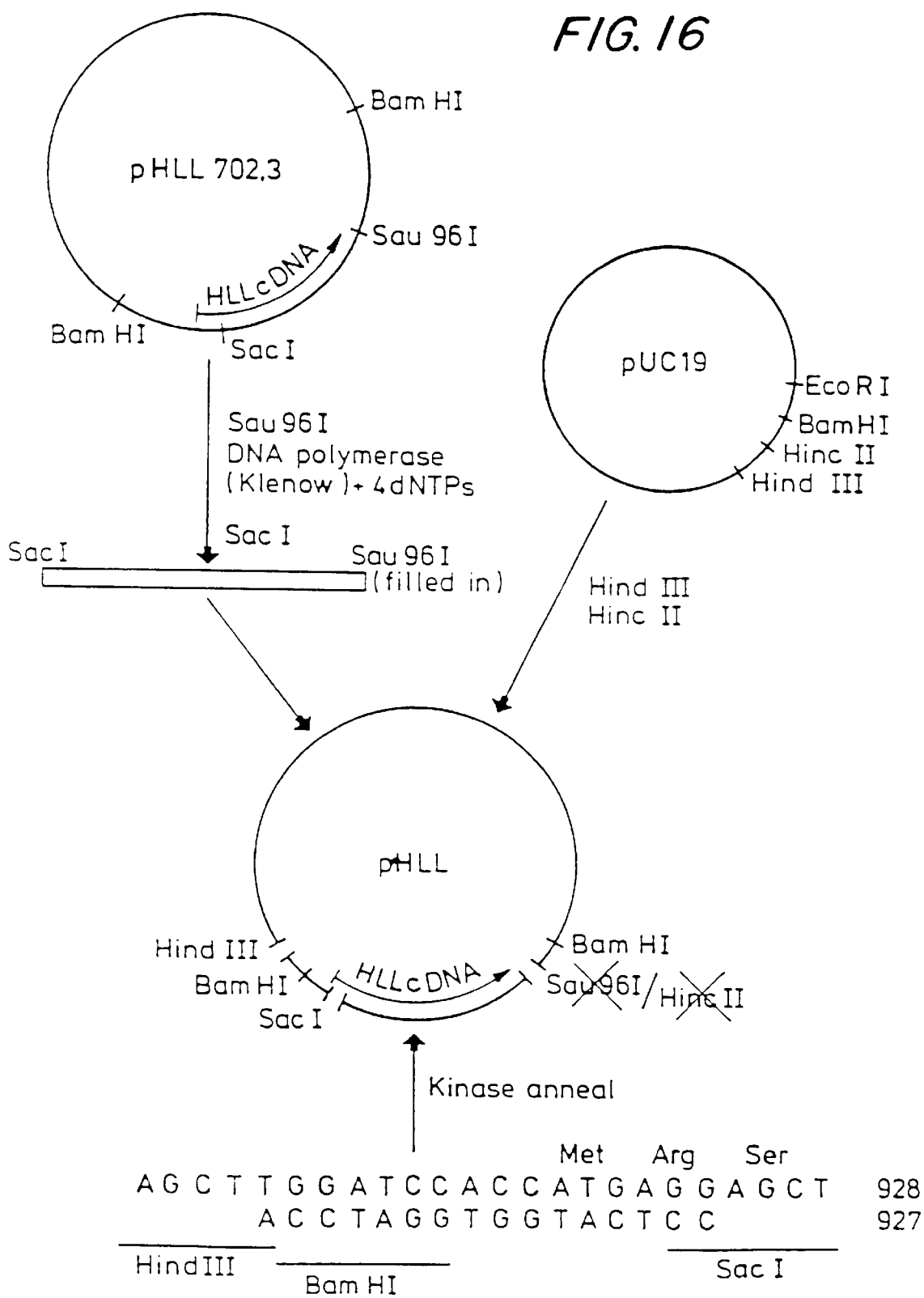
FIG. 16 illustrates the construction of plasmid pHLL.

To facilitate further construction work with the HLL cDNA, DNA sequences containing unique restriction sites were added to the 5' and the 3' ends of the cDNA as follows. pHLL 702,3 was digested with Sau96I which digests HLL cDNA in the 3' untranslated region and the resulting ends were filled in with *E. coli* DNA polymerase (Klenow fragment) and the four dNTPs. This DNA was subsequentially digested with SacI which cuts the HLL cDNA once just 3' to the initiating methionine codon. The resulting 0.9 kb HLL cDNA fragment was purified by agarose gel electrophoresis, electroeluted and made ready for ligation reactions. As a 5' adaptor two oligonucleotides, 927 and 928, were synthesized. The sequence of the adaptor is shown in FIG. 16. This adaptor was designed to add a HindIII and a BamHI site just 5' to the initiating Met codon of HLL cDNA. The two oligos were kinased with ATP and T$_4$ polynucleotide kinase, annealed to each other and ligated to the purified 0.9 kb FLL cDNA sequence in a pUC19 vector that had been digested with HindIII and HincII and purified on a 0.7% agarose gel. The resulting plasmid pHLL carried the HLL cDNA as a portable 0.9 kb BamHI fragment. The construction of pHLL is shown in FIG. 16.

Figure 17:
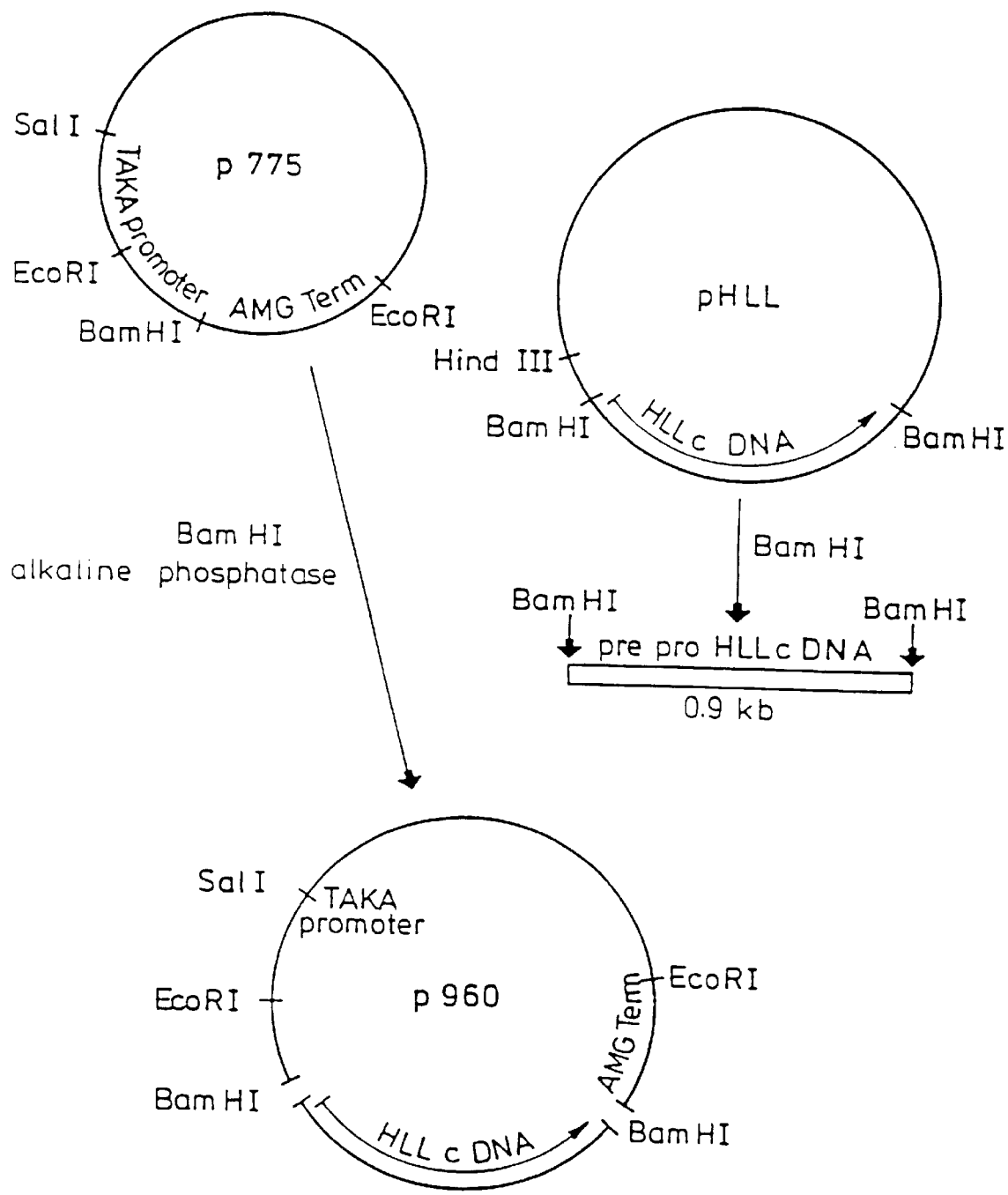
FIG. 17 illustrates the construction of plasmid p960.

After BamHI digestion and purification of the 0.9 kb HLL cDNA fragment on an agarose gel it was ligated to BamHI digested and phosphatased p775 to generate p960 in which HLL cDNA is under transcriptional control of the TAKA promotor from *Aspergillus oryzae* and the AMG terminator from *Aspergillus niger*. The construction of p960 is shown in FIG. 17.

The construction of p775 is described in Example 7. p775 contains the TAKA promoter and AMG terminator and has a unique BamHI site as a cloning site.

FIG. 18*a* and *b* gives the sequence of prepro HLL cDNA with its deduced amino acid sequence. Nucleotides are numbered from the first base in the cloned cDNA. From this cDNA sequence it can be concluded that HLL is synthesized as a 291 amino acid residue long precursor with a signal peptide of 17 residues, and a short propeptide of 5 residues. The putative signal peptidase processing site (von Heijne, Eur.J.Biochem. 133, 17–21, 1983) is indicated with an arrow pointing to the peptide bond between an Ala and a Ser residue. The amino terminus of the mature enzyme as identified by amino terminal amino acid sequencing is indicated.

Amino Acid Composition of *Humicola lanuginosa* (HLL)

Amino acid analysis was carried out by means of a Beckman Amino Acid Analyzer (Model JL1 MB) on samples (40 μg) previously hydrolyzed in sealed ampoules in 6M HCl or 4M methanesulfonic acid at 110° C. for 24, 48 and 96 hours. Half-cystine was determined as S-β-(4-pyridylethyl)-cysteine after reduction by tributylphosphin followed by coupling with 4-vinylpyridine. All chemicals were of highest purity.

The results are shown in the following table and compared to the amino acid composition determined from cDNA sequencing.

| Amino Acid | Found | Nearest integer | cDNA |
|---|---|---|---|
| Ala | 20.85 | 21 | 21 |
| Arq | 14.42 | 14 | 14 |
| Asn | 36.91 | 37 | 19 |
| Asp | | | 19 |
| Cys$^c$ | 5.54 | 6 | 6 |
| Gln | 18.20 | 18 | 6 |
| Glu | | | 12 |
| Gly | 27.51 | 28 | 28 |
| His | 5.94 | 6 | 6 |
| Ile$^b$ | 14.99 | 15 | 16 |
| Leu | 20.06 | 20 | 20 |
| Lys | 7.05 | 7 | 7 |
| Met | 0 | 0 | 0 |
| Phe | 14.80 | 15 | 15 |
| Pro | 11.90 | 12 | 12 |
| Ser$^a$ | 16.76 | 17 | 17 |
| Thr$^a$ | 18.46 | 18 | 19 |
| Trp | 3.58 | 4 | 4 |
| Tyr | 9.84 | 10 | 10 |
| Val$^b$ | 18.24 | 18 | 18 |

$^a$extrapolated value to zero hydrolysis time
$^b$extrapolated value to infinite hydrolysis time
$^c$determined as S-β-(4-pyridylethyl)-cysteine.

Example 9

Transformation of *Aspergillus oryzae* or *Aspergillus niger* (General Procedure)

100 ml of YPD (Sherman et al., Methods in Yeast Genetics, Cold Spring Harbor Laboratory, 1981) was inoculated with spores of *A. oryzae*, *A. niger* or argB mutants hereof and incubated with shaking at 37° C. for about 2 days. The mycelium was harvested by filtration through miracloth and washed with 200 ml of 0.6M MgSO$_4$. The mycelium was suspended in 15 ml of 1.2M MgSO$_4$, 10 mM NaH$_2$PO$_4$, pH=5.8. The suspension was cooled on ice and 1 ml of buffer containing 120 mg of Novozym® 234, batch 1687 was added. After 5 min., 1 ml of 12 mg/ml BSA (Sigma type H25) was added and incubation with gentle agitation continued for 1.5–2.5 hours at 37° C. until a large number of protoplasts was visible in a sample inspected under the microscope.

The suspension was filtered through miracloth, the filtrate transferred to a sterile tube and overlayered with 5 ml of 0.6M sorbitol, 100 mM Tris-HCl, pH=7.0. Centrifugation was performed for 15 min. at 1000 g and the protoplasts were collected from the top of the MgSO$_4$ cushion. 2 volumes of STC (1.2M sorbitol, 10 mM Tris-HCl pH=7.5, 10 mM CaCl$_2$) were added to the protoplast suspension and the mixture was centrifugated for 5 min. at 1000 g. The protoplast pellet was resuspended in 3 ml of STC and repelleted. This was repeated. Finally the protoplasts were resuspended in 0.2–1 ml of STC.

100 μl of protoplast suspension was mixed with 5–25 μg of the appropriate DNA in 10 μl of STC. Protoplasts from the argB strains were mixed with pSal43 DNA (an *A. nidulans* argB gene carrying plasmid) and protoplasts from the argB⁺ strains were mixed with p3SR2 (an *A. nidulans* amdS gene carrying plasmid). The mixture was left at room temperature for 25 min. 0.2 ml of 60% PEG 4000 (BDH 29576), 10 mM CaCl$_2$ and 10 mM Tris-HCl pH=7.5 was added and carefully mixed (twice) and finally 0.85 ml of the same solution was added and carefully mixed. The mixture was left at room temperature. for 25 min., spun at 2500 g for 15 min. and the pellet was resuspended in 2 ml of 1.2M sorbitol. After one more sedimentation the protoplasts were spread on the appropriate plates. Protoplasts from the argB strains transformed with pSal43 were spread on minimal plates (Cove, Biochem.Biophys.Acta. 113 (1966) 51–56) with glucose and urea as carbon and nitrogen sources respectively, and containing 1.2M sorbitol for osmotic stabilization. Protoplasts from the argB⁺ strains transformed with p3SR2 were spread on minimal plates (Cove, Biochim.Biophys.Acta 113 (1966) 51–56) containing 1.0M sucrose, pH=7.0, 10 mM acetamide as nitrogen source and 20 mM CsCl to inhibit background growth. After incubation for 4–7 days at 37° C. spores were picked, suspended in sterile water and spread for single colonies. This procedure was repeated and spores of a single colony after the second reisolation were stored as a defined transformant.

Example 10

Expression of TAKA-amylase in a Wild Type *A. oryzae* Strain pTAKA17 was transformed into *A. oryzae* IFO 4177 by cotransformation with p3SR2 containing the amdS gene from *A. nidulans* as described in example 9. Protoplasts prepared as described were incubated with a mixture of equal amounts of pTAKA 17 and p3SR2, approximately 5 µg of each were used. 9 transformants which could use acetamide as sole nitrogen source were reisolated twice. After growth on YPD (Sherman et al, 1981) for three days culture supernatants were analysed by SDS-PAGE. The gels were stained with coomassie brilliant blue R. The best transformants produced 10–20 times more amylase than untransformed IFO 4177. One transformant was selected for further studies and grown in a 2 liter Kieler fermentor on 4% soy bean meal and supplied with glucose during growth. The culture was heavily agitated during fermentation. Under these conditions IFO 4177 gave about 1 g/l and the transformant about 12 g/l of amylase determined as enzyme activity. Enzyme activity was measured as ability to degrade starch (Cereal Chemistry, 16 (1939), 712–723). The starch used was Merck Amylum solubile erg B.6 and the assay was performed at pH 4.7 and at 37° C. No external beta-amylase was added.

Example 11

Expression of RMP in *A. oryzae* p777 from example 6 or p778 from example 5 was transformed into IFO-4177 by cotransformation with p3SR2 by the procedure described in example 9. Transformants were selected and reisolated as described in example 9.

Transformants were grown for three days in YPD and supernatants were analysed by SDS-PAGE followed by Western blotting and ELISA. The supernatants from transformants of both p777 and p778 contained from 50–150 mg/l of protein reacting with RMP antibody. The proteinase was overglycosylated compared to the *R. miehei* produced proteinase. Two forms were seen of which one is presumed to be a proform and the other the processed mature proteinase. Two transformants of p778 and three transformants of p777 were grown in a fermentor in the same way as the TAKA-amylase transformants described above. The two transformants of p778 gave approximately 0.2 g/l and 0.4 g/l and the three transformants of p777 gave approximately 0.5 g/l, 2.4 g/l and 3.3 g/l of RMP determined as milk clotting activity by the Kunitz method (Kunitz M., Jour.Gen.Physiol. 18 (1935), 459–466), assuming that the specific activity of the recombinant RMP is the same as that of the *Rhizomucor miehei* enzyme. (This has later been confirmed) SDS-PAGE and SDS-PAGE followed by Western-blotting and ELISA revealed that only one form of RMP was present when culturing in a larger scale. The RMP was overglycosylated also under these growth conditions. The protein amount seen on gels correlated well with the amounts predicted from enzyme activity.

RMP was purified from the culture supernatant by affinity chromatography and size exclusion chromatography.

The N-terminal sequence of the purified recombinant RMP was determined by use of a Gas Phase Sequencer as described by Thim et al. (FEBS Lett, 1987 in press).

Two forms of the recombinant RMP were found indicating that the processing in the N-terminal end was heterogeneous. One form had the N-terminal sequence of: Ala-Asp-Gly-Ser-Val-Asp-Thr-Pro-Gly-Tyr- and the other form had the N-terminal sequence of: Gly-Ser-Val-Asp-Thr-Pro-Gly-Tyr-Tyr-Asp-. Such heterogeneous processing at the N-terminus has also been described for native RMP from *Mucor miehei* (Paquet, D. et al., Neth.Milk.Dairy J., 35 (1981), 358–360). As the heterogenous processing of the recombinant RMP correlates well with that of native RMP, *A. oryzae* has according to the present invention been shown to be able to process recombinant RMP in the correct region.

Example 12

Construction of an Expression Unit for the Production of Prochymosin in *A. oryzae*

The construction contains the prochymosin gene immediately preceded by the signal peptide sequence from the *A. oryzae* TAKA-amylase gene under control of the *A. oryzae* TAKA-amylase promoter. The construct further contains the terminator from the *A. niger* glucoamylase gene plus an *E. coli* replicon.

An approximately 430 bp BamHI/XmaI fragment from p285' proC (FIG. 3) and a synthetic oligomer of the following sequence

```
AATTCCAGCTGCCGCGGCCGAGATCACCAG
    GGTCGACGGCGCCGGCTCTAGTGGTCCTAG
``` were inserted into EcoRI-XmaI cut pUC19 plasmid giving plasmid pToC50a.

pToC50a was cut with EcoRI-SacII and the large fragment containing pUC19 and the 5' part of the prochymosin gene (prochymosin') was isolated. This fragment was ligated with a 0.6 kb EcoRI-BanI fragment from pTAKA 17 and the following synthetic oligomer

```
GCACCTGCTTTGGC
    GACGAAAC         (KFN 280/281)
```

Figure 15A:
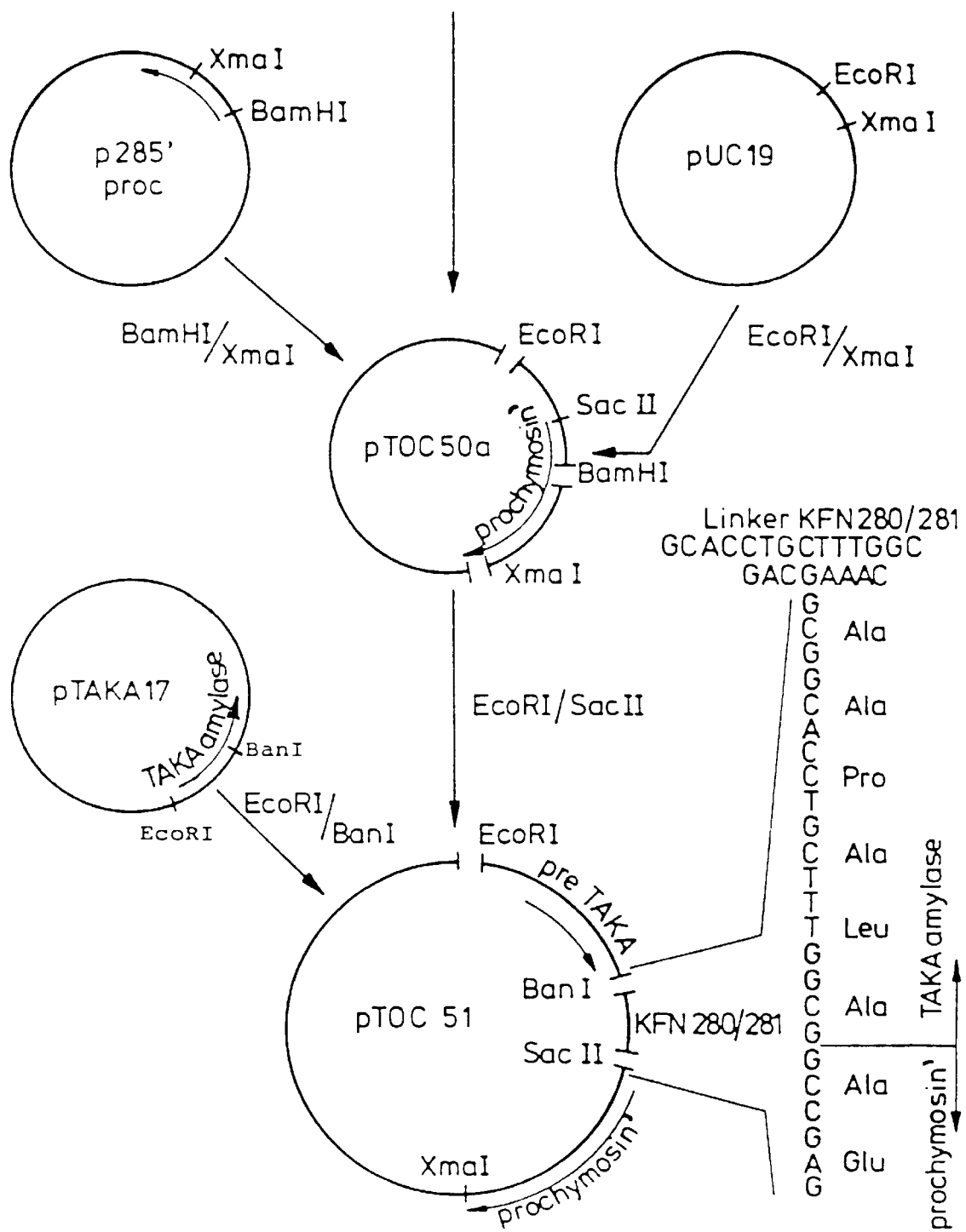
FIG. 15a illustrates the construction of plasmid pTOC51.

After transformation a plasmid pToC51 containing the 5' part of the prochymosin gene (prochymosin') fused to the signal sequence from the *A. oryzae* TAKA-amylase gene (preTAKA) and preceded by approximately 500 bp upstream TAKA-amylase sequence was isolated. The construction of pToC51 is illustrated in FIG. 15a.

pR26 was cut with HinfI, treated with the large fragment (Klenow) of DNA polymerase I and the four dNTP's and cut with XmaI. A 750 bp fragment containing the 3' end of the prochymosin gene was isolated. With the purpose of inserting a HindIII at the 3' end of this fragment pUC9 was cut with XmaI/HincII and the large fragment was ligated to the 750 bp fragment containing the 3' end of the prochymosin gene.

Figure 15B:
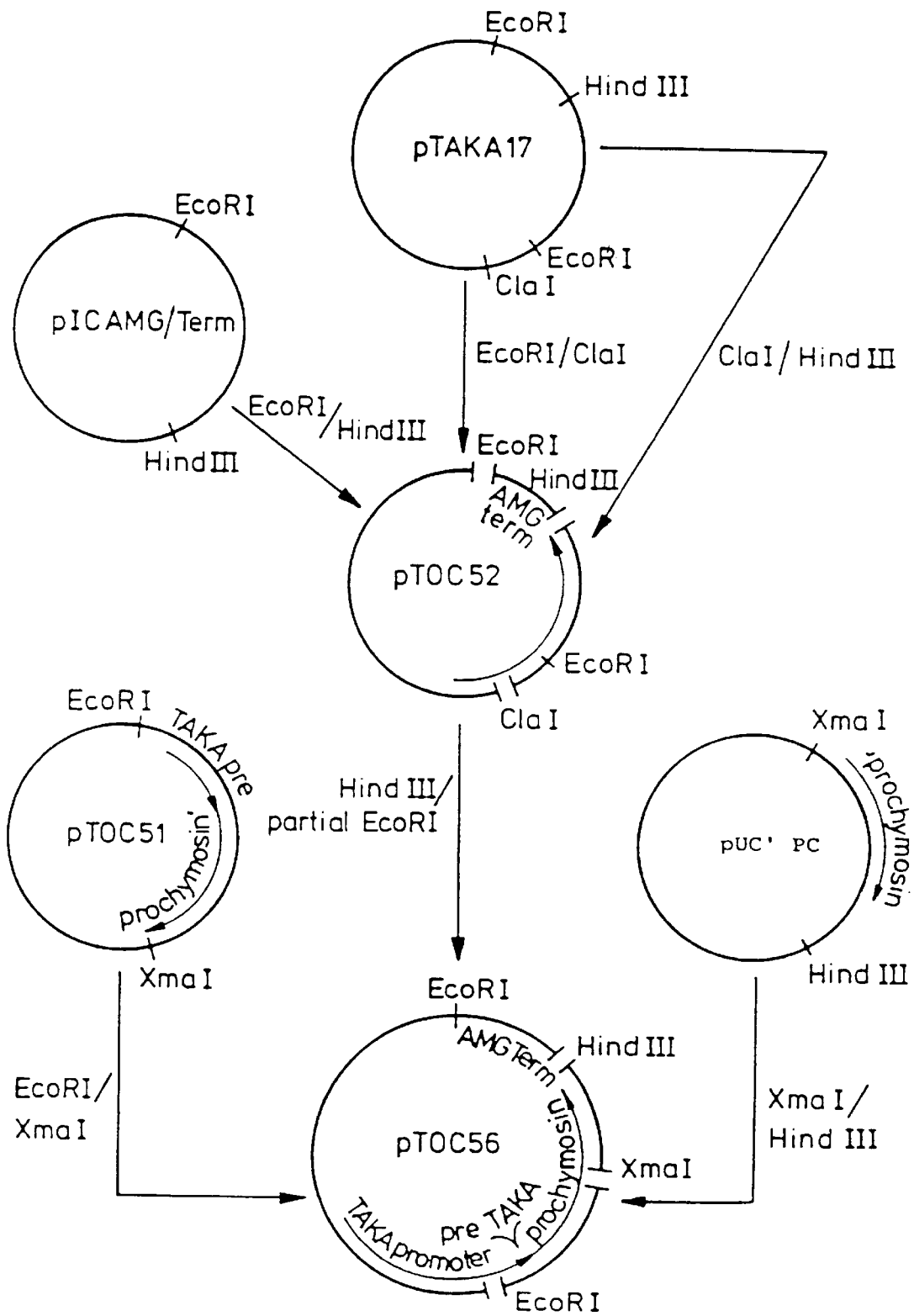
FIG. 15b illustrates the construction of plasmid pTOC56.

A 5.6 kb EcoRI-ClaI fragment from pTAKA 17 was isolated and ligated with a 2.6 kb ClaI-HindIII fragment from the same plasmid plus a 0.7 kb EcoRI-HindIII fragment from pICAMG/Term (see example 3) containing the *A. niger* glucoamylase gene terminator and polyA site. The resulting plasmid is illustrated in FIG. 15b as pToC52.

pToC 52 was cut with HindIII and partially with EcoRI and a 6.4 kb fragment was isolated. This was ligated with a 0.9 kb EcoRI-XmaI fragment from pToC51 and a 0.7 kb XmaI-HindIII fragment from pUC9'PC containing the 3' part of the prochymosin gene ('prochymosin). The resulting plasmid is called pToC56 and is depicted in FIG. 15b.

Example 13
Expression of Prochymosin in *A. oryzae* pToC56 was transformed into *A. oryzae* IFO 4177 or an argB mutant thereof by cotransformation with either p3SR2 (amdS gene) or pSal43 (argB gene). Transformants which grew on selective media were reisolated twice as described in example 9.

The transformants were grown for three days in YPD and the prochymosin content in supernatants was analysed by ELISA on a Western blot after SDS-PAGE. The transformants produced 1–10 mg/l of a prochymosin size immunoreactive protein in the supernatants. No other immunoreactive proteins were detected in the supernatants.

Example 14
Expression of RML in *A. oryzae* p787 from example 7 was transformed into IFO-4177 by cotransformation with p3SR2 by the procedure described in example 9. Transformants were selected and reisolated as described in example 9.

Supernatants from YPD cultures of the transformants grown for three days were analyzed by SDS-PAGE followed by Western blotting and ELISA. The best transformant produced 2 mg/l of a protein the size of the matured RML. The lipase activity in the supernatants was assayed as the ability to cleave tributyrin (NOVO method AF 95.1/3-GB).

The measurement confirmed that 2 mg/l of active lipase was present in the supernatants.

Example 15
Expression of Recombinant Humicola Lipase (RHL) in an *A. oryzae* Strain p960 is transformed into *A. oryzae* IFO 4177 by cotransformation with p3SR2 containing the amdS gene from *A. nidulans* as described in example 9. Protoplasts prepared as described were incubated with a mixture of equal amounts of p960 and p3SR2 (approximately 5 μg of each). Transformants which can use acetamide as sole nitrogen source are reisolated twice. After growth on YPD (Sherman et al, 1981) for three days culture supernatants are analysed by SDS-PAGE. The gels are stained with coomassie brilliant blue R. The best transformants are selected for further studies and grown in a 2 liter Kieler fermentor on 4% soy bean meal and supplied with glucose during growth. The culture is heavily agitated during fermentation. The recombinant Humicola lipase product (RHL) was isolated from the culture broth by removal of the cells by centrifugation, ultrafiltration of the supernatant and freeze drying.

Example 16
Expression of Humicola Lipase in an *A. niger* Strain p960 was transformed into *A. niger* argB by cotransformation with pSal43 containing the argB gene form *A. nidulans* as described in Example 9. Protoplast were incubated with equal amounts, approximately 5 μg, of each plasmid. Transformants were selected on minimal plates (Cove Biochim.Biophys.Acta 113 (1966), 55–56) by relief of argenine requirement.

After two reisolations of conidiospores the transformants were cultured for seven days in YPD (Sherman et al., 1981) at 30° C. The culture supernatants were analyzed by SDS-PAGE. Most of the transformants produced Humicola lipase in their supernatants.

The carbohydrate content was analyzed by Endo H treatment as described in Example 17. It was found that the carbohydrate content was of about the same magnitude as for the native Humicola lipase. The Endo H sensitivity was the same as for the recombinant Humicola lipase from *A. oryzae*. It was accordingly assumed that the nature of the glycosylation is the same in *A. oryzae* and *A. niger*.

Example 17
Determination of Carbohydrate Content in RHL (Recombinant Lipase Product from Example 15) and HLL (Native Lipase Product from Cultivaton of DSM4109). Treatment with Enzymes capable of Cleaving off Carbohydrate Side Chains (Endo H and Glycopeptidase F).

RHL and HLL were treated with glycopeptidase F (Boehringer No. 91378, 100 units. 1 vial dissolved in 500 μl water) and Endo H (Sigma No. E6878, dissolved in citrate buffer pH 5.5).

HLL and RHL were each dissolved in 10 mM Tris pH 7.5 (1 mg/ml). To 100 μl HLL and RHL, respectively 2 μl glycopeptidase F was added and the samples were incubated at 37° C. for 20 hours.

HLL and RHL were furthermore each dissolved in 10 mM Tris pH 7.5 (1 mg/ml) and 25 μl Endo H and 50 μl 0.1M sodium. acetate pH 5.0 were added to 25 μl of HLL and RHL, respectively. The samples were incubated at 37° C. for 20 hours.

Figure 20:
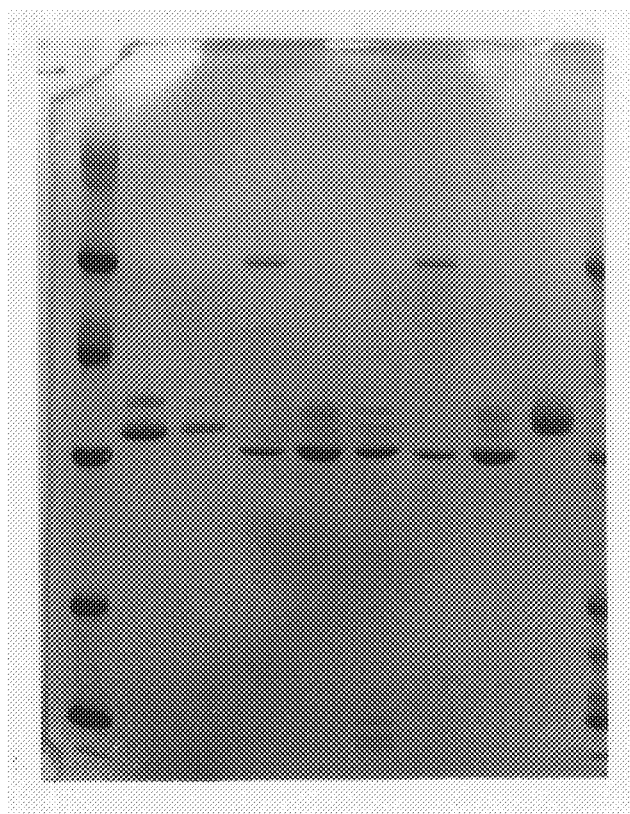
FIG. 20 shows an SDS-PAGE gradient gel.

The samples were run on SDS-PAGE gradient gels 7.5–20% together with untreated HLL and RHL. The SDS-PAGE gradient gel is shown in FIG. 20. The samples in FIG. 20 are as follows:

1) Standard: 92K, 67K, 43K, 30K, 20.1K, 14.4K
2) HLL, 1 mg/ml in 10 mM Tris pH 7.5.
3) HLL+Endo H
4) RHL+Endo H
5) RHL+Glycopeptidase F
6) HLL+Glycopeptidase F
7) RHL+Endo H
8) RHL+Glycopeptidase F
9) RHL, 1 mg/ml in 10 mM Tris pH 7.5.

It appears from FIG. 20 that glycopeptidase F is capable of cleaving off the carbohydrate part of both HLL and RHL and that the remaining protein is of the same size. Endo H is on the other hand only capable of cleaving off carbohydrates of RHL whereas Endo H treatment of HLL does not have any effect.

Accordingly, both HLL and RHL are N-glycosylated. The glycosylation is, however, of a different nature.

Carbohydrate analysis was performed by use of methods described by Thim et. al., submitted for publication in Biochemistry, Chaplin, M. F. (1982), Anal.Biochem. 123, 336–341, and Jentoft, N. (1985), Anal.Biochem. 148, 424–433.

Briefly, samples containing lipase was subjected to methanolysis followed by re-N-acetylation of the amino sugars and elimination of O-acetyl groups by a second, mild methanolysis step. Derivatives suitable for analysis by reverse phase high pressure liquid chromatography was obtained by perbenzoylation of the methyl glycosides.

The result of the analysis is shown in the following table.

|  | Native Humicola lipase HLL mol/mol | Recombinant Humicola lipase RHL mol/mol |
|---|---|---|
| N-acetylglucosamine | 1.2 | 1.2 |
| Mannose | 5.7 | 8.6 |
| Galactose | 0 | 3.3 |

The carbohydrate moiety of the native Humicola lipase, HLL is composed of the two monosaccharides found in N-glycosylations of the high-mannose type (Montrenil, J. et al., (1986) in "Carbohydrate analysis: a practical approach", Chaplin, M. F. and Kenndey, J. F. (Eds.) IRL Press, Oxford, p 143). The result for N-acetylglucosamine (<2 mol/mol) indicates that the primary sequence only contains a single N-glycosylation. This could further be deduced from the cDNA sequence (FIG. 18a+18b). In addition mannose could be O-glycosidic linked to serine or threonine residues.

Besides N-acetylglucosamine and mannose, the recombinant Humicola lipase, RHL comprises galactose in significant amount. As for the native lipase the content of N-acetylglucosamine indicates the presence of a single N-glycosylation, although this is of the complex or hybrid type if galactose is part hereof. O-glycosylation at serine or threonine residues, however, has to be responsible for the presence of galactose if the N-glycosylation of the recombinant RHL lipase is of the high-mannose type as was the case for the native HLL lipase.

In average, the carbohydrate moieties add approximately 1500 D and 2600 D to the molecular weight of the native Humicola lipase HLL and the recombinant Humicola lipase RHL, respectively. This corresponds to a carbohydrate content of about 4.9% and 8.1%, respectively.

Example 18
Effect of pH and Temperature on the Stability of RHL and HLL

RHL ($1.4 \times 10^6$ LU/g) and HLL ($0.2 \times 10^6$ LU/g), respectively, were dissolved in buffer solutions of various pH and incubated for two hours at temperatures 55° and 60° C.

The buffer solutions were made up of 47,5 mM Na-acetate, MOPS (3-(N-morpholino)-propane sulphonic acid), and boric acid, with pH-adjustments to 4, 5, 6, 7, 8, 9, and 10 by means of 1N HCl or 1N NaOH. In addition the buffer solution used in a separate test of a sample of HLL that had been purified to $1.5 \times 10^6$ LU/g was added PMSF (phenylmethan sulfonyl fluorid) to inhibit protease content in this native lipase product.

Lipase concentrations in the solutions were equated to approx. 10–15 LU/ml.

Immediately after the incubations the lipase solutions were cooled down in an ice-water bath and kept there until analysis the same day (LU-method, AF 95).

Figure 19:
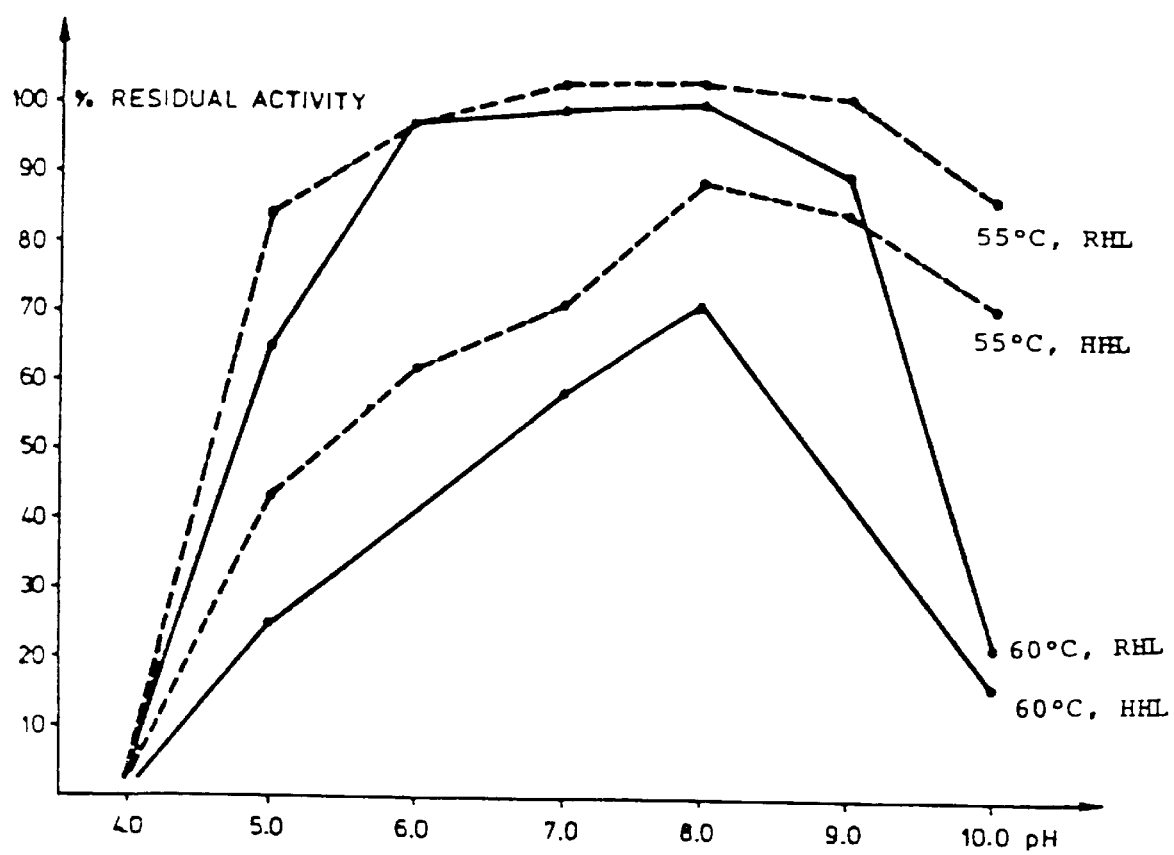
FIG. 19 shows the residual activity of the recombinant Humicola lipase product compared to the residual activity of the native Humicola lipase product at 55° C. and 60° C. at different pH.
Figure 21:
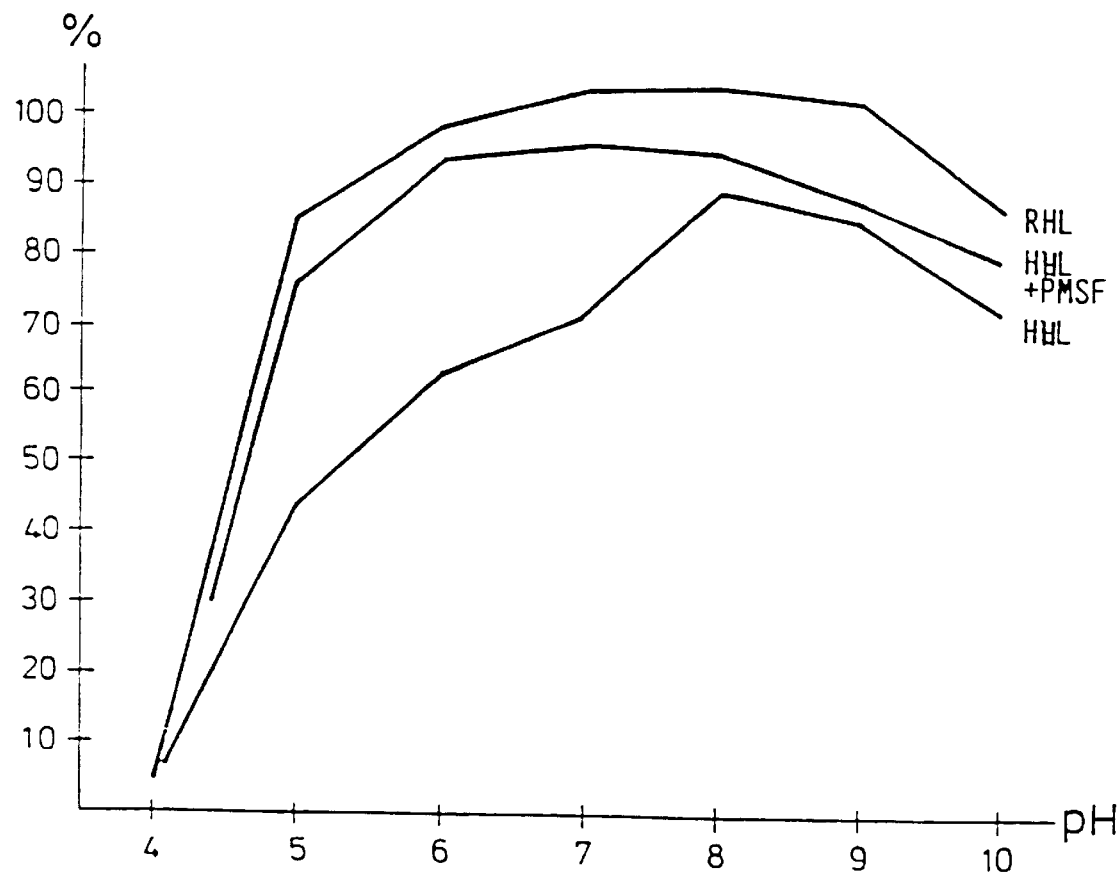
FIG. 21 shows the residual activity at 55° C. of the recombinant Humicola lipase product and the native Humicola lipase product along with the residual activity of the native Humicola lipase containing a protease inhibitor (PMSF)

The results are given in FIG. 19 and in FIG. 21.

It appears from FIG. 19 that the thermostability of RHL is greater than that of HLL at pH 5–10 both at 55° C. and 60° C., respectively.

It appears from FIG. 21 that the greater thermostability of RHL is due only in part to absence of the *H. lanuginose* protease activity.

Example 19
Stability of RHL and HLL of Comparable unit Activity Levels of $4 \times 10^6$ LU/g in the Presence of a Typical Alkaline *Bacillus sp.* Protease, (Here the Commercially Available Detergent Enzyme Esperase™)

The incubation conditions were 0.1M boric acid, pH 9.5 and 40° C. or 55° C. using concentrations of 3600 LU/liter and 0.057 AU/liter (AU/LU=$0.016 \times 10^{-3}$). The residual activities were calculated on the basis of reference incubations.

Figure 22:
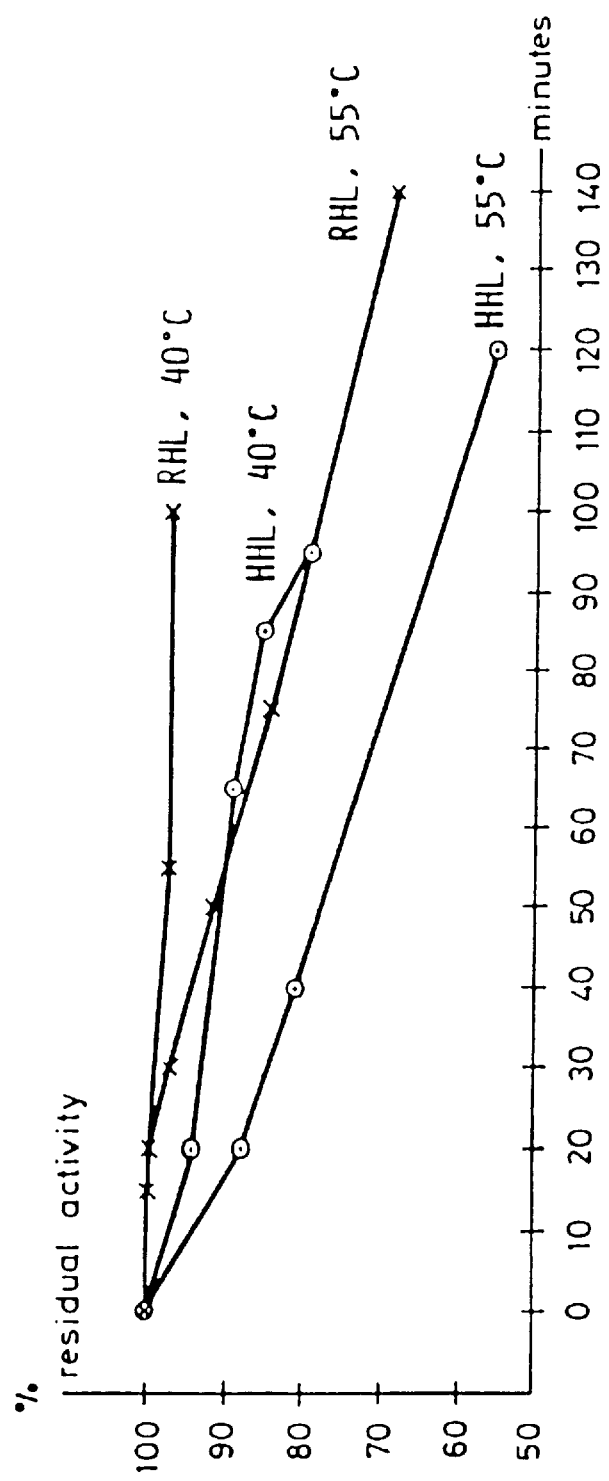
FIG. 22 shows the residual activity at 40° C. and at 55° C. of native and recombinant Humicola lipase in the presence of an alkaline Bacillus protease product (Esperase™)

The results are given in FIG. 22.

It appears from FIG. 22 that the thermostability of RHL in presence of an alkaline Bacillus protease is superior to that of HLL, indicating thereby differences in their susceptibility to attack by proteases.

We claim:

1. A process for expression of a protein product in *Aspergillus oryzae* comprising the steps of:

(a) providing a recombinant DNA cloning vector system which integrates into the genome of an *Aspergillus oryzae* host, the vector system comprising: DNA-sequences encoding functions facilitating gene expression comprising a promoter, transcription initiation sites, and transcription terminator and polyadenylation functions, the promoter optionally being preceded by upstream activating sequences; and a DNA-sequence encoding the protein product operably linked to the DNA sequences encoding functions facilitating gene expression; wherein the promoter is the *A. oryzae* TAKA amylase promoter;

(b) transforming the *Aspergillus oryzae* host with the recombinant DNA cloning vector system from step a; and (c) culturing the transformed *Aspergillus oryzae* host in a culture medium.

2. The process according to claim 1, wherein the vector system further comprises a marker for selection of transformants and the *Aspergillus oryzae* host does not harbor a functional gene for the marker.

3. The process according to claim 2, wherein the vector system comprises two vectors, wherein one contains the selection marker and the other contains DNA-sequences encoding functions facilitating gene expression and a DNA sequence encoding the protein product.

4. The process according to claim 1, wherein the promoter and upstream activating sequences have the following sequence:

```
GTCGACGC ATTCCGAATA CGAGGCCTGA TTAATGATTA CATACGCCTC
CGGGTAGTAG ACCGAGCAGC CGAGCCAGTT CAGCGCCTAA AACGCCTTAT
ACAATTAAGC AGTTAAAGAA GTTAGAATCT ACGCTTAAAA AGCTACTTAA
AAATCGATCT CGCAGTCCCG ATTCGCCTAT CAAAACCAGT TTAAATCAAC
TGATTAAAGG TGCCGAACGA GCTATAAATG ATATAACAAT ATTAAAGCAT
TAATTAGAGC AATATCAGGC CGCGCACGAA AGGCAACTTA AAAAGCGAAA
GCGCTCTACT AAACAGATTA CTTTTGAAAA AGGCACATCA GTATTTAAAG
CCCGAATCCT TATTAAGCGC CGAAATCAGG CAGATAAAGC CATACAGGCA
GATAGACCTC TACCTATTAA ATCGGCTTCT AGGCGCGCTC CATCTAAATG
TTCTGGCTGT GGTGTACAGG GGCATAAAAT TACGCACTAC CCGAATCGAT
AGAACTACTC ATTTTTATAT AGAAGTCAGA ATTCATAGTG TTTTGATCAT
TTTAAATTTT TATATGGCGG GTGGTGGGCA ACTCGCTTGC GCGGGCAACT
CGCTTACCGA TTACGTTAGG GCTGATATTT ACGTGAAAAT CGTCAAGGGA
TGCAAGACCA AAGTAGTAAA ACCCCGGAAG TCAACAGCAT CCAAGCCCAA
GTCCTTCACG GAGAAACCCC AGCGTCCACA TCACGAGCGA AGGACCACCT
CTAGGCATCG GACGCACCAT CCAATTAGAA GCAGCAAAGC GAAACAGCCC
AAGAAAAAGG TCGGCCCGTC GGCCTTTTCT GCAACGCTGA TCACGGGCAG
CGATCCAACC AACACCCTCC AGAGTGACTA GGGGCGGAAA TTTAAAGGGA
TTAATTTCCA CTCAACCACA AATCACAGTC GTCCCCGGTA TTGTCCTGCA
GAATGCAATT TAAACTCTTC TGCGAATCGC TTGGATTCCC CGCCCCTAGT
CGTAGAGCTT AAAGTATGTC CCTTGTCGAT GCGATGTATC ACAACATATA
AATACTAGCA AGGGATGCCA TGCTTGGAGG ATAGCAACCG ACAACATCAC
ATCAAGCTCT CCCTTCTCTG AACAATAAAC CCCACAG.
```

5. The process according to claim 1, wherein the promoter and upstream activating sequences have the following sequence:

```
AGATCTGCCC TTATAAATCT CCTAGTCTGA TCGTCGACGC ATTCCGAATA
CGAGGCCTGA TTAATGATTA CATACGCCTC CGGGTAGTAG ACCGAGCAGC
CGAGCCAGTT CAGCGCCTAA AACGCCTTAT ACAATTAAGC AGTTAAAGAA
GTTAGAATCT ACGCTTAAAA AGCTACTTAA AAATCGATCT CGCAGTCCCG
ATTCGCCTAT CAAAACCAGT TTAAATCAAC TGATTAAAGG TGCCGAACGA
GCTATAAATG ATATAACAAT ATTAAAGCAT TAATTAGAGC AATATCAGGC
CGCGCACGAA AGGCAACTTA AAAAGCGAAA GCGCTCTACT AAACAGATTA
CTTTTGAAAA AGGCACATCA GTATTTAAAG CCCGAATCCT TATTAAGCGC
CGAAATCAGG CAGATAAAGC CATACAGGCA GATAGACCTC TACCTATTAA
ATCGGCTTCT AGGCGCGCTC CATCTAAATG TTCTGGCTGT GGTGTACAGG
GGCATAAAAT TACGCACTAC CCGAATCGAT AGAACTACTC ATTTTTATAT
AGAAGTCAGA ATTCATAGTG TTTTGATCAT TTTAAATTTT TATATGGCGG
GTGGTGGGCA ACTCGCTTGC GCGGGCAACT CGCTTACCGA TTACGTTAGG
GCTGATATTT ACGTGAAAAT CGTCAAGGGA TGCAAGACCA AAGTAGTAAA
ACCCCGGAAG TCAACAGCAT CCAAGCCCAA GTCCTTCACG GAGAAACCCC
AGCGTCCACA TCACGAGCGA AGGACCACCT CTAGGCATCG GACGCACCAT
CCAATTAGAA GCAGCAAAGC GAAACAGCCC AAGAAAAAGG TCGGCCCGTC
GGCCTTTTCT GCAACGCTGA TCACGGGCAG CGATCCAACC AACACCCTCC
AGAGTGACTA GGGGCGGAAA TTTAAAGGGA TTAATTTCCA CTCAACCACA
AATCACAGTC GTCCCCGGTA TTGTCCTGCA GAATGCAATT TAAACTCTTC
TGCGAATCGC TTGGATTCCC CGCCCCTAGT CGTAGAGCTT AAAGTATGTC
CCTTGTCGAT GCGATGTATC ACAACATATA AATACTAGCA AGGGATGCCA
TGCTTGGAGG ATAGCAACCG ACAACATCAC ATCAAGCTCT CCCTTCTCTG
AACAATAAAC CCCACAGAAG GCATTT.
```

6. The process according to claim 5, wherein the promoter and upstream activating sequence is preceded by a 1.05 kb unsequenced upstream region from position 0 to 1.05 in plasmid pTAKA 17.

7. The process according to claim 1, wherein the vector system further comprises a preregion providing for secretion of the product into the culture medium.

8. The process according to claim 7, wherein the preregion is derived from the gene for *A. oryzae* TAKA amylase, *A. niger* neutral α-amylase, *A. niger* acid-stable α-amylase, *B. licheniformis* α-amylase, the maltogenic amylase from Bacillus NCIB 11837, *B. stearothermophilus* α-amylase or *B. licheniformis* subtilisin.

9. The process according to claim 7, wherein the preregion is the preregion of an Aspergillus gene.

10. An *Aspergillus oryzae* strain transformed with a recombinant DNA cloning vector system comprising: DNA-sequences encoding functions facilitating gene expression comprising a promoter, transcription initiation sites, and transcription terminator and polyadenylation functions, the promoter optionally being preceded by upstream activating sequences; and a DNA-sequence encoding the protein product operably linked to the DNA sequences encoding functions facilitating gene expression; wherein the promoter is the *A. oryzae* TAKA amylase promoter.

11. The *Aspergillus oryzae* strain according to claim 10, wherein the vector system further comprises a marker for selection of transformants and the *Aspergillus oryzae* host does not harbor a functional gene for the marker.

12. The *Aspergillus oryzae* strain according to claim 11, wherein the vector system comprises two vectors, wherein one contains the selection marker and the other contains DNA-sequences encoding functions facilitating gene expression and a DNA sequence encoding the protein product.

13. The *Aspergillus oryzae* strain according to claim 10, wherein the promoter and upstream activating sequences have the following sequence:

```
GTCGACGC ATTCCGAATA CGAGGCCTGA TTAATGATTA CATACGCCTC
CGGGTAGTAG ACCGAGCAGC CGAGCCAGTT CAGCGCCTAA AACGCCTTAT
ACAATTAAGC AGTTAAAGAA GTTAGAATCT ACGCTTAAAA AGCTACTTAA
AAATCGATCT CGCAGTCCCG ATTCGCCTAT CAAAACCAGT TTAAATCAAC
TGATTAAAGG TGCCGAACGA GCTATAAATG ATATAACAAT ATTAAAGCAT
TAATTAGAGC AATATCAGGC CGCGCACGAA AGGCAACTTA AAAAGCGAAA
GCGCTCTACT AAACAGATTA CTTTTGAAAA AGGCACATCA GTATTTAAAG
CCCGAATCCT TATTAAGCGC CGAAATCAGG CAGATAAAGC CATACAGGCA
GATAGACCTC TACCTATTAA ATCGGCTTCT AGGCGCGCTC CATCTAAATG
TTCTGGCTGT GGTGTACAGG GGCATAAAAT TACGCACTAC CCGAATCGAT
AGAACTACTC ATTTTTATAT AGAAGTCAGA ATTCATAGTG TTTTGATCAT
TTTAAATTTT TATATGGCGG GTGGTGGGCA ACTCGCTTGC GCGGGCAACT
CGCTTACCGA TTACGTTAGG GCTGATATTT ACGTGAAAAT CGTCAAGGGA
TGCAAGACCA AAGTAGTAAA ACCCCGGAAG TCAACAGCAT CCAAGCCCAA
GTCCTTCACG GAGAAACCCC AGCGTCCACA TCACGAGCGA AGGACCACCT
CTAGGCATCG GACGCACCAT CCAATTAGAA GCAGCAAAGC GAAACAGCCC
AAGAAAAAGG TCGGCCCGTC GGCCTTTTCT GCAACGCTGA TCACGGGCAG
CGATCCAACC AACACCCTCC AGAGTGACTA GGGGCGGAAA TTTAAAGGGA
TTAATTTCCA CTCAACCACA AATCACAGTC GTCCCCGGTA TTGTCCTGCA
GAATGCAATT TAAACTCTTC TGCGAATCGC TTGGATTCCC CGCCCCTAGT
CGTAGAGCTT AAAGTATGTC CCTTGTCGAT GCGATGTATC ACAACATATA
AATACTAGCA AGGGATGCCA TGCTTGGAGG ATAGCAACCG ACAACATCAC
ATCAAGCTCT CCCTTCTCTG AACAATAAAC CCCACAG.
```

14. The *Aspergillus oryzae* strain according to claim 10, wherein the promoter and upstream activating sequences have the following sequence:

```
AGATCTGCCC TTATAAATCT CCTAGTCTGA TCGTCGACGC ATTCCGAATA
CGAGGCCTGA TTAATGATTA CATACGCCTC CGGGTAGTAG ACCGAGCAGC
CGAGCCAGTT CAGCGCCTAA AACGCCTTAT ACAATTAAGC AGTTAAAGAA
GTTAGAATCT ACGCTTAAAA AGCTACTTAA AAATCGATCT CGCAGTCCCG
ATTCGCCTAT CAAAACCAGT TTAAATCAAC TGATTAAAGG TGCCGAACGA
GCTATAAATG ATATAACAAT ATTAAAGCAT TAATTAGAGC AATATCAGGC
CGCGCACGAA AGGCAACTTA AAAAGCGAAA GCGCTCTACT AAACAGATTA
CTTTTGAAAA AGGCACATCA GTATTTAAAG CCCGAATCCT TATTAAGCGC
CGAAATCAGG CAGATAAAGC CATACAGGCA GATAGACCTC TACCTATTAA
ATCGGCTTCT AGGCGCGCTC CATCTAAATG TTCTGGCTGT GGTGTACAGG
GGCATAAAAT TACGCACTAC CCGAATCGAT AGAACTACTC ATTTTTATAT
AGAAGTCAGA ATTCATAGTG TTTTGATCAT TTTAAATTTT TATATGGCGG
GTGGTGGGCA ACTCGCTTGC GCGGGCAACT CGCTTACCGA TTACGTTAGG
GCTGATATTT ACGTGAAAAT CGTCAAGGGA TGCAAGACCA AAGTAGTAAA
ACCCCGGAAG TCAACAGCAT CCAAGCCCAA GTCCTTCACG GAGAAACCCC
AGCGTCCACA TCACGAGCGA AGGACCACCT CTAGGCATCG GACGCACCAT
CCAATTAGAA GCAGCAAAGC GAAACAGCCC AAGAAAAAGG TCGGCCCGTC
GGCCTTTTCT GCAACGCTGA TCACGGGCAG CGATCCAACC AACACCCTCC
AGAGTGACTA GGGGCGGAAA TTTAAAGGGA TTAATTTCCA CTCAACCACA
AATCACAGTC GTCCCCGGTA TTGTCCTGCA GAATGCAATT TAAACTCTTC
TGCGAATCGC TTGGATTCCC CGCCCCTAGT CGTAGAGCTT AAAGTATGTC
CCTTGTCGAT GCGATGTATC ACAACATATA AATACTAGCA AGGGATGCCA
TGCTTGGAGG ATAGCAACCG ACAACATCAC ATCAAGCTCT CCCTTCTCTG
AACAATAAAC CCCACAGAAG GCATTT.
```

15. The *Aspergillus oryzae* strain according to claim 14, wherein the promoter and upstream activating sequence is preceded by a 1.05 kb unsequenced upstream region from position 0 to 1.05 in plasmid pTAKA 17.

16. An Aspergillus which has been transformed with a recombinant DNA cloning vector system which integrates into the genome of an Aspergillus host, the vector system comprising: DNA sequences encoding functions facilitating gene expression comprising an *Aspergillus oryzae* TAKA amylase promoter preceded by its upstream activating sequences, a marker for selection of transformants, a transcription initiation site, and transcription terminator and polyadenylation functions; and a DNA sequence encoding a protein product operatively linked to the DNA sequences encoding functions facilitating gene expression; wherein the Aspergillus host, before transformation, did not harbor a functional gene for the marker.

17. The Aspergillus strain according to claim 16, wherein the promoter and upstream activating sequences have the following sequence:

```
GTCGACGC ATTCCGAATA CGAGGCCTGA TTAATGATTA CATACGCCTC
CGGGTAGTAG ACCGAGCAGC CGAGCCAGTT CAGCGCCTAA AACGCCTTAT
ACAATTAAGC AGTTAAAGAA GTTAGAATCT ACGCTTAAAA AGCTACTTAA
AAATCGATCT CGCAGTCCCG ATTCGCCTAT CAAAACCAGT TTAAATCAAC
TGATTAAAGG TGCCGAACGA GCTATAAATG ATATAACAAT ATTAAAGCAT
TAATTAGAGC AATATCAGGC CGCGCACGAA AGGCAACTTA AAAAGCGAAA
GCGCTCTACT AAACAGATTA CTTTTGAAAA AGGCACATCA GTATTTAAAG
CCCGAATCCT TATTAAGCGC CGAAATCAGG CAGATAAAGC CATACAGGCA
GATAGACCTC TACCTATTAA ATCGGCTTCT AGGCGCGCTC CATCTAAATG
TTCTGGCTGT GGTGTACAGG GGCATAAAAT TACGCACTAC CCGAATCGAT
AGAACTACTC ATTTTTATAT AGAAGTCAGA ATTCATAGTG TTTTGATCAT
TTTAAATTTT TATATGGCGG GTGGTGGGCA ACTCGCTTGC GCGGGCAACT
CGCTTACCGA TTACGTTAGG GCTGATATTT ACGTGAAAAT CGTCAAGGGA
TGCAAGACCA AAGTAGTAAA ACCCCGGAAG TCAACAGCAT CCAAGCCCAA
GTCCTTCACG GAGAAACCCC AGCGTCCACA TCACGAGCGA AGGACCACCT
CTAGGCATCG GACGCACCAT CCAATTAGAA GCAGCAAAGC GAAACAGCCC
AAGAAAAAGG TCGGCCCGTC GGCCTTTTCT GCAACGCTGA TCACGGGCAG
CGATCCAACC AACACCCTCC AGAGTGACTA GGGGCGGAAA TTTAAAGGGA
TTAATTTCCA CTCAACCACA AATCACAGTC GTCCCCGGTA TTGTCCTGCA
GAATGCAATT TAAACTCTTC TGCGAATCGC TTGGATTCCC CGCCCCTAGT
CGTAGAGCTT AAAGTATGTC CCTTGTCGAT GCGATGTATC ACAACATATA
AATACTAGCA AGGGATGCCA TGCTTGGAGG ATAGCAACCG ACAACATCAC
ATCAAGCTCT CCCTTCTCTG AACAATAAAC CCCACAG.
```

18. The Aspergillus strain according to claim 16, wherein the promoter and upstream activating sequences have the following sequence:

```
AGATCTGCCC TTATAAATCT CCTAGTCTGA TCGTCGACGC ATTCCGAATA
CGAGGCCTGA TTAATGATTA CATACGCCTC CGGGTAGTAG ACCGAGCAGC
CGAGCCAGTT CAGCGCCTAA AACGCCTTAT ACAATTAAGC AGTTAAAGAA
GTTAGAATCT ACGCTTAAAA AGCTACTTAA AAATCGATCT CGCAGTCCCG
ATTCGCCTAT CAAAACCAGT TTAAATCAAC TGATTAAAGG TGCCGAACGA
GCTATAAATG ATATAACAAT ATTAAAGCAT TAATTAGAGC AATATCAGGC
CGCGCACGAA AGGCAACTTA AAAAGCGAAA GCGCTCTACT AAACAGATTA
CTTTTGAAAA AGGCACATCA GTATTTAAAG CCCGAATCCT TATTAAGCGC
CGAAATCAGG CAGATAAAGC CATACAGGCA GATAGACCTC TACCTATTAA
ATCGGCTTCT AGGCGCGCTC CATCTAAATG TTCTGGCTGT GGTGTACAGG
GGCATAAAAT TACGCACTAC CCGAATCGAT AGAACTACTC ATTTTTATAT
AGAAGTCAGA ATTCATAGTG TTTTGATCAT TTTAAATTTT TATATGGCGG
GTGGTGGGCA ACTCGCTTGC GCGGGCAACT CGCTTACCGA TTACGTTAGG
GCTGATATTT ACGTGAAAAT CGTCAAGGGA TGCAAGACCA AAGTAGTAAA
ACCCCGGAAG TCAACAGCAT CCAAGCCCAA GTCCTTCACG GAGAAACCCC
AGCGTCCACA TCACGAGCGA AGGACCACCT CTAGGCATCG GACGCACCAT
CCAATTAGAA GCAGCAAAGC GAAACAGCCC AAGAAAAAGG TCGGCCCGTC
GGCCTTTTCT GCAACGCTGA TCACGGGCAG CGATCCAACC AACACCCTCC
AGAGTGACTA GGGGCGGAAA TTTAAAGGGA TTAATTTCCA CTCAACCACA
AATCACAGTC GTCCCCGGTA TTGTCCTGCA GAATGCAATT TAAACTCTTC
TGCGAATCGC TTGGATTCCC CGCCCCTAGT CGTAGAGCTT AAAGTATGTC
CCTTGTCGAT GCGATGTATC ACAACATATA AATACTAGCA AGGGATGCCA
TGCTTGGAGG ATAGCAACCG ACAACATCAC ATCAAGCTCT CCCTTCTCTG
AACAATAAAC CCCACAGAAG GCATTT.
```

19. The Aspergillus strain according to claim 16, wherein the promoter and upstream activating sequence is preceded by a 1.05 kb unsequenced upstream region from position 0 to 1.05 in plasmid pTAKA 17.

20. The Aspergillus strain according to claim 16, wherein the vector system comprises two vectors, wherein one contains the selection marker and the other contains DNA-sequences encoding functions facilitating gene expression and a DNA sequence encoding the protein product.

21. A process for the expression of a protein product in Aspergillus comprising the steps of:
 (a) providing a recombinant DNA cloning vector system which integrates into the genome of an Aspergillus host in one or more copies, the vector system comprising:
  (i) DNA sequence encoding functions facilitating gene expression comprising:
   an *Aspergillus oryzae* TAKA amylase promoter, the promoter optionally being preceded by upstream activating sequences;
   transcription initiation sites; and
   transcription terminator and polyadenylation functions;
  (ii) a DNA sequence encoding the protein product operatively linked to the DNA sequences encoding functions facilitating gene expression;
 (b) transforming the Aspergillus host with the recombinant DNA cloning vector system from step (a); and
 (c) culturing the transformed Aspergillus host in a culture medium.

22. The process according to claim 21, wherein the vector system further comprises a marker for selection of transformants and the Aspergillus host does not harbor a functional gene for the marker.

23. The process according to claim 22, wherein the vector system comprises two vectors, wherein one contains the selection marker and the other contains DNA-sequences encoding functions facilitating gene expression and a DNA sequence encoding the protein product.

24. The process according to claim 21, wherein the promoter and upstream activating sequences have the following sequence:

```
GTCGACGC ATTCCGAATA CGAGGCCTGA TTAATGATTA CATACGCCTC
CGGGTAGTAG ACCGAGCAGC CGAGCCAGTT CAGCGCCTAA AACGCCTTAT
ACAATTAAGC AGTTAAAGAA GTTAGAATCT ACGCTTAAAA AGCTACTTAA
AAATCGATCT CGCAGTCCCG ATTCGCCTAT CAAAACCAGT TTAAATCAAC
TGATTAAAGG TGCCGAACGA GCTATAAATG ATATAACAAT ATTAAAGCAT
TAATTAGAGC AATATCAGGC CGCGCACGAA AGGCAACTTA AAAAGCGAAA
GCGCTCTACT AAACAGATTA CTTTTGAAAA AGGCACATCA GTATTTAAAG
CCCGAATCCT TATTAAGCGC CGAAATCAGG CAGATAAAGC CATACAGGCA
GATAGACCTC TACCTATTAA ATCGGCTTCT AGGCGCGCTC CATCTAAATG
TTCTGGCTGT GGTGTACAGG GGCATAAAAT TACGCACTAC CCGAATCGAT
AGAACTACTC ATTTTTATAT AGAAGTCAGA ATTCATAGTG TTTTGATCAT
TTTAAATTTT TATATGGCGG GTGGTGGGCA ACTCGCTTGC GCGGGCAACT
CGCTTACCGA TTACGTTAGG GCTGATATTT ACGTGAAAAT CGTCAAGGGA
TGCAAGACCA AAGTAGTAAA ACCCCGGAAG TCAACAGCAT CCAAGCCCAA
GTCCTTCACG GAGAAACCCC AGCGTCCACA TCACGAGCGA AGGACCACCT
CTAGGCATCG GACGCACCAT CCAATTAGAA GCAGCAAAGC GAAACAGCCC
AAGAAAAAGG TCGGCCCGTC GGCCTTTTCT GCAACGCTGA TCACGGGCAG
CGATCCAACC AACACCCTCC AGAGTGACTA GGGGCGGAAA TTTAAAGGGA
TTAATTTCCA CTCAACCACA AATCACAGTC GTCCCCGGTA TTGTCCTGCA
GAATGCAATT TAAACTCTTC TGCGAATCGC TTGGATTCCC CGCCCCTAGT
CGTAGAGCTT AAAGTATGTC CCTTGTCGAT GCGATGTATC ACAACATATA
AATACTAGCA AGGGATGCCA TGCTTGGAGG ATAGCAACCG ACAACATCAC
ATCAAGCTCT CCCTTCTCTG AACAATAAAC CCCACAG.
```

25. The process according to claim 21, wherein the promoter and upstream activating sequences have the following sequence:

```
AGATCTGCCC TTATAAATCT CCTAGTCTGA TCGTCGACGC ATTCCGAATA
CGAGGCCTGA TTAATGATTA CATACGCCTC CGGGTAGTAG ACCGAGCAGC
CGAGCCAGTT CAGCGCCTAA AACGCCTTAT ACAATTAAGC AGTTAAAGAA
GTTAGAATCT ACGCTTAAAA AGCTACTTAA AAATCGATCT CGCAGTCCCG
ATTCGCCTAT CAAAACCAGT TTAAATCAAC TGATTAAAGG TGCCGAACGA
GCTATAAATG ATATAACAAT ATTAAAGCAT TAATTAGAGC AATATCAGGC
CGCGCACGAA AGGCAACTTA AAAAGCGAAA GCGCTCTACT AAACAGATTA
CTTTTGAAAA AGGCACATCA GTATTTAAAG CCCGAATCCT TATTAAGCGC
CGAAATCAGG CAGATAAAGC CATACAGGCA GATAGACCTC TACCTATTAA
ATCGGCTTCT AGGCGCGCTC CATCTAAATG TTCTGGCTGT GGTGTACAGG
GGCATAAAAT TACGCACTAC CCGAATCGAT AGAACTACTC ATTTTTATAT
AGAAGTCAGA ATTCATAGTG TTTTGATCAT TTTAAATTTT TATATGGCGG
GTGGTGGGCA ACTCGCTTGC GCGGGCAACT CGCTTACCGA TTACGTTAGG
GCTGATATTT ACGTGAAAAT CGTCAAGGGA TGCAAGACCA AAGTAGTAAA
ACCCCGGAAG TCAACAGCAT CCAAGCCCAA GTCCTTCACG GAGAAACCCC
AGCGTCCACA TCACGAGCGA AGGACCACCT CTAGGCATCG GACGCACCAT
CCAATTAGAA GCAGCAAAGC GAAACAGCCC AAGAAAAAGG TCGGCCCGTC
GGCCTTTTCT GCAACGCTGA TCACGGGCAG CGATCCAACC AACACCCTCC
AGAGTGACTA GGGGCGGAAA TTTAAAGGGA TTAATTTCCA CTCAACCACA
AATCACAGTC GTCCCCGGTA TTGTCCTGCA GAATGCAATT TAAACTCTTC
TGCGAATCGC TTGGATTCCC CGCCCCTAGT CGTAGAGCTT AAAGTATGTC
CCTTGTCGAT GCGATGTATC ACAACATATA AATACTAGCA AGGGATGCCA
TGCTTGGAGG ATAGCAACCG ACAACATCAC ATCAAGCTCT CCCTTCTCTG
AACAATAAAC CCCACAGAAG GCATTT.
```

26. The process according to claim 25, wherein the promoter and upstream activating sequence is preceded by a 1.05 kb unsequenced upstream region from position 0 to 1.05 in plasmid pTAKA 17.

27. The process according to claim 21, wherein the vector system further comprises a preregion providing for secretion of the product into the culture medium.

28. The process according to claim 27, wherein the preregion is derived from the gene for *A. oryzae* TAKA amylase, *A. niger* neutral α-amylase, *A. niger* acid-stable α-amylase, *B. licheniformis* α-amylase, the maltogenic amylase from Bacillus NCIB 11837, *B. stearothermophilus* α-amylase or *B. licheniformis* subtilisin.

29. The process according to claim 21, wherein the preregion is the preregion of an Aspergillus gene.

30. An isolated promoter for expression of a protein product in Aspergillus, comprising the TAKA-amylase promoter, optionally preceded by upstream activating sequences.

31. The promoter and upstream activating sequences according to claim 30 having the following sequence:

```
AGATCTGCCC TTATAAATCT CCTAGTCTGA TCGTCGACGC ATTCCGAATA
CGAGGCCTGA TTAATGATTA CATACGCCTC CGGGTAGTAG ACCGAGCAGC
CGAGCCAGTT CAGCGCCTAA AACGCCTTAT ACAATTAAGC AGTTAAAGAA
GTTAGAATCT ACGCTTAAAA AGCTACTTAA AAATCGATCT CGCAGTCCCG
ATTCGCCTAT CAAAACCAGT TTAAATCAAC TGATTAAAGG TGCCGAACGA
GCTATAAATG ATATAACAAT ATTAAAGCAT TAATTAGAGC AATATCAGGC
CGCGCACGAA AGGCAACTTA AAAAGCGAAA GCGCTCTACT AAACAGATTA
CTTTTGAAAA AGGCACATCA GTATTTAAAG CCCGAATCCT TATTAAGCGC
CGAAATCAGG CAGATAAAGC CATACAGGCA GATAGACCTC TACCTATTAA
ATCGGCTTCT AGGCGCGCTC CATCTAAATG TTCTGGCTGT GGTGTACAGG
GGCATAAAAT TACGCACTAC CCGAATCGAT AGAACTACTC ATTTTTATAT
AGAAGTCAGA ATTCATAGTG TTTTGATCAT TTTAAATTTT TATATGGCGG
GTGGTGGGCA ACTCGCTTGC GCGGGCAACT CGCTTACCGA TTACGTTAGG
GCTGATATTT ACGTGAAAAT CGTCAAGGGA TGCAAGACCA AAGTAGTAAA
ACCCCGGAAG TCAACAGCAT CCAAGCCCAA GTCCTTCACG GAGAAACCCC
AGCGTCCACA TCACGAGCGA AGGACCACCT CTAGGCATCG GACGCACCAT
CCAATTAGAA GCAGCAAAGC GAAACAGCCC AAGAAAAAGG TCGGCCCGTC
GGCCTTTTCT GCAACGCTGA TCACGGGCAG CGATCCAACC AACACCCTCC
AGAGTGACTA GGGGCGGAAA TTTAAAGGGA TTAATTTCCA CTCAACCACA
AATCACAGTC GTCCCCGGTA TTGTCCTGCA GAATGCAATT TAAACTCTTC
TGCGAATCGC TTGGATTCCC CGCCCCTAGT CGTAGAGCTT AAAGTATGTC
CCTTGTCGAT GCGATGTATC ACAACATATA AATACTAGCA AGGGATGCCA
TGCTTGGAGG ATAGCAACCG ACAACATCAC ATCAAGCTCT CCCTTCTCTG
AACAATAAAC CCCACAGAAG GCATTT.
```

32. The promoter and upstream activating sequences according to claim 31, wherein the upstream activating sequences are preceded by a 1.05 kb unsequenced upstream region from position 0 to 1.05 in plasmid pTAKA 17.

33. The promoter and upstream activating sequences according to claim 30 having the following sequence:

```
GTCGACGC ATTCCGAATA CGAGGCCTGA TTAATGATTA CATACGCCTC
CGGGTAGTAG ACCGAGCAGC CGAGCCAGTT CAGCGCCTAA AACGCCTTAT
ACAATTAAGC AGTTAAAGAA GTTAGAATCT ACGCTTAAAA AGCTACTTAA
AAATCGATCT CGCAGTCCCG ATTCGCCTAT CAAAACCAGT TTAAATCAAC
TGATTAAAGG TGCCGAACGA GCTATAAATG ATATAACAAT ATTAAAGCAT
TAATTAGAGC AATATCAGGC CGCGCACGAA AGGCAACTTA AAAAGCGAAA
GCGCTCTACT AAACAGATTA CTTTTGAAAA AGGCACATCA GTATTTAAAG
CCCGAATCCT TATTAAGCGC CGAAATCAGG CAGATAAAGC CATACAGGCA
GATAGACCTC TACCTATTAA ATCGGCTTCT AGGCGCGCTC CATCTAAATG
TTCTGGCTGT GGTGTACAGG GGCATAAAAT TACGCACTAC CCGAATCGAT
AGAACTACTC ATTTTTATAT AGAAGTCAGA ATTCATAGTG TTTTGATCAT
TTTAAATTTT TATATGGCGG GTGGTGGGCA ACTCGCTTGC GCGGGCAACT
CGCTTACCGA TTACGTTAGG GCTGATATTT ACGTGAAAAT CGTCAAGGGA
TGCAAGACCA AAGTAGTAAA ACCCCGGAAG TCAACAGCAT CCAAGCCCAA
GTCCTTCACG GAGAAACCCC AGCGTCCACA TCACGAGCGA AGGACCACCT
CTAGGCATCG GACGCACCAT CCAATTAGAA GCAGCAAAGC GAAACAGCCC
AAGAAAAAGG TCGGCCCGTC GGCCTTTTCT GCAACGCTGA TCACGGGCAG
CGATCCAACC AACACCCTCC AGAGTGACTA GGGGCGGAAA TTTAAAGGGA
TTAATTTCCA CTCAACCACA AATCACAGTC GTCCCCGGTA TTGTCCTGCA
GAATGCAATT TAAACTCTTC TGCGAATCGC TTGGATTCCC CGCCCCTAGT
CGTAGAGCTT AAAGTATGTC CCTTGTCGAT GCGATGTATC ACAACATATA
AATACTAGCA AGGGATGCCA TGCTTGGAGG ATAGCAACCG ACAACATCAC
ATCAAGCTCT CCCTTCTCTG AACAATAAAC CCCACAG.
```

34. A process for producing a protein comprising:
(a) culturing an Aspergillus host comprising a recombinant DNA cloning vector system which comprises one or more copies of (i) DNA sequences encoding functions facilitating gene expression comprising an *Aspergillus oryzae* TAKA amylase promoter, transcription initiation sites, and transcription terminator and polyadenylation functions, wherein the promoter optionally is preceded by upstream activating sequences; and (ii) a DNA sequence encoding the protein operably linked to the DNA sequences encoding functions facilitating gene expression; and (b) recovering the protein.

35. The process of claim 34, wherein the Aspergillus host is an *Aspergillus oryzae* host.

36. The process of claim 35, wherein the vector system further comprises a marker for selection of transformants and the *Aspergillus oryzae* host does not harbor a functional gene for the marker.

37. The process of claim 36, wherein the vector system comprises two vectors, wherein one contains the selection marker and the other contains the DNA sequences encoding functions facilitating gene expression and a DNA sequence encoding the protein product.

38. The process of claim 35, wherein the promoter and upstream activating sequences have the following sequence:

```
GTCGACGC ATTCCGAATA CGAGGCCTGA TTAATGATTA CATACGCCTC
CGGGTAGTAG ACCGAGCAGC CGAGCCAGTT CAGCGCCTAA AACGCCTTAT
ACAATTAAGC AGTTAAAGAA GTTAGAATCT ACGCTTAAAA AGCTACTTAA
AAATCGATCT CGCAGTCCCG ATTCGCCTAT CAAAACCAGT TTAAATCAAC
TGATTAAAGG TGCCGAACGA GCTATAAATG ATATAACAAT ATTAAAGCAT
TAATTAGAGC AATATCAGGC CGCGCACGAA AGGCAACTTA AAAAGCGAAA
GCGCTCTACT AAACAGATTA CTTTTGAAAA AGGCACATCA GTATTTAAAG
CCCGAATCCT TATTAAGCGC CGAAATCAGG CAGATAAAGC CATACAGGCA
GATAGACCTC TACCTATTAA ATCGGCTTCT AGGCGCGCTC CATCTAAATG
TTCTGGCTGT GGTGTACAGG GGCATAAAAT TACGCACTAC CCGAATCGAT
AGAACTACTC ATTTTTATAT AGAAGTCAGA ATTCATAGTG TTTTGATCAT
TTTAAATTTT TATATGGCGG GTGGTGGGCA ACTCGCTTGC GCGGGCAACT
CGCTTACCGA TTACGTTAGG GCTGATATTT ACGTGAAAAT CGTCAAGGGA
TGCAAGACCA AAGTAGTAAA ACCCCGGAAG TCAACAGCAT CCAAGCCCAA
GTCCTTCACG GAGAAACCCC AGCGTCCACA TCACGAGCGA AGGACCACCT
CTAGGCATCG GACGCACCAT CCAATTAGAA GCAGCAAAGC GAAACAGCCC
AAGAAAAAGG TCGGCCCGTC GGCCTTTTCT GCAACGCTGA TCACGGGCAG
CGATCCAACC AACACCCTCC AGAGTGACTA GGGGCGGAAA TTTAAAGGGA
TTAATTTCCA CTCAACCACA AATCACAGTC GTCCCCGGTA TTGTCCTGCA
GAATGCAATT TAAACTCTTC TGCGAATCGC TTGGATTCCC CGCCCCTAGT
CGTAGAGCTT AAAGTATGTC CCTTGTCGAT GCGATGTATC ACAACATATA
AATACTAGCA AGGGATGCCA TGCTTGGAGG ATAGCAACCG ACAACATCAC
ATCAAGCTCT CCCTTCTCTG AACAATAAAC CCCACAG.
```

39. The process of claim 35, wherein the promoter and upstream activating sequences have the following sequence:

```
AGATCTGCCC TTATAAATCT CCTAGTCTGA TCGTCGACGC ATTCCGAATA
CGAGGCCTGA TTAATGATTA CATACGCCTC CGGGTAGTAG ACCGAGCAGC
CGAGCCAGTT CAGCGCCTAA AACGCCTTAT ACAATTAAGC AGTTAAAGAA
GTTAGAATCT ACGCTTAAAA AGCTACTTAA AAATCGATCT CGCAGTCCCG
ATTCGCCTAT CAAAACCAGT TTAAATCAAC TGATTAAAGG TGCCGAACGA
GCTATAAATG ATATAACAAT ATTAAAGCAT TAATTAGAGC AATATCAGGC
CGCGCACGAA AGGCAACTTA AAAAGCGAAA GCGCTCTACT AAACAGATTA
CTTTTGAAAA AGGCACATCA GTATTTAAAG CCCGAATCCT TATTAAGCGC
CGAAATCAGG CAGATAAAGC CATACAGGCA GATAGACCTC TACCTATTAA
ATCGGCTTCT AGGCGCGCTC CATCTAAATG TTCTGGCTGT GGTGTACAGG
GGCATAAAAT TACGCACTAC CCGAATCGAT AGAACTACTC ATTTTTATAT
AGAAGTCAGA ATTCATAGTG TTTTGATCAT TTTAAATTTT TATATGGCGG
GTGGTGGGCA ACTCGCTTGC GCGGGCAACT CGCTTACCGA TTACGTTAGG
GCTGATATTT ACGTGAAAAT CGTCAAGGGA TGCAAGACCA AAGTAGTAAA
ACCCCGGAAG TCAACAGCAT CCAAGCCCAA GTCCTTCACG GAGAAACCCC
AGCGTCCACA TCACGAGCGA AGGACCACCT CTAGGCATCG GACGCACCAT
CCAATTAGAA GCAGCAAAGC GAAACAGCCC AAGAAAAAGG TCGGCCCGTC
GGCCTTTTCT GCAACGCTGA TCACGGGCAG CGATCCAACC AACACCCTCC
AGAGTGACTA GGGGCGGAAA TTTAAAGGGA TTAATTTCCA CTCAACCACA
AATCACAGTC GTCCCCGGTA TTGTCCTGCA GAATGCAATT TAAACTCTTC
TGCGAATCGC TTGGATTCCC CGCCCCTAGT CGTAGAGCTT AAAGTATGTC
CCTTGTCGAT GCGATGTATC ACAACATATA AATACTAGCA AGGGATGCCA
TGCTTGGAGG ATAGCAACCG ACAACATCAC ATCAAGCTCT CCCTTCTCTG
AACAATAAAC CCCACAGAAG GCATTT.
```

40. The process of claim 39, wherein the promoter and upstream activating sequence is preceded by a 1.05 kb unsequenced upstream region from position 0 to 1.05 in plasmid pTAKA 17.

41. The process of claim 35, wherein the vector system further comprises a preregion providing for secretion of the product into the culture medium.

42. The process of claim 41, wherein the preregion is derived from the gene for *A. oryzae* TAKA amylase, *A. niger* neutral α-amylase, *A. niger* acid-stable α-amylase, *B. licheniformis* α-amylase, the maltogenic amylase from Bacillus NCIB 11837, *B. stearothermophilus* α-amylase or *B. licheniformis* subtilisin.

43. The process of claim 41, wherein the preregion is the preregion of an Aspergillus gene.

44. The process of claim 34, wherein the vector system further comprises a marker for selection of transformants and the Aspergillus host does not harbor a functional gene for the marker.

45. The process of claim 44, wherein the vector system comprises two vectors, wherein one contains the selection marker and the other contains the DNA sequences encoding functions facilitating gene expression and a DNA sequence encoding the protein product.

46. The process of claim 34, wherein the promoter and upstream activating sequences have the following sequence:

```
GTCGACGC ATTCCGAATA CGAGGCCTGA TTAATGATTA CATACGCCTC
CGGGTAGTAG ACCGAGCAGC CGAGCCAGTT CAGCGCCTAA AACGCCTTAT
ACAATTAAGC AGTTAAAGAA GTTAGAATCT ACGCTTAAAA AGCTACTTAA
AAATCGATCT CGCAGTCCCG ATTCGCCTAT CAAAACCAGT TTAAATCAAC
TGATTAAAGG TGCCGAACGA GCTATAAATG ATATAACAAT ATTAAAGCAT
TAATTAGAGC AATATCAGGC CGCGCACGAA AGGCAACTTA AAAAGCGAAA
GCGCTCTACT AAACAGATTA CTTTTGAAAA AGGCACATCA GTATTTAAAG
CCCGAATCCT TATTAAGCGC CGAAATCAGG CAGATAAAGC CATACAGGCA
GATAGACCTC TACCTATTAA ATCGGCTTCT AGGCGCGCTC CATCTAAATG
TTCTGGCTGT GGTGTACAGG GGCATAAAAT TACGCACTAC CCGAATCGAT
AGAACTACTC ATTTTTATAT AGAAGTCAGA ATTCATAGTG TTTTGATCAT
TTTAAATTTT TATATGGCGG GTGGTGGGCA ACTCGCTTGC GCGGGCAACT
CGCTTACCGA TTACGTTAGG GCTGATATTT ACGTGAAAAT CGTCAAGGGA
TGCAAGACCA AAGTAGTAAA ACCCCGGAAG TCAACAGCAT CCAAGCCCAA
GTCCTTCACG GAGAAACCCC AGCGTCCACA TCACGAGCGA AGGACCACCT
CTAGGCATCG GACGCACCAT CCAATTAGAA GCAGCAAAGC GAAACAGCCC
AAGAAAAAGG TCGGCCCGTC GGCCTTTTCT GCAACGCTGA TCACGGGCAG
CGATCCAACC AACACCCTCC AGAGTGACTA GGGGCGGAAA TTTAAAGGGA
TTAATTTCCA CTCAACCACA AATCACAGTC GTCCCCGGTA TTGTCCTGCA
GAATGCAATT TAAACTCTTC TGCGAATCGC TTGGATTCCC CGCCCCTAGT
CGTAGAGCTT AAAGTATGTC CCTTGTCGAT GCGATGTATC ACAACATATA
AATACTAGCA AGGGATGCCA TGCTTGGAGG ATAGCAACCG ACAACATCAC
ATCAAGCTCT CCCTTCTCTG AACAATAAAC CCCACAG.
```

47. The process of claim 34, wherein the promoter and upstream activating sequences have the following sequence:

```
AGATCTGCCC TTATAAATCT CCTAGTCTGA TCGTCGACGC ATTCCGAATA
CGAGGCCTGA TTAATGATTA CATACGCCTC CGGGTAGTAG ACCGAGCAGC
CGAGCCAGTT CAGCGCCTAA AACGCCTTAT ACAATTAAGC AGTTAAAGAA
GTTAGAATCT ACGCTTAAAA AGCTACTTAA AAATCGATCT CGCAGTCCCG
ATTCGCCTAT CAAAACCAGT TTAAATCAAC TGATTAAAGG TGCCGAACGA
GCTATAAATG ATATAACAAT ATTAAAGCAT TAATTAGAGC AATATCAGGC
CGCGCACGAA AGGCAACTTA AAAAGCGAAA GCGCTCTACT AAACAGATTA
CTTTTGAAAA AGGCACATCA GTATTTAAAG CCCGAATCCT TATTAAGCGC
CGAAATCAGG CAGATAAAGC CATACAGGCA GATAGACCTC TACCTATTAA
ATCGGCTTCT AGGCGCGCTC CATCTAAATG TTCTGGCTGT GGTGTACAGG
GGCATAAAAT TACGCACTAC CCGAATCGAT AGAACTACTC ATTTTTATAT
AGAAGTCAGA ATTCATAGTG TTTTGATCAT TTTAAATTTT TATATGGCGG
GTGGTGGGCA ACTCGCTTGC GCGGGCAACT CGCTTACCGA TTACGTTAGG
GCTGATATTT ACGTGAAAAT CGTCAAGGGA TGCAAGACCA AAGTAGTAAA
ACCCCGGAAG TCAACAGCAT CCAAGCCCAA GTCCTTCACG GAGAAACCCC
AGCGTCCACA TCACGAGCGA AGGACCACCT CTAGGCATCG GACGCACCAT
CCAATTAGAA GCAGCAAAGC GAAACAGCCC AAGAAAAAGG TCGGCCCGTC
GGCCTTTTCT GCAACGCTGA TCACGGGCAG CGATCCAACC AACACCCTCC
AGAGTGACTA GGGGCGGAAA TTTAAAGGGA TTAATTTCCA CTCAACCACA
AATCACAGTC GTCCCCGGTA TTGTCCTGCA GAATGCAATT TAAACTCTTC
TGCGAATCGC TTGGATTCCC CGCCCCTAGT CGTAGAGCTT AAAGTATGTC
CCTTGTCGAT GCGATGTATC ACAACATATA AATACTAGCA AGGGATGCCA
TGCTTGGAGG ATAGCAACCG ACAACATCAC ATCAAGCTCT CCCTTCTCTG
AACAATAAAC CCCACAGAAG GCATTT.
```

48. The process of claim 44, wherein the promoter and upstream activating sequence is preceded by a 1.05 kb unsequenced upstream region from position 0 to 1.05 in plasmid pTAKA 17.

49. The process of claim 34, wherein the vector system further comprises a preregion providing for secretion of the product into the culture medium.

50. The process of claim 49, wherein the preregion is derived from the gene for A. oryzae TAKA amylase, A. niger neutral α-amylase, A. niger acid-stable α-amylase, B. licheniformis α-amylase, the maltogenic amylase from Bacillus NCIB 11837, B. stearothennophilus α-amylase or B. licheniformis subtilisin.

51. The process of claim 49, wherein the preregion is the preregion of an Aspergillus gene.

* * * * *